United States Patent [19]

Stirling et al.

[11] 4,359,473
[45] Nov. 16, 1982

[54] α-AMINO DEOXY CLAVULANIC ACID ANTIBACTERIAL AGENTS

[75] Inventors: Irene Stirling, Reigate; Brian P. Clarke, Kingswood, both of England

[73] Assignee: Beecham Group Limited, England

[21] Appl. No.: 72,234

[22] Filed: Sep. 4, 1979

Related U.S. Application Data

[63] Continuation-in-part of Ser. No. 56,071, Jul. 9, 1979, which is a continuation-in-part of Ser. No. 896,441, Apr. 14, 1978, abandoned.

[30] Foreign Application Priority Data

| Apr. 22, 1977 | [GB] | United Kingdom | 1674/77 |
| Sep. 6, 1977 | [GB] | United Kingdom | 37072/77 |
| Dec. 2, 1977 | [GB] | United Kingdom | 50229/77 |
| Dec. 23, 1977 | [GB] | United Kingdom | 53866/77 |
| Jul. 29, 1978 | [GB] | United Kingdom | 31624/78 |
| Sep. 9, 1978 | [GB] | United Kingdom | 36265/78 |
| Sep. 9, 1978 | [GB] | United Kingdom | 36270/78 |

[51] Int. Cl.³ .................. C07D 498/04; A61K 31/42
[52] U.S. Cl. .................. 424/272; 260/245.3; 542/420
[58] Field of Search .......... 260/245.3; 424/272; 542/420

[56] References Cited

U.S. PATENT DOCUMENTS 4,078,067  3/1978  Christensen .......... 260/245.3
4,256,638  3/1981  Ponsford et al. ........ 260/245.3

FOREIGN PATENT DOCUMENTS 2646003  4/1977  Fed. Rep. of Germany.

Primary Examiner—Mark L. Berch
Attorney, Agent, or Firm—Jacobs & Jacobs

[57] ABSTRACT

The compounds of the formula (XVII)

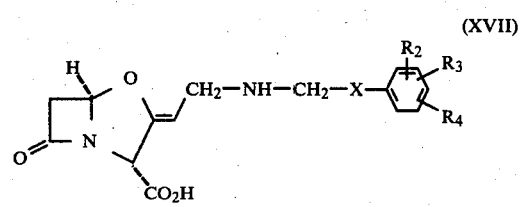

and their esters wherein $R_2$ is a hydrogen, fluorine, chlorine or bromine atom or an alkyl group of 1-3 carbon atoms, an alkoxyl group of 1-3 carbon atoms, an acyloxyl group of 1-3 atoms, a hydroxyl group, an alkoxycarbonyl group containing 1-3 carbon atoms in the alkoxy part, or a group $-N(R_5)CO.R_6$, $-N(R_5)SO_2R_6$ or $-CO-NR_5R_6$ where $R_5$ is a hydrogen atom or an alkyl group of 1-3 carbon atoms or a phenyl or benzyl group and $R_6$ is an alkyl group of 1-3 carbon atoms or a phenyl or benzyl group; $R_3$ is a hydrogen, fluorine or chlorine atom or an alkyl group of 1-3 carbon atoms, an alkoxyl group of 1-3 carbon atoms; or an acyloxyl group of 1-3 carbon atoms $R_4$ is a hydrogen fluorine or chlorine atom or an alkyl group of 1-3 atoms or an alkoxyl group of 1-3 carbon atoms; and X is a bond or alkylene group of 1-4 carbon atoms; have been found to be β-lactamase inhibitors and antibacterial agents. Their preparation and use is described.

69 Claims, No Drawings

α-AMINO DEOXY CLAVULANIC ACID ANTIBACTERIAL AGENTS

This application is a continuation-in-part of application Ser. No. 056,071 filed July 9, 1979, which is a C.I.P. of Ser. No. 896,441, filed Apr. 14, 1978, now abandoned.

The present invention relates to β-lactam antibacterial agents, to the process for their preparation and to compositions containing them.

British Patent No. 1565209 (see also U.S. Ser. No. 731,928 ABN, Belgian Patent No. 847044 and West German Offenlegungsschrift No. P2646003.7) discloses inter alia the compounds of the formula (I):

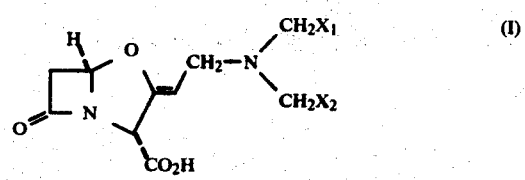

and esters thereof wherein $X_1$ is hydrogen atom, an alkyl group of up to 5 carbon atoms, an alkenyl group of up to 5 carbon atoms, a hydroxy alkyl group of up to 5 carbon atoms or an optionally substituted phenyl group and $X_2$ is an optionally substituted phenyl group, such compounds were described as antibacterial agents and β-lactamase inhibitors.

It has now been discovered that certain secondary amines can be prepared that are β-lactamase inhibitors that enhance the effectiveness of penicillins or cephalosporins and which also have antibacterial properties in their own right.

The present invention provides a compound of the formula (II):

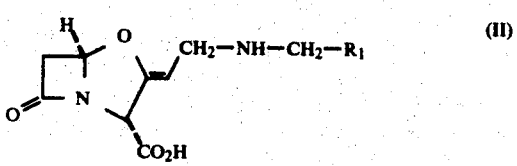

or an ester thereof wherein $R_1$ is a hydrogen atom, an alkyl group of up to 5 carbon atoms, a cycloalkyl group of 5 or 6 carbon atoms, a hydroxyalkyl group of up to 5 carbon atoms or a moiety of the sub-formula (a):

wherein $R_2$ is a hydrogen, fluorine, chlorine or bromine atom or an alkyl group of 1-3 carbon atoms, an alkoxyl group of 1-3 carbon atoms, an acyloxyl group of 1-3 carbon atoms, a hydroxyl group, an alkoxycarbonyl group containing 1-3 carbon atoms in the alkoxy part, or a group —N($R_5$)CO.$R_6$, —N($R_5$)SO$_2$R$_6$ or —CO—NR$_5$R$_6$ where $R_5$ is a hydrogen atom or an alkyl group of 1-3 carbon atoms or a phenyl or benzyl group and $R_6$ is an alkyl group of 1-3 carbon atoms or a phenyl or benzyl group; $R_3$ is a hydrogen, fluorine or chlorine atom or an alkyl group of 1-3 carbon atoms, an alkoxyl group of 1-3 carbon atoms or an acyloxyl group of 1-3 carbon atoms; and $R_4$ is a hydrogen fluorine or chlorine atom or an alkyl group of 1-3 carbon atoms or an alkoxyl group of 1-3 carbon atoms.

The compounds of the formula (II) per se exist in the form of zwitterions, that is they may be represented as shown in formula (IIa):

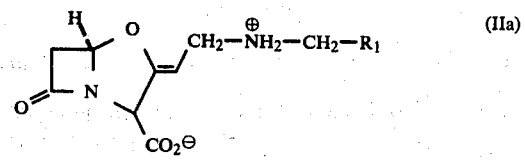

if desired wherein $R_1$ is as defined in relation to formula (II). These zwitterionic compounds form a favoured aspect of this invention in view of their generally crystalline form and their greater stability than previously reported β-lactamase inhibitory amines such as those of the formula (I).

The esters of the compounds of the formula (II) may be presented in the form of the free base or in the form of an acid addition salt.

Suitably $R_1$ is a hydrogen atom. Suitably $R_1$ is an alkyl group of up to 5 carbon atoms. Suitably $R_1$ is a hydroxyalkyl group of up to 5 carbon atoms. Suitably $R_1$ is a phenyl group optionally substituted by a fluorine, chlorine or bromine atom or an alkyl or alkoxyl group of up to 3 carbon atoms.

Apt groups $R_1$ include the methyl, ethyl, propyl, butyl, hydroxymethyl, hydroxyethyl, hydroxypropyl, phenyl, p-methoxyphenyl, p-methylphenyl and the like groups. Certain particularly apt groups $R_1$ include the methyl, ethyl hydroxymethyl, 2-hydroxyethyl, isopropyl and phenyl groups.

A group of suitable compounds of this invention are those of the formula (II) or an ester thereof wherein $R_1$ is a hydrogen atom an alkyl group of up to 5 carbon atoms, a hydroxyalkyl grup of up to 5 carbon atoms or a moiety of the sub-formula (b):

wherein $R_2$ is a hydrogen, fluorine, chlorine or bromine atom or an alkyl group of 1-3 carbon atoms, an alkoxyl group of 1-3 carbon atoms, an acyloxy group of 1-3 carbon atoms, a hydroxyl group or an alkoxycarbonyl group containing 1-3 carbon atoms in the alkoxy part; $R_3$ is a hydrogen, fluorine or chlorine atom or an alkyl group of 1-3 carbon atoms, an alkoxyl group of 1-3 carbon atoms or an acyloxyl group of 1-3 carbon atoms; and $R_4$ is hydrogen, fluorine or chlorine atom or an alkyl group of 1-3 carbon atoms or an alkoxyl group of 1-3 carbon atoms. As described above these compounds may be in the form of the zwitterion or an ester or an acid addition salt of said ester. Suitable and apt values for $R_1$ include those set forth hereinbefore in relation to formula (II).

One favoured sub-group of compounds within formula (II) include those of the formula (III):

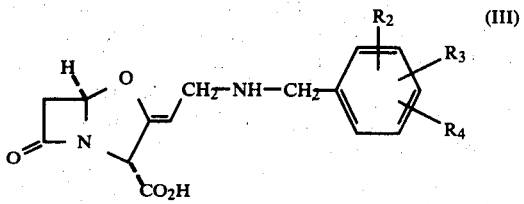

and esters thereof wherein $R_2$, $R_3$ and $R_4$ are as defined hereinbefore.

These compounds of the formula are favourably in the form of the zwitterion for reasons hereinbefore indicated. The compounds of the formula (III) may be presented in the form of the ester and suitably that ester is in the form of its acid addition salt.

More suitably $R_2$ is a hydrogen, fluorine or chlorine atom or a methoxyl, ethoxyl, hydroxyl, acetoxyl, propionyloxy, methyl, ethyl, methoxycarbonyl or ethoxycarbonyl group.

More suitably $R_3$ is a hydrogen, fluorine or chlorine atom or a methoxyl, ethoxyl, acetoxyl, propionoxyl, methyl or ethyl group.

More suitably $R_4$ is a hydrogen, fluorine or chlorine atom or a methoxyl, ethoxyl, acetoxyl, propionoxyl, methyl or ethyl group.

Most suitably $R_2$ is a hydrogen, fluorine or chlorine atom or a methoxyl, hydroxyl or methyl group.

Most suitably $R_3$ is a hydrogen, fluorine or chlorine atom or a methoxyl or methyl group.

Most suitably $R_4$ is a hydrogen atom or a methyl or methoxyl group.

Preferably $R_2$ is a hydrogen, fluorine or chlorine atom or a methyl or methoxyl group.

Preferably $R_3$ is a hydrogen atom or methoxyl group.

Preferably $R_4$ is a hydrogen atom.

The compounds of this invention are particularly those of the formula (III) show a broad spectrum of β-lactamase inhibitory activity.

Certain particularly favoured compounds of the formula (III) include those of the formula (IV):

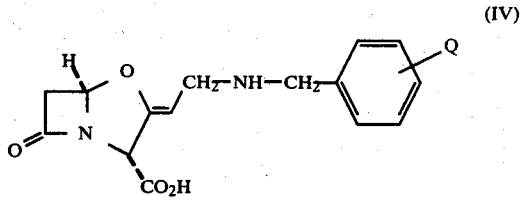

wherein Q is a hydrogen, fluorine or chlorine atom or a methyl, methoxyl, ethyl or ethoxyl group.

Suitably Q is a hydrogen, p-fluorine, m-fluorine, p-chlorine or m-chlorine atom or a p-methyl, m-methyl, p-methoxyl or m-methoxyl group.

Most suitably Q is a hydrogen, p-fluorine or p-chlorine atom or a p-methyl or p-methoxyl group.

A compound of the formula (IV) which has shown particularly good synergistic activity in-vivo is that wherein Q is a hydrogen atom. This compound is able to enhance the effectiveness of penicillins, such as ampicillin or amoxycillin, and cephalosporins against various β-lactamase producing strains of gram-negative bacteria including strains of *Klebsiella aerogenes*, *Escherichia coli*, *Proteus mirabilis* and the like and especially against β-lactamase producing strains of gram-positive bacteria such as *Staphylococcus aureus* when administered orally and especially when administered by injection. The compounds of the formula (IV) also have an advantageously low acute toxicity, for example no deaths in test animals were observed when administering therapeutic amounts of the synergist. In addition such compounds are effective when used alone in treatment of infections due to β-lactamase producing as well as non-β-lactamase producing strains of *Staphylococcus aureus*. Thus, for example, the compound of the formula (IV) wherein Q is a hydrogen atom has proved more effective than ampicillin, cloxacillin or cefazolin in treating certain infections due to *Staphylococcus aureus* Russell.

A further favoured sub-group of compounds within formula (II) having similar properties to that of the sub-group of the formula (IV) is that of the formula (V):

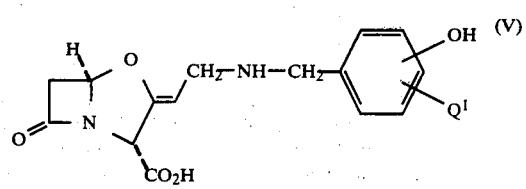

wherein $Q^1$ is a hydrogen, fluorine or chlorine atom or a methyl, ethyl, methoxyl, ethoxyl or hydroxyl group.

Suitably the OH substituent shown in formula (VIa) is para- to the carbon to which the —NH—CH$_2$— moiety is attached.

Suitably the OH substituent shown in formula (VIa) is meta- to the carbon atom to which the —NH—CH$_2$— moiety is attached.

Most suitably $Q^1$ is a hydrogen atom or a methyl or methoxyl group.

The zwitterionic compounds of the formula (IV) and (V) are normally and preferably in crystalline form.

A further sub-group of favoured compounds of this invention are those of the formula (II) wherein $R_2$ is a group $N(R_5)CO.R_6$, $N(R_5)SO_2R_6$ or $CONR_5R_6$ wherein $R_5$ and $R_6$ are as defined in relation to formula (II) and esters thereof. Suitably $R_5$ is a hydrogen atom. Suitably $R_5$ is an alkyl group of 1–3 carbon atoms such as the methyl group. Suitably $R_6$ is an alkyl group of 1–3 carbon atoms. More suitably $R_6$ is a methyl group. Suitable values for $R_3$ and $R_4$ in such compounds are those specified in relation to the compounds of the formula (II). Such compounds may be in the form of zwitterions of the parent acid. Esters of such compounds may be in the form of the free base or may be in the form of an acid addition salt.

A further particularly favoured sub-group of the compounds of the formula (II) is that of the formula (VI):

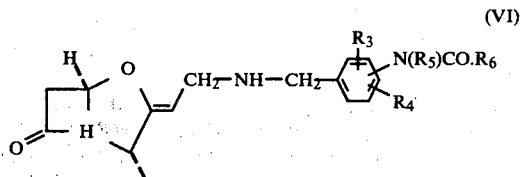

wherein $R_3$, $R_4$, $R_5$ and $R_6$ are as defined in relation to formula (II).

The compounds of the formula (VI) are generally produced in crystalline form and in better than average yield and have similar activity to those of the formula (IV) and (V).

In relation to the compounds of formula (VI) it is more suitable that $R_5$ is a hydrogen atom or an alkyl group of 1-3 carbon atoms such as a methyl group and most suitably $R_5$ is a hydrogen atom. In relation to the compounds of the formula (VI) it is more suitable that $R_6$ is an alkyl group of 1-3 carbon atoms such as the methyl group.

Favoured values for $R_3$ and $R_4$ for the compounds of the formula (VI) are as defined in relation to formulae (II) and (III). Preferably $R_3$ and $R_4$ are both hydrogen atoms.

Suitably in the compounds of the formula (VI) the $-N(R_5)COR_6$ moiety is attached para to the $-NH-CH_2-$ moiety.

Suitably in the compounds of the formula (VI) the $-N(R_5)COR_6$ moiety is attached meta to the $-NH-CH_2-$ moiety.

A favoured sub-group of compounds of the formula (VI) are those of the formula (VII):

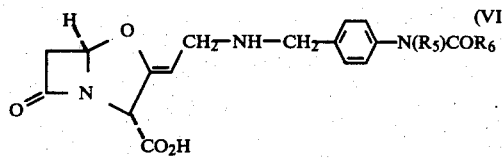

(VII)

wherein $R_5$ and $R_6$ are as defined in relation to formula (II). Particularly suitably $R_5$ is a hydrogen atom or an alkyl group of 1-3 carbon atoms such as a methyl group. Preferably $R_5$ is a hydrogen atom. Particularly suitably $R_5$ is an alkyl group of 1-3 carbon atoms and preferably a methyl group.

As has been previously indicated we prefer to prepare and use the crystalline zwitterionic compounds within formula (II) such as those of the formulae (III), (IV), (V), (VI) and (VII) and the like. However, esters of the compounds of the formulae (II)-(VII) also form part of this invention, for example as the free base or as the acid addition salt, since such compounds may also be used to enhance the effectiveness of penicillins or cephalosporins.

Certain suitable esters of the compounds of the formula (II)-(VII) include those of the formula (VIII) and (IX):

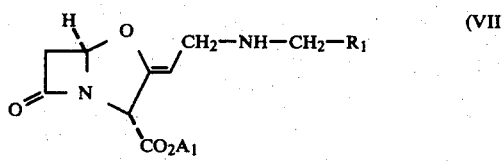

(VIII)

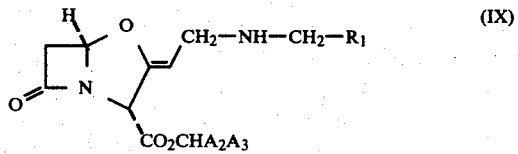

(IX)

wherein $R_1$ is as defined in relation to formula (II) or is a substituted phenyl group as present in a compound of the formula (III)-(VII) wherein $A_1$ is an alkyl group of 1-6 carbon atoms optionally substituted by an alkoxyl or acyloxyl group of 1-7 carbon atoms; $A_2$ is an alkenyl or alkynyl group of up to 5 carbon atoms or is a phenyl group optionally substituted by a fluorine, chlorine, bromine, nitro or alkyl or alkoxyl of up to 4 carbon atoms; and $A_3$ is a hydrogen atom, an alkyl group of up to 4 carbon a atoms or a phenyl group optionally substituted by a fluorine, chlorine, bromine, nitro or alkyl or alkoxyl of up to 4 carbon atoms.

Suitable esters of the compounds of the formula (II) include the methyl, ethyl, n-propyl, n-butyl, allyl, $CH_2-C\equiv CH$, methoxymethyl, acetoxymethyl, propionoxymethyl, pivaloyloxymethyl, ethoxycarbonyloxymethyl, methoxycarbonyloxyethyl, ethoxycarbonyloxyethyl, dimethoxyphthalidyl, benzyl, methoxybenzyl, ethoxybenzyl, nitrobenzyl, chlorobenzyl or the like ester.

Certain favoured groups $A_1$ include the methyl, methoxymethyl, acetoxymethyl, acetoxyethyl, phthalidyl, ethoxycarbonyloxymethyl, α-ethoxycarbonyloxyethyl and the like groups.

Certain favoured groups $A_2$ include the phenyl and 4-methoxyphenyl groups. A particularly favoured moiety $A_3$ is the hydrogen atom.

Certain other favoured values for $A_1$ includes those of the sub-formulae (c), (d) and (e):

$$-CHA_5-OA_6 \quad (c)$$

$$-CHA_5-COA_6 \quad (d)$$

$$CHA_5-CO_2A_6 \quad (e)$$

wherein $A_5$ is a hydrogen atom or a methyl group and $A_6$ is an alkyl group of up to 4 carbon atoms or a phenyl or benzyl group either of which may be substituted by one or two alkyl or alkoxyl group of up to 3 carbon atoms or by a fluorine, chlorine or bromine atom or a nitro group; or $A_5$ is joined to $A_6$ to form the residue of an unsubstituted saturated 5- or 6-membered heteroalicyclic ring or an ortho-phenylene group which may be substituted by one or two alkyl or alkoxyl groups of up to 3 carbon atoms or by a fluorine, chlorine or bromine atom or nitro group.

An apt acylic value for the sub-group of the formula (c) is $-CH_2-OA_6$.

An apt acylic value for the sub-group of the formula (d) is $-CH_2-CO-A_6$.

An apt acylic value for the sub-group of the formula (e) is $-CH_2-CO_2A_6$.

A further apt acylic value for the sub-group of the formula (e) is $-CH(CH_3)-CO_2A_6$.

Favoured values for $A_6$ in the preceding acylic moieties include the methyl, ethyl, propyl, butyl, phenyl and benzyl groups.

Apt cyclic values for the sub-group of the formula (c) include the tetrahydropyranyl and tetrahydrofuranyl groups.

Esters of the compounds of the formula (II) such as those of the compounds of the formulae (IV) or (V) may be presented in the form of their acid addition salts if desired. The acid used to form the salt will most suitably be pharmaceutically acceptable, but non-pharmaceutically acceptable acid addition salts are also envisaged, for example as intermediates in the preparation of the pharmaceutically acceptable salts by ion exchange. Suitable pharmaceutically acceptable acid additon salts include those of inorganic and organic acids, such as hydrochloric, phosphoric, sulphuric, methane-sulphonic, toluenesulphonic, citric, malic, acetic, lactic, tartaric, propionic, succinic or the like acid. Most suitably the acid addition salt is provided as a solid and preferably as a crystalline solid.

Compounds of this invention wherein crystalline form may be solvated, for example hydrated.

An especially preferred value of $R_1$ for inclusion in compounds of the formulae (II), (IIa), (VIII) and (IX) is the isopropyl group. 9-N-Isobutylaminodeoxyclavulanic acid has especially desirable solubility and activity properties.

The present invention provides a pharmaceutical composition which comprise a compound of this invention and a pharmaceutically acceptable carrier.

The compositions of the invention include those in a form adapted for oral, topical or parenteral use and may be used for the treatment of the infection in mammals including humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials such as diluents, binders, colours, flavours, preservatives, disintegrant and the like in accordance with conventional pharmaceutical practice in the manner well understood by those skilled in the art of formulating antibiotics.

Injectable or infusable compositions of a compound of the invention are particularly suitable as high blood levels of the compound can occur after administration by injection or infusion. Thus, one preferred composition aspect of this invention comprises a compound of the invention in sterile form and most suitably in sterile crystalline form. The zwitterionic compounds of this invention are particularly suitable for use in such compositions.

The injectable solution of the compound of this invention may be made up in a sterile pyrogen-free liquid such as water, aqueous ethanol or the like.

Compounds of this invention when in highly pure crystalline form tend to have relatively low aqueous solubilities so that if it is desired to administer substantial quantities of the medicament this can require fairly large quantities of water for reconstitution. In these circumstances it is often convenient to administer the solution intravenously.

An alternative approach to administering the compounds of this invention and especially those zwitterionic compounds of the formula (III)—(VII) is to utilise an injectable suspension. Such suspensions may be made up in sterile water; sterile saline or the like and may also contain suspending agents such as polyvinylpyrrolidone, lecithin or the like (for example in the manner described for amoxycillin trihydrate in Belgian Patent No. 839109). Alternatively such compositions may be prepared in an acceptable oily suspending agent such as arachis oil or its equivalent. The use of suspensions can give rise to advantageously prolonged blood levels of the medicament. Belgian Patent No. 839109 may be consulted for suitable methods and materials for producing injectable aqueous suspensions. For use in such suspensions the zwitterionic compound of this invention should be in the form of fine particles as described in said Belgian Patent.

Unit dose compositions comprising a compound of this invention adapted for oral administration form a further suitable composition aspect of this invention. However, orally administrable forms are generally less favoured than injectable forms owing to the relatively poor absorption of the compounds from the gastrointestinal tract. Despite this orally administrable compositions are of use as a synergistically effective blood level can be expected at high doses and at lower doses such compositions may be used to treat infections localised in the gastro-intestinal tract.

Unit dose compositions comprising a compound of this invention adapted for topical administration are also presented by this invention. In this instance 'topical administration' also includes local administration to internal surfaces of mammary glands of cattle, for example during the treatment of mastitis by intra-mammary administration.

The compound of the formula may be present in the composition as sole therapeutic agent or it may be present together with other therapeutic agents such as a penicillin or cephalosporin. Considerable advantages accrue from the inclusion of a penicillin or cephalosporin since the resulting composition shows enhanced effectiveness (synergy).

Suitable penicillins for inclusion in the compositions of this invention include benzylpenicillin, phenoxymethyl-penicillin, carbenicillin, azidocillin, propicillin, ampicillin, amoxycillin, epicillin, ticarcillin, cyclacillin, pirbenicillin, azlocillin, mezlocillin, celbenicillin, and other known penicillins including pro-drugs therefore such as their in-vivo hydrolysable esters such as the acetoxymethyl, pivaloyloxymethyl, α-ethoxycarbonyloxyethyl or phthalidyl esters of ampicillin, benzylpenicillin or amoxycillin, and aldehyde or ketone adducts of penicillins containing an 6-α-aminoacetamide side chain (such as hetacillin, metampicillin and analogous derivatives of amoxycillin) or α-esters of carbenicillin or ticarcillin such as their phenyl or indanyl α-esters.

Suitable cephalosporins for inclusion in the compositions of this invention include cefatrizine, cephaloridine, cephalothin, cefazolin, cephalexin, cephacetrile, cephamandole nafate, cephapirin, cephradine, 4-hydroxycephalexin, cefaparole, cephaloglycin, and other known cephalosporins or pro-drugs thereof.

Such compounds are frequently used in the form of a salt of hydrate of the like.

Naturally if the penicillin or cephalosporin present in the composition is not suitable for oral administration then the composition will be adapted for parenteral administration. As previously indicated such injectable or infusable compositions are preferred.

Highly favoured penicillins for use in the compositions of this invention include ampicillin, amoxycillin, carbenicillin and ticarcillin. Such penicillins may be used as a pharmaceutically acceptable salt such as the sodium salt. Alternatively the ampicillin or amoxycillin may be used in the form of fine particles of the zwitterionic form (generally as ampicillin trihydrate or amoxycillin trihydrate) for use in an injectable suspension, for example, in the manner hereinbefore described for a compound of this invention.

The preferred penicillin for use in the synergistic composition is amoxycillin, for example as its sodium salt or trihydrate.

Particularly suitable cephalosporins for use in the compositions of this invention include cephaloridine and cefazolin. Such cephalosporins may be used as a pharmaceutically acceptable salt, for example the sodium salt.

when present together with a cephalosporin or penicillin, the ratio of a compound of the invention to the penicillin or cephalosporin agent may vary over a wide range of ratios, such as from 10:1 to 1:10 for example about 3:1, 2:1, 1:1, 1:2, 1:3, 1:4, 1:5 or 1:6, (wt/wt, based on pure free antibiotic equivalent). Orally administrable compositions containing a compound of the invention will normally contain relatively more synergist than corresponding injectable compositions, for example the ratio in an oral composition may be from about 3:1 to about 1:1 whereas a corresponding injectable composition may contain a ratio of about 1:1 to about 1:3 (compound of the invention: penicillin or cephalosporin).

The total quantity of a compound of the invention in any unit dosage form will normally be between 25 and 1000 mg and will usually be between 50 and 500 mg, for example about 62.5, 100, 125, 150, 200 or 250 mg.

Compositions of this invention may be used for the treatment of infections of inter alia, the respiratory tract, the urinary tract and soft tissues in humans and mastitis in cattle.

Normally between 50 and 1000 mg of the compounds of the invention will be administered each day of treatment but more usually between 100 and 750 mg of the compounds of the invention will be administered per day, for example as 1–6 doses, more usually as 2, 3 or 4 doses.

The penicillin or cephalosporin in the synergistic composition of this invention will normally be present at approximately the amount at which it is conveniently used which will usually be expected to be from about 62.5 to 1000 mg per dose, more usually about 125, 250 or 500 mg per dose.

One particularly favoured composition of this invention will contain from 150 to 1000 mg of amoxycillin as the trihydrate or sodium salt and from 25 to 500 mg of a compound of this invention.

Most suitably this form of composition will contain a compound of the formula (III)–(VIII).

A further particularly favoured composition of this invention will contain from 150 to 1000 mg of ampicillin or a pro-drug therefor and from 25 to 500 mg of a compound of this invention.

Most suitably this form of composition will contain ampicillin trihydrate, ampicillin anhydrate, sodium ampicillin, hetacillin, pivampicillinhydrochloride, bacampicillin hydrochloride, or talampicillin hydrochloride. Most suitably this form of the composition will contain a compound of the formula (III)–(VIII).

Most suitably the preceding compositions will contain from 200 to 700 mg of the penicillin component. Most suitably the preceding composition will comprise from 50 to 250 mg of a compound of the formula (III)–(VIII) preferably in crystalline form.

Such compositions may be adapted for oral or parenteral use except when containing an in-vivo hydrolysable ester of ampicillin or amoxycillin in which case the compositions will not be adapted for parenteral administration.

Another particularly favoured composition of this invention will contain from 200 to 2000 mg of carbenicillin, ticarcillin or a pro-drug therefor and from 50 to 500 mg of a compound of the invention.

Suitably this form of composition will contain di-sodium carbenicillin. Suitably this form of the composition will contain di-sodium ticarcillin.

More suitably this form of the composition will contain from 75 to 250 mg of a compound of the formula (III)–(VIII) preferably in crystalline form. Such compositions containing di-salts of carbenicillin and ticarcillin will be adapted for parenteral administration.

The present invention also provides a method of treating bacterial infections in humans or domestic mammals which comprises the administration of a composition of this invention.

Commonly the infection treated will be due to a strain of *Staphylococcus aureus, Klebsiella aerogenes, Escherichia coli,* Proteus sp. or the like. The organisms believed to be most readily treated by an antibacterially effective amount of a compound of this invention is *Staphylococcus aureus.* The other organisms named are more readily treated by using a synergistically effective amount of the compound of the invention and a penicillin or cephalosporin. The administration of the two components may take place separately but in general it we prefer to use a composition containing both the synergist and the penicillin or cephalosporin.

The indications for treatment include respiratory tract and urinary tract infections in humans and mastitis in cattle.

An especially preferred compound for use in the compositions of this invention as hereinbefore described is 9-N-isobutylaminodeoxyclavulanic acid. In injectable compositions the increased aqueous solubility of 9-N-isobutylaminodeoxyclavulanic acid is a very considerable advantage allowing for the preparation of sterile compositions containing not less than 15% w/w of 9-N-isobutylaminodeoxyclavulanic acid, favourably not less than 20% w/w of 9-N-isobutylaminodeoxyclavulanic acid and preferably not less than 25% w/w of 9-N-isobutylaminodeoxyclavulanic acid. This means that the compounds are easier to administer than the previously known compounds. In this circumstance it is often convenient to administer the solution by intramuscular injection which is less complicated than intravenous administration. This invention also provides the use of 9-N-isobutylaminodeoxyclavulanic acid for preparing injectable aqueous solutions. Such solutions may be prepared by dissolving sterile 9-N-isobutylaminodeoxyclavulanic acid in sterile water. Suitably this water is "Water for Injection BP" or the equivalent and may contain electrolytes to render it isotonic.

A preferred penicillin for use in the compositions is sodium amoxycillin. Amoxycillin trihydrate is also particularly apt.

The present invention also provides a process for the preparation of a compound of the formula (II) as hereinbefore defined or an ester thereof which process comprises the hydrogenation of a compound of the formula (X):

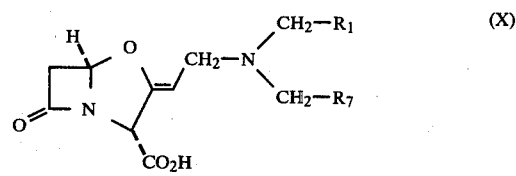

or an ester thereof wherein $R_1$ is as defined in relation to formula (II) and $R_7$ is a group of the sub-formula (a) as defined in relation to formula (II); and thereafter if desired esterifying the zwitterion of the formula (IIa) as hereinbefore defined which was produced by the hydrogenation of the compound of the formula (X) or a hydrogenolysable ester thereof.

When used herein the term "hydrogenolysable ester" means an ester which on hydrogenation is cleaved to yield the parent carboxylic acid.

The hydrogenation is normally carried out in the presence of a transition metal catalyst.

The catalyst we have preferred to use is palladium, for example in the form of palladium on carbon (charcoal), palladium on barium sulphate, palladium on calcium carbonate or the like.

A favoured catalyst is palladium on carbon (sometimes referred to as palladium on charcoal); for example 5%, 10%, 20% or 30% palladium on carbon. The higher palladium content catalyst are particularly apt as smaller total weights of catalyst can be employed thereby avoiding possible problems associated with absorption of product onto the carbon.

A low, medium or high pressure of hydrogen may be used in this reaction, for example from 1 to 6 atmospheres. In general if the catalyst used contains a lower precentage of palladium (for example 5% or 10% palladium) then better yields of the desired product are obtained using a pressure of about 3 to 5 atmospheres of hydrogen, for example about 4 atmospheres of hydrogen. In general if the catalyst used contains a higher percentage of palladium (for example 20% or 30% palladium) then acceptable yields of the desired product may also be obtained at low and medium pressures of hydrogen, for example about 1 to 2 atmospheres of hydrogen. We have found it convenient to use an atmospheric or slightly superatmospheric pressure of hydrogen in conjunction with higher palladium content catalysts.

The reaction is normally carried out at a non-extreme temperature, for example from 0° C. to 30° C. and more usually from 12° C. to 25° C. It is generally convenient to carry out the reaction at ambient temperature.

Suitable solvents for carrying out the hydrogenation include ethanol, n-propanol, isopropanol, tetrahydrofuran, dioxane, ethyl acetate or mixtures of such solvents or such solvents in the presence of water. A favoured solvent is aqueous tetrahydrofuran. A further favoured solvent is a mixture of isopropanol, tetrahydrofuran and water.

Suitably $R_1$ is as group of the sub-formula (b) as hereinbefore defined.

When $R_1$ is a substituted phenyl group then $R_7$ is more suitably a similarly substituted phenyl group or is a phenyl group.

Most suitably $R_7$ is a phenyl group.

Most suitably $R_1$ is a phenyl or substituted phenyl group as shown in and defined as in relation to any of formulae (III)-(VII).

We have preferred to carry out the hydrogenation reaction on a hydrogenolysable ester of a compound of the formula (X) so that a compound of the formula (II) per se is formed by the hydrogenation. Such hydrogenation reactions proceeds at least in part via the formation of a compound of the formula (X). Favoured hydrogenolysable esters include benzyl and substituted benzyl esters such as methoxybenzyl, nitrobenzyl (for example the p-nitrobenzyl ester), chlorobenzyl, bromobenzyl and like esters. A particularly suitable hydrogenolysable ester is the benzyl esters. A further particularly suitable hydrogenolysable ester is the p-methoxybenzyl ester.

The product may generally be isolated from the reaction mixture by filtering off the solids (the catalyst, which should be well washed to remove the product) and then evaporating the solvent, preferably under low pressure, to yield the initial product. Further purification may be effected by such conventional methods as chromatography over cellulose or other mild stationary phase eluting with a $C_{1-4}$ alkanol optionally in the presence of water and optionally in the presence of tetrahydrofuran. Evaporation of the combined active fraction (identified by aqueous potassium permanganate spray on tlc) then yields the desired compound in pure form. The desired product is normally obtained in crystalline form (unless it is an unsalted ester). Trituration under ethanol, isopropanol or the like $C_{1-4}$ alkanol or other conventional solvent such as a ketone, ether or ester solvent or other conventional solvent (for example of up to 6 carbon atoms and more suitably of up to 4 carbon atoms) may also be used to aid crystallisation. Recrystallisation from ethanol or the like may also be employed. The solvent used in such processes may advantageously be moist.

Zwitterionic compounds, such as those of the formulae (III)-(IV) may be obtained from higher yielding reactions by the addition of an $C_{1-4}$ alkanol such as cold ethanol or the like to the initial product.

The initial product of the lower yielding reactions may contain considerably impurities so that it may be advantageous to wash the initial product by dissolving in a water immiscible organic solvent and extracting into water. Evaporation of the aqueous phase, preferably under a good vacuum, then yields a purer product which may be further purified if desired as previously described.

Unsalted esters of the compounds of the formula (II) tend to be oils so that it is often more convenient for handling to convert them into solid acid addition salts, for example by reaction with one equivalent of an acid. Alternatively the non-hydrogenolysable ester of the compound of the formula (X) may be hydrogenated in the presence of one equivalent of an acid, that is they may be hydrogenated in the form of their acid addition salt.

The compounds of the formula (II) may be hydrogenated in the form of their acid addition salts with a strong acid but this is not a preferred form of the process of this invention.

The present invention also provides a process for the preparation of an ester of a compound of the formula (II) which process comprises the reaction of the compound of the formula (II) with an esterifying agent.

The zwitterionic compound of the formula (II) may be dissolved or suspended in a solvent such as dimethylformamide, hexamethylphosphoramide, dichloromethane, ethyl acetate or other non-esterifiable solvents and therein esterified. Suitable temperatures for such a reaction range from about 0° to about 25° C. Suitable esterifying reagents include reactive halides and their equivalents, alkyl oxonium salts and the like.

When a reagent such as a reactive iodide, chloride, bromide, tosylate, mesylate or the equivalent is used, the resulting salt is generally suitable for use in a composition of this invention. Alternatively, the salt may be converted to a free base or alternative salt. When an alkyl oxonium salt is used, it is preferred to convert the resulting tetrafluoroborate to the free base or alternative salt. The various aforementioned salts may be converted to the free base by neutralisation, for example by contacting a solution of the salt in water with an organic phase, neutralising the salt by adding a base and extracting the liberated amine into the organic phase. This amine may thereafter be re-salted by reacting with an appropriate acid, for example in a dry organic solvent. It is generally preferred to use not more than one equivalent of acid for this process. Alternatively, the originally formed salt may be converted into the alternative salt using an ion exchange material, for example, by passing an aqueous solution of one salt through a bed of an anion exchange resin in the form of the desired salt such as the chloride form.

The salts may normally be obtained in solid form by dissolving in a fairly polar organic solvent (such as ethanol, tetrahydrofuran or the like) and then precipitating using a non-polar solvent such as diethyl ether, cyclohexane or the like.

The salts of the esters of the compounds of the formula (II) may normally be obtained in crystalline form by conventional methods such as trituration under (or crystallisation or recrystallisation from) a suitable organic solvent such as ether, acetone, acetonitrile, tetrahydrofuran or the like.

The present invention also provides a process for the preparation of an ester of the compound of the formula (II) which process comprises the reaction of an acid addition salt of the compound of the formula (II) with an alcohol in the presence of a condensation promoting agent.

Suitable condensation promoting agents for use in this process include carbodiimides such as dicyclohexylcarbodiimide and the chemical equivalents thereof.

The acid addition salt may be formed in situ or may be preformed. The acid employed will normally be a strong acid such as a methane sulphonic acid, p-toluene sulphonic or the like or trifluoroacetic acid or the like.

The reaction is normally carried out in an inert organic solvent. When the ester being formed is that of a liquid alcohol it is convenient to use that alcohol as the solvent or as part of the solvent system. The esterification is generally performed at a non-extreme temperature such as 0° to 35° C., for example from about 10° to 25° C. Conveniently the reaction mixture may be performed at ambient temperature.

The present invention also provides a process for the preparation of an ester of a compound of the formula (II) which process comprises the hydrogenation of a corresponding ester of a compound of the formula (XI):

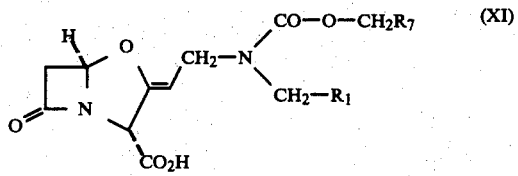

(XI)

wherein $R_1$ is as defined in relation to formula (II) and $R_7$ is as defined in relation to formula (X).

Most suitably $R_7$ is a phenyl group.

The ester of the compound of the formula (XI) is suitably an ester as defined in relation to formula (VIII) or less preferably as defined in relation to formula (IX).

Particularly suitable esters of the compound of the formula (XI) include $C_{1-4}$ alkyl esters especially the methyl and ethyl esters.

The hydrogenation may be performed under the same general conditions as hereinbefore described in relation to the hydrogenation of a compound of the formula (X).

A favoured solvent is tetrahydrofuran optionally in admixture with water or a $C_{1-4}$ alcohol such as ethanol. Conveniently the reaction uses an atmospheric pressure of hydrogen at an ambient temperature.

The present invention also provides a process for the preparation of an ester of a compound of the formula (XI) which process comprises the esterification of the compound of the formula (XI) of a salt thereof.

Most suitably this esterification is effected by the reaction of a salt of a compound of the formula (XI) with a reactive halide or the chemical equivalent thereof.

Suitable salts of the compound of the formula (XI) include the lithium, sodium, potassium and like salts. Suitable esterifying agent include reactive chlorides, bromides, iodides, acid anhydrides, tosylates, mesylates and the like.

The esterification may be effected in a conventional organic solvent such as acetone, dimethylformamide or the like. The reaction is normally effected at a non-extreme temperature such as 0° to 35° C., for example 10° to 25° C. Conveniently the reaction is performed at ambient temperature.

The acid of the formula (XI) may also be esterified by reacting with an alcohol in the presence of a condensation promoting reagent such as a carbodiimide, for example dicyclohexylcarbodiimide, or the chemical equivalent thereof. Such reactions may be carried out under conditions similar to those hereinbefore described for the same type of reaction carried out on an acid addition salt of a compound of the formula (II).

The present invention also provides a process for the preparation of a compound of the formula (XI) or a salt thereof which process comprises the reaction of a compound of the formula (II), or a salt thereof, as hereinbefore defined with a compound of the formula (XII):

$$Y-CO-O-R_7 \qquad \text{(XII)}$$

wherein $R_7$ is as defined in relation to formula (X) and Y is a readily displaceable group.

Favoured groups Y include the chlorine atom and chemically equivalent atoms or groups such as the bromine atom or a $OR_7$ group or the like.

A preferred compound of the formula (XII) is benzylchloroformate.

The reaction may be performed under conventional acylation conditions, for example in non-acylatable organic solvent such as acetone in the presence of an acid acceptor such as lithium bicarbonate, sodium carbonate, potassium carbonate or the like at a non-extreme temperature such as 10° to 30° C., for example at about 0° to 10° C.

We have found it convenient to carry out the acylation on a salt of the compound of the formula (II) such as an alkali metal salt and in particular the lithium salt.

From the preceding descriptions it will be realised that from a broad process aspect the present invention provides a process for the preparation of a compound of the formula (II) as hereinbefore defined or an ester thereof which process comprises the hydrogenation of a compound of the formula (X) as hereinbefore defined or an ester thereof; and thereafter if desired esterifying the zwitterion of the formula (IIa) as hereinbefore defined which was produced by the hydrogenation of the compound of the formula (II) or a hydrogenolysable ester thereof; or thereafter if desired acylating the zwitterion of the formula (IIa) as hereinbefore defined which was produced by the hydrogenation of the compound of the formula (X) or a hydrogenolysable ester thereof with a compound of the formula (XII) as hereinbefore defined to form a compound of the formula (XI) as hereinbefore defined and thereafter esterifying the resulting compound of the formula (XI) or a salt thereof and subjecting the thus formed ester to hydrogenation to yield the desired ester of a compound of the formula (II).

Since the compounds of the formula (XI) and the salts and ester thereof are as use as intermediates they form part of this invention. Suitably the compounds of the formula (XI) are in the form of an ester of a type hereinbefore described. Suitably the compounds of the formula (XI) are in the form of a salt such as in alkali metal salt, for example the lithium salt.

We have chosen to name the novel compounds of this invention as notional derivatives of deoxyclavulani acid which is of the formula (XIII):

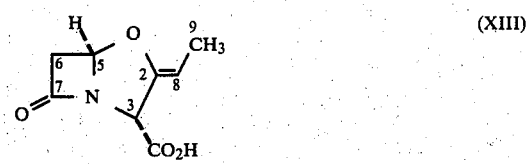

Thus on this system the amino-substituent is defined as being attached to the 9-carbon atom.

The processes of this invention may be adapted to the preparation of the following compounds:
9-N-Benzylaminodeoxyclavulanic acid
9-N-(2-Methoxybenzyl)aminodeoxyclavulanic acid
9-N-(3-Methoxybenzyl)aminodeoxyclavulanic acid
9-N-(4-Methoxybenzyl)aminodeoxyclavulanic acid
9-N-(4-Hydroxybenzyl)aminodeoxyclavulanic acid
9-N-(3-Hydroxybenzyl)aminodeoxyclavulanic acid
9-N-(4-Hydroxy-3-methoxybenzyl)aminodeoxyclavulanic acid
9-N-(3-Hydroxy-4-methoxybenzyl)aminodeoxyclavulanic acid
9-N-(2-Fluorobenzyl)aminodeoxyclavulanic acid
9-N-(3-Fluorobenzyl)aminodeoxyclavulanic acid
9-N-(4-Fluorobenzyl)aminodeoxyclavulanic acid
9-N-(2-Methylbenzyl)aminodeoxyclavulanic acid
9-N-(3-Methylbenzyl)aminodeoxyclavulanic acid
9-N-(4-Methylbenzyl)aminodeoxyclavulanic acid
9-N-(2-Acetamidobenzyl)aminodeoxyclavulanic acid
9-N-(3-Acetamidobenzyl)aminodeoxyclavulanic acid
9-N-(4-Acetamidobenzyl)aminodeoxyclavulanic acid
9-N-(4-Propionamidobenzyl)aminodeoxyclavulanic acid
9-N-(4-Chlorobenzyl)aminodeoxyclavulanic acid
9-N-(2-Hydroxyethyl)aminodeoxyclavulanic acid
9-N-Ethylaminodeoxyclavulanic acid
9-N-(2-Hydroxypropyl)aminodeoxyclavulanic acid
9-N-Propylaminodeoxyclavulanic acid The present invention also provides esters of the preceding compounds which esters may be in the form of acid addition salts. Suitable esters include:
methyl
ethyl
methoxymethyl
benzoylmethyl
acetylmethyl
benzyl
4-methoxybenzyl
2-hydroxyethyl
carboxymethyl Suitable acid addition salts are normally and preferably those with pharmaceutically acceptable acids.

It has now been discovered that the compounds of the formula (II) may also be prepared by the catalytic removal of substituted allyl groups from compounds analogous to those of formula (I) in which the $CH_2X_2$ moiety is replaced by a substituted allyl group. This process can improve yields of product and can be more convenient in that quicker reaction times and lower pressures of hydrogen may be employed.

Therefore the present invention also provides a process for the preparation of a compound of the formula (II) as hereinbefore defined or an ester thereof which process comprises the hydrogenation of a compound of the formula (XIV):

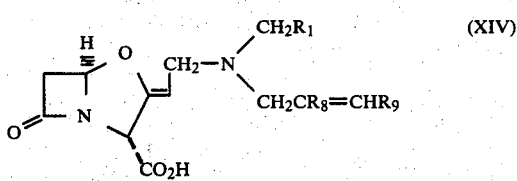

or ester thereof, wherein $R_1$ is as hereinbefore defined; and wherein $R_8$ is a hydrogen atom or lower alkyl group, $R_9$ is a hydrogen atom, a lower alkyl group, or a phenyl group optionally substituted with an inert organic group such as lower alkyl or lower alkoxy; or wherein $R_8$ and $R_9$ together represent a butadiene moiety; and thereafter if desired esterifying the zwitterion of the formula (IIa) as hereinbefore defined which was produced by the hydrogenation of the compound of the formula (XIV) or a hydrogenolysable ester thereof.

When used herein the term "hydrogenolysable ester" means an ester which on hydrogenation is cleaved to yield the parent carboxylic acid.

When used herein the term "lower-alkyl" means an alkyl group with 1-4 carbon atoms. Thus examples of suitable alkyl groups are methyl, ethyl, n-propyl, iso-propyl, n-butyl, sec-butyl and iso-butyl.

Particularly suitable groups $CH_2CR_8=CHR_9$ for use in the compounds of formula (XIV) include the following, $CH_2CH=CHCH_3$, $CH_2CH=CHC_6H_5$, $CH_2C(CH_3)=CH_2$ $CH_2C(C_2H_5)=CH_2$, $CH_2(nC_3H_7)=CH_2$, $CH_2C(CH_3)=CHCH_3$, $CH_2C(CH_3)=C(CH_3)_2$, $CH_2C(CH_3)=CHC_2H_5$, $CH_2C(CH_3)=CHC_6H_5$ and $CH_2C_6H_5$.

Favoured groups $CH_2CR_8=CHR_9$ are $CH_2CH=CHCH_3$, $CH_2CH=CHC_6H_5$, $CH_2C(CH_3)=CH_2$, $CH_2C(CH_3)=CHC_6H_5$ and $CH_2C_6H_5$.

Particularly preferred groups $CH_2CR_8=CHR_9$ are $CH_2C(CH_3)=CH_2$, $CH_2C(CH_3)=CHC_6H_5$ and $CH_2C_6H_5$.

A process according to this invention comprises the preceding hydrogenation when $CH_2CR_8CHR_9$ is a $CH_2C_6H_5$ group.

The hydrogenation is normally carried out in the presence of a transition metal catalyst.

The catalyst we have preferred to use is palladium, for example in the form of palladium on carbon (charcoal), palladium on barium sulphate, palladium on calcium carbonate, palladium black or the like.

A favoured catalyst is palladium on carbon (sometimes referred to as palladium on charcoal); for example 5%, 10%, 20% or 30% palladium on carbon. The high palladium content catalysts are particularly apt as smaller total weights of catalyst can be employed thereby avoiding possible problems associated with adsorption of product onto the carbon.

A low, medium or high pressure of hydrogen may be used in this reaction, for example from 1 to 6 atmospheres. In general if the catalyst used contains a lower percentage of palladium (for example 5% or 10% palladium) then better yields of the desired product are obtained using a pressure of about 3 to 5 atmospheres of hydrogen, for example about 4 atmospheres of hydrogen. In general if the catalyst used contains a higher percentage of palladium (for example 20% or 30% palladium) then acceptable yields of the desired product may also be obtained at low and medium pressures of hydrogen, for example about 1 to 2 atmospheres of hydrogen. We have found it convenient to use an atmospheric or slightly superatmospheric pressure of hydrogen in conjunction with higher palladium content catalysts.

The reaction is normally carried out at a non-extreme temperature, for example from 0° C. to 30° C. and more usually from 12° C. to 25° C. It is generally convenient to carry out the reaction at ambient temperature.

Suitable solvents for carrying out the hydrogenation include ethanol, n-propanol, isopropanol, tetrahydrofuran, dioxane, ethyl acetate or mixtures of such solvents or such solvents in the presence of water. A favoured solvent is aqueous tetrahydrofuran. Further favoured solvents are ethanol or a mixture of isopropanol, tetrahydrofuran and water.

We have preferred to carry out the hydrogenation reaction on a hydrogenolysable ester of a compound of the formula (XIV) so that a compound of the formula (II) per se is formed by the hydrogenation. Such hydrogenation reaction proceeds at least in part via the formation of a compound of the formula (XIV). Favoured hydrogenolysable esters include benzyl and substituted benzyl esters. The nature of the substituent employed is unimportant as long as it does not interfere with the hydrogenolytic cleavage. Thus suitable substituents include lower alkyl, lower alkoxyl, lower acyloxyl, lower acyl, nitro, cyano, carboxylic acid groups or salts or lower alkyl esters or amides thereof, nitro, halo or similar substituents. Apt substituents include methyl, methoxyl, nitro, chloro, bromo and the like. One, two or three such substituents may be employed (except not more than one nitro group should be present).

Favoured esters include the benzyl, nitrobenzyl bromobenzyl, chlorobenzyl, methylbenzyl and methoxybenzyl esters. Particularly favoured esters include the benzyl, p-nitrobenzyl and p-methoxybenzyl esters. The preferred ester is the benzyl ester.

Further favoured hydrogenolysable ester groups include those groups $CH_2CR_8\!=\!CHR_9$ that have been specified hereinbefore as being favoured for removal from a nitrogen atom by hydrogenolysis.

If the hydrogenation is performed on non-hydrogenolysable esters of the compound of the formula (XIV) then naturally an ester of the compound of the formula (II) results.

The product may generally be isolated from the reaction mixture by filtering off the solids (the catalyst, which should be well washed to remove the product) and then evaporating the solvent, preferably under low pressure, to yield the initial product. Further purification may be effected by such conventional methods as chromatography over cellulose or other mild stationary phase eluting with a $C_{1-4}$ alkanol optionally in the presence of water and optionally in the presence of tetrahydrofuran. Evaporation of the combined active fraction (identified by aqueous potassium permanganate spray on tlc) then yields the desired compound in pure form. The desired product is normally obtained in crystalline form (unless it is an unsalted ester). Trituration under ethanol, isopropanol or the like $C_{1-4}$ alkanol or other conventional solvent such as a ketone, ether or ester solvent or other conventional solvent (for example of up to 6 carbon atoms and more suitably of up to 4 carbon atoms) may also be used to aid crystallisation. Recrystallisation from ethanol or the like may also be employed. The solvent used in such processes may advantageously be moist. The preceding work up procedures successfully separate the desired compound from other products of the hydrogenation such as the disecondarybutylamine derivative.

Zwitterionic compounds, such as those of the formula (II) may be obtained from high yielding reactions by the addition of $C_{1-4}$ alkanol such as cold ethanol or the like to the initial product.

The initial product of the lower yielding reactions may contain considerable impurities so that it may be advantageous to wash the initial product by dissolving in a water immiscible organic solvent and extracting into water. Evaporation of the aqueous phase, preferably under a good vacuum, then yields a purer product which may be further purified if desired as previously described.

Unsalted esters of the compounds of the formula (II) tend to be oils so that it is often more convenient for handling to convert them into solid acid addition salts, for example by reaction with one equivalent of an acid. Alternatively the non-hydrogenolysable ester of the compound of the formula (XIV) may be hydrogenated in the presence of one equivalent of an acid, that is they may be hydrogenated in the form of their acid addition salt.

The compounds of the formula (II) may be hydrogenated in the form of their acid addition salts with a strong acid but this is not a preferred form of the process of this invention.

The present invention also provides a process for the preparation of an ester of a compound of the formula (II) which process comprises the reaction of the compound of the formula (II) with an esterifying agent.

The zwitterionic compound of the formula (II) may be dissolved or suspended in a solvent such as dimethylformamide, hexamethylphosphoramide, dichloromethane, ethyl acetate or other non-esterifiable solvents and therein esterified. Suitable temperatures for such a reaction range from about 0° to about 25° C. Suitable esterifying reagents include reactive halides and their equivalents, alkyl oxonium salts and the like.

When a reagent such as reactive iodide, chloride, bromide, tosylate, mesylate or the equivalent is used, the resulting salt is generally suitable for use in a composition of this invention. Alternatively, the salt may be converted to a free base or alternative salt. When an alkyl oxonium salt is used, it is preferred to convert the resulting tetrafluoroborate to the free base or alternative salt. The various afore-mentioned salts may be converted to the free base by neutralisation, for example by contacting a solution of the salt in water with an organic phase, neutralising the salt by adding a base and extracting the liberated amine into the organic phase. This amine may thereafter be re-salted by reacting with an appropriate acid, for example in a dry organic solvent. It is generally preferred to use not more than one equivalent of acid for this process. Alternatively, the originally formed salt may be converted into the alternative salt using an ion exchange material for example, by passing an aqueous solution of one salt through a bed of an anion exchange resin in the form of the form of the desired salt such as the chloride form.

The salts may normally be obtained in solid form by dissolving in a fairly polar organic solvent (such as ethanol, tetrahydrofuran or the like) and then precipitating using a non-polar solvent such as diethyl ether, cyclohexane or the like.

The salts of the esters of the compounds of the formula (II) may normally be obtained in crystalline form by conventional methods such as trituration under (or crystallisation or recrystallisation from) a suitable organic solvent such as ether, acetone, acetonitrile, tetrahydrofuran or the like.

The present invention also provides a process for the preparation of an ester of the compound of the formula (II) which process comprises the reaction of an acid addition salt of the compound of the formula (II) with an alcohol in the presence of a condensation promoting agent.

Suitable condensation promoting agents for use in this process include carbodiimides such as dicyclohexylcarboxiimide and the chemical equivalents thereof.

The acid addition salt may be formed in situ or may be preformed. The acid employed will normally be a strong acid such as a methane sulphonic acid, p-toluene sulphonic or the like or trifluoroacetic acid or the like.

The reaction is normally carried out in an inert organic solvent. When the ester being formed is that of a liquid alcohol it is convenient to use that alcohol as the solvent or as part of the solvent system. The esterification is generally performed at a non-extreme temperature such as 0° to 35° C., for example from about 10° to 25° C. Conveniently the reaction may be performed at ambient temperature.

Since the compound of the formula (XIV) and its salts and esters are of use as intermediates they form part of this invention. Suitably the compounds of the formula (XIV) are in the form of an ester of a type hereinbefore described. Suitably the compounds of the formula (XIV) are in the form of a salt such as in alkali metal salt, for example the lithium salt.

The intermediates of the formula (XIV) and its salts and esters may be prepared by the methods of U.S. Ser. No. 731928, and divisional application Ser. No. 942,156 now U.S. Pat. No. 4,256,638.

The following Descriptions illustrate the processes used to prepare intermediates. The secondary amines used to displace acyloxyl groups from the acylated clavulanic acid derivatives may be prepared by the hydrogenation of a Schiffs base prepared by the reaction of an aldehyde and primary amine in conventional manner. The following Demonstrations illustrate the activities of the compounds of this invention. The following Examples illustrate the invention.

Description 1

Benzyl 9-(N-benzyl-N-2-hydroxyethyl)aminodeoxyclavulanate

Clavudiene benzyl ester (0.5 g) in acetonitrile (10 ml) was cooled to 0° C., N-benzyl-2-hydroxyethylamine (0.36 g) was added and the reaction mixture stirred for 2½ hours. Ethyl acetate (100 ml) was added and the mixture evaporated to low volume. The residue was subjected to column chromatography using ethyl acetate as eluent. The product, isolated in low yield, had an ir spectrum (liquid film) as follows: 3400 (Broad, —OH), 1800 ($\beta$-lactam C=O), 1740 (ester C=O), 1700 (C=C), 1695 cm$^{-1}$ (aromatic protons).

Description 2 p-Methoxybenzyl 9-(N-benzyl-N-2-hydroxyethyl)amino-deoxyclavulanate p-Methoxybenzyl trichloroacetylclavulanate (5.37 mM) in dry dimethylformamide (75 cm$^3$) at −10° C. was treated with N-benzyl-N-2-hydroxyethylamine (1.55 cm$^3$) and stirred at this temperature for 5 hours. The mixture was poured into ethyl acetate (150 cm$^3$) and washed with water (3×100 cm$^3$), dried and evaporated to an oil (0.38 g) Rf (SiO$_2$/ethyl acetate:cyclohexane; 1:1)=0.13 $\nu$(film) 3400, 1810, 1750, 1620 cm$^{-1}$.

Description 3

Benzyl 9-(N-benzyl-N-ethyl)aminodeoxyclavulanate

Benzyl trichloroacetylclavulanate (9.2 mM) in dry dimethylformamide (30 cm$^3$) at −60° C. was treated with N-benzylethylamine (2.74 cm$^3$) and stirred for 3½ hours at this temperature. The mixture was poured into ethyl acetate (150 cm$^3$) and washed with water (3×100 cm$^3$), dried and evaporated in vacuo to yield an oil (4.43 g). Rf (SiO$_2$/ethyl acetate:cyclohexane; 1:1) 0.3 $\nu$(film) 1804, 1750 cm$^{-1}$.

Description 4

Benzyl 9-(N-benzyl-N-isopropyl)aminodeoxyclavulanate

Clavudiene benzyl ester (0.5 g) in acetonitrile (10 ml) was cooled in ice-water. N-isopropylbenzylamine (0.39 g, 1.3 moles) was added with stirring. The reaction mixture was allowed to warm to room temperature and stirred for 3 hours. Ethyl acetate (100 ml) was added, and the solution evaporated to low bulk in vacuo. The residue was subjected to column chromatography on silica gel using cyclohexane and ethyl acetate as eluents. The product was eluted after the unreacted diene.

Description 5

Benzyl 9-(N,N-dibenzyl)aminodeoxyclavulanate

Benzyl dichloroacetyl-clavulanate (0.8 g) was dissolved in dry dimethylformamide and cooled to 0° C., treated with dibenzylamine (768 μl; 0.004 mol) in dry dimethylformamide (4 ml) over 15 minutes, the temperature being maintained at 0° C. The resulting yellow solution was stirred at 0° C. for 2½ hours and at room temperature for 4 hours. Ethylacetate was added (100 ml) and the solution washed with water (3×25 ml), dried and evaporated. The oil was purified by fast gradient elution on silica gel using ethyl acetate/cyclohexane as the eluting solvent (Yield 0.33 g). Rf (SiO$_2$/ethylacetate:cyclohexane; 1:1)=0.76. $\nu$(film) 1810, 1755, 1700; δ(CDCl₃) 2.80 (1H, d, J 16 Hz, 6β—CH) 3.05 (2H, d, J 7 Hz, 9—CH₂), 3.17-3.37 (1H, m, 6α—CH) 3.32 (4H, s, 2×NCH₂C₆H₅), 4.59 (1H, t, J 7 Hz, 8—CH), 4.90 (1H, s, 3—CH), 5.03 (2H, s, OCH₂C₆H₅) 5.57 (1H, d, J 3 Hz, 5α—CH), 7.20 (15H, s, 3×C₆H₅).

Description 6

Benzyl 9-(N,N-dibenzyl)aminodeoxyclavulanate

Clavudiene benzyl ester (271 mg) in dry acetonitrile (4 ml) at 0° C. was treated with dibenzylamine (197 mg) in dry acetonitrile (2 ml) over 5 minutes. The reaction mixture was stirred at 0° C. for 2 hours and at room temperature for 2 hours. The solvent was removed by evaporation and the residue dissolved in ethyl acetate, washed with water, dried, evaporated and fractionated on silica-gel to yield the desired product which was purified by chromatography.

Description 7

Benzyl 9-[N-benzyl-N-(dl-2-hydroxypropyl)]aminodeoxyclavulanate

Benzyl dichloroacetylclavulanate (0.8 g) in dry dimethylformamide (20 ml) was cooled to 0° C. and a solution of dl-1-benzylamino-propan-2-ol (0.65 g) in dry dimethylformamide was added slowly. Stirring was continued for 4 hours at 0° C. A more polar component was formed (thin layer chromatograph) and worked up as described in description 5 and chromatographed to give the desired product (0.16 g).

Description 8

Benzyl 9-[N-benzyl-N-(dl-2-hydroxypropyl)]aminodeoxyclavulanate

Benzyl trichloroacetylclavulanate (2.5 g; 5.8 mm) in dry dimethyl-formamide (50 cm³) at −10° was treated with N-benzyl-N-(dl-2-hydroxypropyl)amine (1.9 equivalents) in dimethylformamide (20 cm³) dropwise. The reaction mixture was stirred at −10° for 4½ hours, poured onto cold (0°) ethylacetate and the organic layer washed with water (5×75 cm³). After drying, the ethyl acetate solution was passed through a ½ cm×2½ cm dia. column of silica gel eluting with ethyl acetate (75 cm³) until the eluate was no longer coloured. The ethyl acetate solution was extracted with dilute acetate acid (3×50 cm³), the aqueous extracts were combined and treated with sodium bicarbonate in the presence of fresh ethyl acetate (80 cm³) with vigourous stirring until the pH of the aqueous phase was 8. The ethyl acetate phase was dried and evaporated in vacuo to yield product as a yellow oil (700 mg); Rf (SiO₂/ethylacetate:cyclohexane; 1:1)=0.28, detection by aqueous potassium permanganate spray; ν$_{max}$ (KBr) 3410 (broad), 1795, 1740, 1700 cm⁻¹; δ[(CD₃)₂CO] 0.98 (3H, d, J 6 Hz, CHCH₃), 2.28, 2.30 (2H, 2×d, J 6 Hz, NCH₂—CH(OH)), 2.91, 2.94 (1H, 2×d, J 17 Hz, 6β—CH), 3.15 (2H, d, J 7 Hz, 9—CH₂), 3.2-3.9 (5H, m, NCH₂C₆H₅, —CH₂CH(OH)CH₃, 6α—CH, CHOH), 4.72 (1H, t, J 7 Hz, 8—CH), 5.06 (1H, s, 3—CH).

Description 9

Benzyl 9-N-benzyl-N-(4-methoxybenzyl)aminodeoxyclavulanate

Benzyl dichloroacetylclavulanate (4.8 g; 12 mM) in dimethylformamide (50 ml) at 0° was treated with N-benzyl-N-4-methoxybenzylamine (5.2 g; 1.9 equivalents) dropwise. The reaction mixture was stirred at 0° for 1 hour and then at 20° for 5 hours. The reaction mixture was then poured into cold (0°) ethyl acetate and the organic layer washed with water (3×75 ml) and saturated brine (5×75 ml). The ethyl acetate phase was dried and evaporated in vacuo to yield 6.6 g of a coloured oil. This oil was chromatographed on silica gel, eluting with ethyl acetate-cyclohexane; 1:1. Fractions containing the title compound were collected and evaporated in vacuo to yield benzyl 9-[N-benzyl-N-(4-methoxybenzyl)amino]deoxyclavulanate (2.24 g) as a colourless oil. Rf (SiO₂/ethyl acetate:cyclohexane; 1:1)=0.70.

ν(film) 1805, 1750, 1690, 1610, 1510, 1300, 1250, 1175, 740, 700 cm⁻¹.

δ(CDCl₃) 2.87 (1H, d, J 17 Hz, 6βCH), 3.10 (2H, d, J 7 Hz, 9CH₂), 3.33 (1H, dd, J 17 Hz and 3 Hz, 6αCH), 3.38, 3.43 (4H, 2×s, NCH₂C₆H₅ and NCH₂C₆H₄OCH₃), 3.70 (3H, s, OCH₃), 4.71 (1H, t, J 7 Hz, 8CH), 5.00 (1H, s, 3CH), 5.10 (2H, s, OCH₂C₆H₅), 5.51 (1H, d, J 3 Hz, 5αCH), 6.75 (2H, d, J 8 Hz, aromatic, ortho to methoxyl), 7.09-7.20 (12H, m, aromatic meta to methoxy and 2×C₆H₅).

Description 10

Benzyl 9-[N-benzyl-N-(4-fluorobenzyl)]aminodeoxyclavulanate

Benzyl dichloroacetylclavulanate (8.5 g; 21 mM) in dimethylformamide (75 cm³) at 0° was treated dropwise with N-benzyl-N-4-fluorobenzylamine (8.1 g; 1.9 equivalents). The reaction mixture was stirred at 0° for 1 hour and 5 hours at 20°. The reaction mixture was poured into cold (0°) ethyl acetate (150 cm³) and the organic layer was then washed with water (3×75 cm³) and saturated brine (4×75 cm³). The ethyl acetate phase was dried and evaporated in vacuo to yield 10 g of a coloured oil. 3 g of this crude product was chromatographed on silica gel, eluting with ethyl acetate-cyclohexane; 1:1. Fractions containing the title compound were collected and evaporated in vacuo to yield benzyl 9-[N-benzyl-N-(4-fluorobenzyl)]aminodeoxyclavulanate (1 g) as a colourless oil. Rf (SiO₂/ethyl acetate:cyclohexane; 1:1)=0.70, detection by potassium permanganate spray.

ν(film) 180, 1750, 1690, 1508, 1305, 1220, 820, 740, 700 cm⁻¹. δ(CDCl₃) 2.90 (1H, d, J 17 Hz, 6βCH), 3.09 (2H, d, J 7 Hz, 9CH₂), 3.38 (1H, dd, J 17 Hz and 3 Hz, 6αCH), 3.39, 3.42 (4H, 2×s, NCH₂—C₆H₅ and NCH₂C₆H₄F), 4.70 (1H, t, J 7 Hz, 8CH), 5.02 (1H, s, 3—CH), 5.12 (2H, s, OCH₂C₆H₅), 5.54 (1H, d, J 3 Hz, 5αCH), 6.80-7.25 (14H, m, 2×CH₃C₆H₅, and CH₂C₆H₄F).

Description 11

Benzyl 9-[N-benzyl-N-(4-methylbenzyl)]aminodeoxyclavulanate

Benzyl dichloroacetylclavulanate (8.5 g; 21 mM) in dimethylformamide (75 cm³) at 0° was treated with N-benzyl-N-(4-methylbenzyl)amine (8.40 g; 1.9 equivalents), dropwise and then stirred for 1 hour at 0° and 3 hours at 20°. The reaction mixture was poured into cold (0°) ethyl acetate (150 cm³) and the organic phase washed with water (3×75 cm³) and saturated brine (4×75 cm³). The ethyl acetate phase was dried and evaporated in vacuo to yield 11 g of a coloured oil. 1 g of this crude product was chromatographed on silica gel, eluting with ethyl acetate:cyclohexane, 1:1. Fractions containing the title compound were collected and were evaporated in vacuo to yield 250 mg (25%) of a colourless oil; Rf (SiO₂/ethyl acetate:cyclohexane; 1:1)=0.70; detection by aqueous potassium permanganate spray.

Further fractions containing the title compound in approximately 80% purity were collected, yield=0.6 g.

$\nu$(film) of purest product: 1805, 1750, 1690, 1510, 1495, 1450, 1300, 1230, 1175, 1120, 1080, 1040, 1020, 965, 890, 800, 740, 700 cm$^{-1}$.

$\delta$(CDCl₃) 2.28 (3H, s, -C₆H₄C$\underline{H}$₃), 2.88 (1H, d, J 17 Hz, 6$\beta$C$\underline{H}$), 3.10 (2H, d, J 7 Hz, 9C$\underline{H}$₂), 3.35 (1H, dd, J 17 Hz and 3Hz, 6$\alpha$C$\underline{H}$), 3.42 (4H, s, NC$\underline{H}$₂C₆H₅ and NC$\underline{H}$₂C₆H₄CH₃), 4.71 (1H, t, J 7 Hz, 8C$\underline{H}$), 5.00 (1H, s, 3C$\underline{H}$), 5.10 (2H, s, OC$\underline{H}$₂C₆H₅), 5.52 (1H, d, J 3 Hz, 5$\alpha$C$\underline{H}$), 6.95–7.27 (14H, m, 2×CH₂C₆$\underline{H}$₅ and C$\underline{H}$₂C₆$\underline{H}$₄CH₃).

Description 12

Benzyl 9-[N-benzyl-N(4-benzoxy-3-methoxybenzyl)benzyl]aminodeoxyclavulanate.

Benzyl dichloroacetyl-clavulanate (1.9 g; 4.7 mM) in dry dimethylformamide (50 cm³) at 0° C. was treated with N-benzyl-N-(4-benzoxy-3-methoxybenzyl)amine (3 g; 1.9 equivalents) dropwise. The reaction mixture was stirred at 0° C. for 1 hour then at 20° C. for 5 hours. The reaction mixture was then poured into cold (0°) ethyl acetate and the organic layer washed with water (3×75 cm³) and saturated brine (5×75 cm³). The ethyl acetate phase was dried and evaporated in vacuo to yield a coloured oil. This oil was chromatographed on silica gel, eluting with ethyl acetate-cyclohexane; 1:1. Fractions were collected containing the title compound; these were evaporated in vacuo to yield benzyl 9-[N-benzyl-N-(4-benzoxy-3-methoxybenzyl)-]aminodeoxyclavulanate (0.1 g) as a colourless oil.

Rf (SiO₂/ethyl acetate:cyclohexane; 1:1)=0.70.

$\nu$(film) 1800, 1750, 1675, 1590, 1510, 1450, 1380, 1300, 1260, 1225, 1160, 1140, 1080, 1015, 805, 740, 700 cm$^{-1}$.

$\delta$(CDCl₃) 2.90 (1H, d, J 17 Hz, 6$\beta$C$\underline{H}$), 3.03 (2H, d, J 7 Hz, 9C$\underline{H}$₂), 3.37 (1H, dd, J 17 and 3 Hz, 6$\alpha$C$\underline{H}$), 3.37, 3.42 (6H, 2×s, NC$\underline{H}$₂C₆H₅ and NC$\underline{H}$₂C₆H₃ OC$\underline{H}$₃, OCH₂C₆H₅), 3.80 (3H, s, OCH₃), 4.72 (1H, t, J 7 Hz, 8C$\underline{H}$), 5.01 (1H, s, 3C$\underline{H}$), 5.54 (1H, d, J 3 Hz, 5$\alpha$C$\underline{H}$), 6.70–7.34 (18H, m, 3×CH₂C₆$\underline{H}$₅ and 2 protons ortho to the CH₂ of CH₂(C₆H₃)(OCH₃)OCH₂C₆H₅.

Description 13

Benzyl 9-[N-(4-benzyloxybenzyl)-N-benzyl]aminodeoxyclavulanate

Benzyl dichloroacetylcalvulanate (7.2 g; 18 mm), in dry dimethylformamide (75 cm³) at 0° was treated with N-(4-benzoxybenzyl)-N-benzylamine (1.9 equivalents) and stirred at 0° for 3 hours, then poured into ethyl acetate (150 cm³) and washed with water (5×50 cm³) and brine (3×50 cm³), dried (anhydrous magnesium sulphate) and evaporated in vacuo to yield a coloured oil. This oil was chromatographed on silica eluting with ethylacetate/cyclohexane; 1:1. Fractions were collected containing the title compound (detection by aqueous potassium permanganate spray), RF (SiO₂ ethylacetate/cyclohexane; 1:1)=0.81. Combined fractions were evaporated to an oil, yield of approximately 70% pure material=2.7 g, pure fractions were collected for spectroscopy. $\nu$(film) 1800, 1745, 1690, 1600, 1595, 1510, 1450, 1380, 1300, 1230, 1170, 1129, 1080, 1945, 1020, 830, 740, 700 cm$^{-1}$; $\delta$(CDCl₃) 2.87 (1H, d, J 17 Hz, 6$\beta$C$\underline{H}$), 3.09 (2H, d, J 7 Hz 9C$\underline{H}$₂), 3.33 (2H, dd, J 17 Hz and 3 Hz, 6$\alpha$C$\underline{H}$), 3.37, 3.42 (4H, 2×s, NC$\underline{H}$₂C₆H₅ and NC$\underline{H}$₂C₆H₄OCH₂C₆H₅), 4.70 (1H, t, J 7 Hz, 8C$\underline{H}$), 4.97 (3H, broad S, C₆H₄OC$\underline{H}$₂C₆H₅ and 3C$\underline{H}$), 5.10 (2H, S, CO₂CH₂C₆H₅), 5.51 (1H, d, J 3 Hz, 5$\alpha$—C$\underline{H}$), 6.80 (2H, d, J 9 Hz aromatic protons ortho to benzyloxy), 7.0–7.30 (17 H, m, N—CH₂C₆$\underline{H}$₅, OCH₂C₆$\underline{H}$₅, CO₂CH₂C₆$\underline{H}$₅, aromatic protons meta to benzyloxy).

Description 14

Benzyl 9-[(N-3,4-dimethoxybenzyl)-N-benzylamino]deoxyclavulanate

Benzyl dichloroacetylclavulanate (6.56 g; 16 mm) in dry dimethylformamide (50 cm³) at 0° was treated with N-(3,4-dimethoxybenzyl)-N-benzylamine (8 g; 1.9 equivalents) in 30 cm³ dimethylformamide and stirred for 2 hours at 0° then 2 hours at 10°. Then poured into cold ethyl acetate (150 cm³) and washed with water (5×50 cm³) and saturated brine (5×50 cm³), dried (anhydrous magnesium sulphate) and evaporated in vacuo to yield an oil; 10.1 g. 1.2 g of this crude product was chromatographed on silica gel eluting with ethylacetate/cyclohexane; 1:1. Fractions were collected containing the title compound.

Rf=0.74 (SiO₂/ethylacetate:cyclohexane; 1:1), detection by aqueous potassium permanganate spray. Combined fractions were evaporated in vacuo to yield an oil; 0.35 g. $\nu$(film) 1804, 1750, 1690, 1510, 1480, 1305, 1260, 1235, 1175, 1155, 1145, 1120, 1030, 1015, 807, 740, 700 cm$^{-1}$.

$\delta$(CDCl₃) 2.91 (1H, d, J 17 Hz, 6$\beta$C$\underline{H}$), 3.12 (2H, d, J 7 Hz, 9C$\underline{H}$₂), 3.38 (1H, dd, J 17 Hz and 3 Hz, 6$\alpha$—CH), 3.39, 3.43 (4H, 2×s, 2×NCH₂), 3.83 (6H, S, 2×OCH₃), 4.73 (1H, dt, J 7 Hz and <1 Hz, 8C$\underline{H}$), 5.01 (1H, d, J <1 Hz, 3C$\underline{H}$), 5.12 (2H, S, OCH₂C₆H₅), 5.55 (1H, d, J 3 Hz, 5$\alpha$—C$\underline{H}$), 6.73–6.83 (3H, m, aromatic protons ortho to CH₂), 7.23 (10H, m, 2×C₆H₅).

Description 15

Benzyl 9-[N-(4-acetylaminobenzyl)-N-benzyl]aminodeoxyclavulanate

Benzyl dichloroacetylclavulanate (4.4 g; 11 mm) in dry dimethylformamide (50 cm³) at 0° was treated with N-(4-acetamidobenzyl)benzylamine (5.3 g; 1.9 equivalents) dropwise in 20 cm³ dimethylformamide with stirring. Stirring was continued for 4 hours at 0° then poured into ethyl acetate (200 cm³) and washed with water (5×50 cm³) and brine (3×50 cm³), dried (anhydrous magnesium sulphate) and evaporated to a foam. This crude product was chromatographed on silica eluting with ethylacetate-cyclohexane; 1:1 graduating to neat ethylacetate. Fractions were collected containing the title compound (detection by aqueous potassium permanganate spray). Rf (SiO₂/ethylacetate-cyclohexane; 1:1)=0.30. Combined fractions were evaporated in vacuo to give a crisp foam, 2.51 g. $\nu$(Nujol Mull) 3300, 1800, 1745, 1690, 1665, 1600, 1530, 1510, 1450, 1410, 1370, 1310, 1260, 1170, 1120, 1040, 1015, 740, 700 cm$^{-1}$.

δ(CDCl$_3$) 2.10 (1H, S, C$\underline{H}_3$CONH), 2.91 (1H, d, J 17 Hz, 6βC$\underline{H}$), 3.10 (2H, d, J ∂Hz, 9C$\underline{H}_2$), 3.37 (1H, dd, J 17 and 3 Hz, 6αC$\underline{H}$), 3.40, 3.43 (4H, 2×s, 2×NC$\underline{H}_2$), 4.69 (1H, t, J 7Hz, 8C$\underline{H}$), 4.98 (1H, s, 3C$\underline{H}$), 5.11 (2H, s, CO$_2$C$\underline{H}_2$C$_6$H$_5$), 5.33 (1H, d, J 3Hz, 5αC$\underline{H}$), 7.12-7.41 (15H, m, 2×C$_6\underline{H}_5$, CH$_2$C$_6\underline{H}_4$—p—NHCOCH$_3$, CON$\underline{H}$).

Description 16

Benzyl 9-[N-(2-fluorobenzyl)-N-benzyl]aminodeoxyclavulanate

Benzyl dichloroacetylclavulanate (8 g; 0.02 M) in dry dimethylformamide (100 cm$^3$) at 0° was treated with N-(2-fluorobenyl)benzylamine (1.9 equivalents) dropwise in dimethylformamide (30 cm$^3$) and stirred for 4 hours at 0° then 2 hours at 20°. The mixture was poured into ethylacetate (200 cm$^3$) and washed with water (4×50 cm$^3$) and saturated brine (5×50 cm$^3$) dried (anhydrous magnesium sulphate) and evaporated to an oil, yield=10 g. 2 g of this crude product was chromatographed on silica eluting with ethylacetate/cyclohexane (1:2). Fractions were collected containing the title compound, Rf (SiO$_2$/ethylacetate-cyclohexane; 1:1)=0.78 (detection by aqueous potassium permanganate spray). Combined fractions were evaporated in vacuo to yield an oil, yield=0.4 g. ν(film) 1800, 1745, 1690, 1490, 1450, 1305, 1230, 1180, 1120, 1045, 1020, 760, 700 cm$^{-1}$. δ(CDCl$_3$) 2.94 (1H, d, J 17 HZ, 6βCH), 3.13 (2H, d, J 7 HZ, 9C$\underline{H}_2$), 3.41 (1H, dd, J 17 and 3 HZ, 6αC$\underline{H}$), 3.50, 3.55 (4H, 2×s, 2×NC$\underline{H}_2$), 4.75 (1H, t, J 7 HZ, 8C$\underline{H}$), 5.02 (1H, s, 3C$\underline{H}$), 5.14 (2H, s, CO$_2$C$\underline{H}_2$C$_6$H$_5$), 5.57 (1H, d, J 3 HZ, 5-α-C$\underline{H}$), 6.94-7.47 (4H, m, CH$_2$C$_6\underline{H}_4$F), 7.24, 7.26 (10H, 2×s, 2×CH$_2$C$_6\underline{H}_5$).

Description 17

Benzyl 9-[N-(2-methoxybenzyl)-N-benzyl]aminodeoxyclavulanate

Benzyl dichloroacetylclavulanate (21 mm) in dry dimethylformamide (70 cm$^3$) at 0° C. was treated with N-2-methoxybenzyl-N-benzylamine (1.9 equivalents) in dimethylformamide (30 cm$^3$) and stirred for 3½ hours at 0° then 1½ hours at 20°. The mixture was poured into ethylacetate (200 cm$^3$) and washed with water (5×50 cm$^3$) and saturated brine (5×50 cm$^3$), dried (anhydrous magnesium sulphate) and evporated in vacuo to yield an oil, 13 g. 5 g of this crude product was chromatographed on silica eluting with ethylacetate:cyclohexane (1:1). Fractions were collected containing the title compound, Rf (SiO$_2$:ethyl acetate:cyclohexane; 1:1)=0.74. Combined fractions were evaporated in vacuo to yield an oil, 1.2 g. ν(film) 1805, 1745, 750, 700 cm$^{-1}$. δ(CDCl$_3$) 2.93 (1H, s, J 17 Hz, 6βC$\underline{H}$), 3.17 (2H, d, J 7 Hz, 9CH$_2$), 3.40 (1H, dd, J 17 and 3 Hz, 6αC$\underline{H}$), 3.54. 3.57 (4H, 2×s, 2×NCH$_2$), 3.75 (3H, s, OCH$_3$), 4.86 (1H, t, J 7 Hz, 8C$\underline{H}$), 5.02 (1H, s, 3C$\underline{H}$), 5.14 (2H, s, CO$_2$C$\underline{H}_2$C$_6$H$_5$), 5.57 (1H, d, J 3 Hz, 5αC$\underline{H}$), 6.75-7.45 (14H, m, 2×CH$_2$C$_6\underline{H}_5$, CH$_2$C$_6$H$_4$OCH$_3$).

Description 18

Benzyl trichloroacetylclavulanate

Benzyl clavulanate (5.78 g, 20 mmol) in dry methylene chloride (100 ml) was cooled to −30° C. and treated with pyridine (1.61 ml). Trichloroacetyl chloride (2.23 ml, 20 mmol) in dry methylene chloride (10 ml) was then added dropwise over a period of 10 mins. After a further 10 mins. at −30° C. the reaction mixture was poured into dilute hydrochloric acid (100 ml, 2 M). The organic phase was washed with water, sodium bicarbonate solution, brine, dried and evaporated to afford the product as an oil, 7.81 g (90%). νmax (film) 1800, 1750 and 1680 cm$^{-1}$.

Description 19

Benzyl dichloroacetylclavulanate

Benzyl clavulanate (20.2 g; 70 mm) in dichloromethane (100 cm$^3$) was treated with dry pyridine (1 equivalent) and cooled to −20° C. Dichloroacetyl chloride (10.3 g; 1 equivalent) was added in dichloromethane (20 cm$^3$), dropwise, and the reaction stirred for 20 minutes. The mixture was washed with water (5×100 cm$^3$) and saturated brine (5×100 cm$^3$), dried (anhydrous magnesium sulphate) and evaporated in vacuo to an oil, yield=27.5 g (98%). ν(film) 1800, 1745, 1690, 1295, 1170, 1120, 1085, 1042, 1020, 1000, 955, 890, 815, 742, 700 cm$^{-1}$. δ(CDCl$_3$) 3.05 (1H, d, J 17 Hz, 6βCH), 3.50 (1H, dd, J 17 and 3 Hz, 6αC$\underline{H}$), 4.82 (3H, s, 8C$\underline{H}$ and 9CH$_2$), 5.10 (1H, s, 3C$\underline{H}$), 5.17 (2H, s, C$\underline{H}_2$C$_6$H$_5$), 5.70 (1H, d, J 3 Hz, 5αC$\underline{H}$), 5.90 (1H, s, C$\underline{H}$Cl$_2$), 7.32 (5H, s, CH$_2$C$_6$H$_5$).

Description 20

Benzyl monochloroacetylclavulanate

Benzyl clavulanate (2.51 g, 8.7 mmol) was dissolved in methylene chloride (30 ml) and treated with pyridine (0.775 ml, 9.60 mmol) at room temperature. The reaction mixture was cooled to −30° C. and chloroacetyl chloride (0.69 ml, 8.7 mmol) in methylene chloride (10 ml) was added dropwise over ten minutes. After stirring at −30° C. for a further ten minutes the reaction mixture was poured into dilute hydrochloric acid and extracted with methylene chloride. The organic phase was washed successively with dilute hydrochloric acid, sodium bicarbonate solution, brine, and dried (MgSO$_4$). Evaporation in vacuo afforded a pale yellow oil homogeneous by t.l.c., 3.10 g. νmax (CHCl$_3$), 1803, 1755 (br) and 1700 cm$^{-1}$.

Description 21

Methyl dichloroacetylclavulanate

Methyl clavulanate (1.03 g; 4.8 mm) in dichloromethane (30 cm$^3$) was treated with pyridine (1 equivalent) and cooled to −20°, then treated with dichloroacetyl chloride (1 equivalent) and stirred for 10 minutes. The solution was washed with water (2×50 cm$^3$) and saturated brine (5×50 cm$^3$), dried (anhydrous magnesium sulphate) and evaporated in vacuo to an oil, 1.31 g. ν(film) 1805, 1750, 1690, 1300, 1240, 1165, 1045, 1010, 960, 890, 820 cm$^{-1}$. δ(CDCl$_3$) 3.08 (1H, d, J 17 Hz, 6βC$\underline{H}$), 3.51 (1H, dd, J 17 and 3 HZ, 6αC$\underline{H}$), 3.77 (3H, s, CO$_2$C$\underline{H}_3$), 4.85 (3H, s, 8C$\underline{H}$ and 9CH$_2$), 5.08 (1H, s, 3C$\underline{H}$), 5.72 (1H, d, J 3 HZ, 5α-C$\underline{H}$), 5.91 (1H, s, C$\underline{H}$Cl$_2$).

Description 22

Methyl 9-[N-(4-acetamidobenzyl)-N-benzyl]aminodeoxyclavulanate

Methyl dichloroacetylclavulanate (1.25 g; 3.86 mm) in dimethylfomamide (30 cm$^3$) was treated at 0° with N-(4-acetamidobenzyl)benzylamine (1.9 equivalents) and stirred for 4 hours; poured into ethylacetate (200 cm³) and washed with water (5×50 cm³) and saturated brine (5×50 cm³), dried (anhydrous magnesium sulphate) and evaporated in vacuo to an oil. This oil was chromatographed on silica eluting with ethylacetate-cyclohexane 1:1 grading to neat ethylacetate; fractions were collected containing the title compound, Rf (SiO₂/ethylacetate)=0.60. Combined fractions were evaporated in vacuo to yield an oil, yield=0.61 g. $\nu$(film) 3300 (broad), 1800, 1750, 1690, 1670, 750, 700 cm⁻¹. $\nu$(KBr) (3650-3150), 1800, 1750, 1690, 1665, 1600, 1530, 1515, 1412, 1370, 1312, 1265, 1240, 1200, 1180, 1120, 1010, 745, 700 cm⁻¹.

$\delta$(CDCl₃) 2.13 (3H, s, COC$\underline{H}_3$), 2.95 (1H, d, J 17 Hz, 6$\beta$C$\underline{H}$), 3.14 (2H, d, J 7 Hz, 9C$\underline{H}_2$), 3.41 (1H, dd, J=17 and 3 Hz, 6$\alpha$C$\underline{H}$), 3.48, 3.52 (4H, 2×s, 2×NCH₂), 3.73 (3H, s, CO₂C$\underline{H}_3$), 4.74 (1H, t, J 7 Hz, 8C$\underline{H}$), 4.97 (1H, s, 3CH), 5.57 (1H, d, J 3 Hz and 5$\alpha$CH), 7.17-7.45 (9H, m, CH₂C₆$\underline{H}_5$ and CH₂C₆$\underline{H}_4$NHCOCH₃).

Description 23
Benzyl 9-N-benzyl-N-(4-hydroxy-3-methoxy-benzyl-)aminodeoxyclavulanate Benzyl dichloroacetylclavulanate (4.07 g 10.2 mm) in dimethylformamide (75 cm³) at 0° was treated with N-benzyl-N-(4-hydroxy-3-methoxybenzyl) amine (4.7 g; 1.9 equivalents) in dimethylformamide (20 cm³), dropwise and stirred at 0° for ½ hr then at 20° for 1½ hrs. The reaction mixture was poured into ethylacetate (200 cm³) and the organic phase washed with water (3×75 cm³) and saturated brine (4×75 cm³). The ethyl acetate phase was dried and evaporated in vacuo to yield a coloured foam. This foam was chromatographed on silica gel, eluting with ethylacetate-cyclohexane; 1:1. Fractions were collected containing the title compound and were evaporated in vacuo to yield 2.32 g (44%) of a colourless oil; Rf (SiO₂/ethylacetate:cyclohexane; 1:1)=0.66, detection by aqueous potassium permanganate spray. $\nu$(film) 3500 broad, 1800, 1750, 1695, 1610, 1602, 1512, 1450, 1430, 1380, 1302, 1270, 1230, 1180, 1155, 1120, 1080, 1032, 1015, 820, 800, 750, 700 cm⁻¹. $\delta$(CDCl₃) 2.85 (1H, d, J 17 Hz, 6$\beta$C$\underline{H}$), 3.10 (2H, d, J 7 Hz, 9CH₂), 3.31 (1H, dd, J 17 and 31 Hz, 6$\alpha$C$\underline{H}$), 3.35, 3.41 (4H, 2×s, NCH₂C₆H₅ and NCH₂C₆H₃(OH,OCH₃)), 3.74 (3H, s, OCH₃), 4.80 (1H, t, J 7 Hz, 8CH), 5.00 (1H, s, 3-C$\underline{H}$), 5.09 (2H, s, OCH₂C₆H₅), 5.25 (1H, broad s, exchanges with D₂O-C₆H₃(O$\underline{H}$, OCH₃), 5.51 (1H, d, J 3 Hz, 5$\alpha$C$\underline{H}$), 6.71-6.78 (3H, m, protons in trisubstituted phenyl group), 7.20 (10H, broad s, 2×CH₂C₆H₅).

Description 25
Allyl 9-O-dichloroacetylclavulanate

Allylclavulanate (6.3 g; 26 mm) in dichloromethane (100 cm³) at −30° C. was treated with pyridine (3 cm³) and dichloroacetylchloride (1 equivalent) and stirred for 10 minutes at −20° C. The mixture was diluted with dichloromethane (100 cm³) and washed with aqueous citric acid solution (10%, 50 cm³), water (3×100 cm³), saturated brine (3×150 cm³), dried (anhydrous magnesium sulphate) and evaporated to an oil yield=8.3 g (90%), Rf (SiO₂/ethylacetate-cyclohexane 1:1)=0.78.

Description 26
Phenacyl-9-Dichloroacetyl Clavulanate

Phenacyl clavulanate (14.26 g; 45 mmol) in dry methylene chloride (100 ml) was treated with pyridine (4 mls, 50.6 mmol) at room temperature. The reaction mixture was cooled to −30° C. and dichloroacetyl chloride (4.3 mls, 1.2 equivalents) in dry methylene chloride (15 ml) was added dropwise. After stirring at −30° C. for 30 minutes the mixture was allowed to warm to 0° C. and was then poured into dilute hydrochloric acid. The organic phase was separated and washed with more dilute hydrochloric acid, sodium bicarbonate solution, water, brine and then dried (MgSO₄). After filtration the methylene chloride was removed in vacuo to afford a yellow oil which crystallised on trituration with ether. Yield=11.21 g, 50%. A sample recrystallised from ether gave the following physical characteristics: m.p. 75°-77° C. $[\alpha]_D^{20}$+16.1°, (c, 1%; CHCl₃).

Description 27
(2-Methylallyl)clavulanate

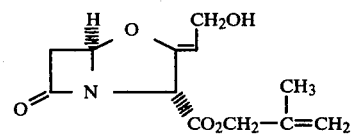

Sodium clavulanate (25 g; 83 mmol) in anhydrous dimethylformamide (100 ml) was treated at room temperature over a period of 15 minutes with methylallylchloride (15.1 g; 166 mmol) in dimethylformamide (50 ml) plus a catalytic amount of sodium iodide. The mixture was then stirred at room temperature overnight.

The mixture was then poured into an ethyl acetate/water mixture and shaken. The two layers were separated and the aqueous layer extracted with ethyl acetate. The organic layers were combined, washed with water, washed with a saturated solution of sodium chloride, dried (MgSO₄) and evaporated to give the title compound as an oil in 73% yield.

$\nu$max (CHCl₃): 1810, 1750, 1695 and 1660 cm⁻¹. (CDCl₃): 1.75 (4H, s), 3.05 (1H, d, J 17 Hz), 3.50 (1H, dd, J 17 and 3 Hz), 4.23 (2H, d, J 7 Hz), 4.58 (2H, s), 4.93 (1H, t, J 7 Hz), 5.00 (2H, broad s), 5.09 (1H, m), and 5.70 (1H, d, J 3 Hz).

Description 28
(2-Methylallyl)-9'-O-Dichloroacetylclavulanate

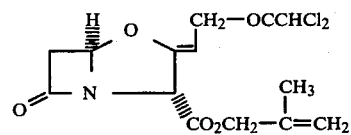

(2-Methylallyl)clavulanate (15.3 g; 60 mmole) in anhydrous dichloromethane (150 ml) was treated at room temperature with anhydrous pyridine (4.8 ml; 60 mmol) and was added dropwise over a period of 10 minutes. The reaction mixture was stirred at −40° C. for 1 hour and then allowed to warm to 0° C.

The mixture was poured into cold dilute hydrochloric acid and separated. The organic layer was then washed several times with more dilute hydrochloric acid, water and a saturated solution of sodium chloride, dried (MgSO₄) and evaporated to an oil affording the title compound in 87% yield.

$\nu_{max}$(CHCl₃): 1810, 1755 and 1700 cm⁻¹. (CDCl₃): 1.76 (3H, s), 3.10 (1H, d, J 17 Hz), 3.56 (1H, dd, J 17 and 3 Hz), 4.60 (2H, s), 4.78 to 5.00 (5H, m), 5.13 (1H, s), 5.77 (1H, d, J 3 Hz), and 5.93 (1H, s).

EXAMPLE 1

9-N-(2-Hydroxyethyl)aminodeoxyclavulanic acid p-Methoxybenzyl 9-[N-benzyl-N-(2-hydroxyethyl)-]aminodeoxyclavulanate (0.38 g) in ethanol and tetrahydrofuran (1:1) (100 cm$^3$) was hydrogenated with 10% palladium on carbon as catalyst (0.15 g) for 23 hours. The mixture was filtered through celite and the clear filtrate evaporated in vacuo to yield a coloured oil. This oil was dissolved in ethyl acetate (100 cm$^3$) and extracted with water (50 cm$^3$). The aqueous extract was evaporated in vacuo to yield a pale yellow oil. This oil was chromatographed on a cellulose column, eluting with butanol/propan-2-ol/water 7:7:5. Fractions were collected containing only (1), Rf (SiO$_2$:butanol:propan-2-ol:water, 7:7:6)=0.20, detection by aqueous potassium permanganate spray. The combined fractions containing only 9-N-(2-hydroxyethyl)aminodeoxyclavulanic acid were evaporated in vacuo to yield a white solid, (50 mg); $\delta$(D$_2$O) 3.1. (1H, d, J 17 Hz, 6$\beta$-C$\underline{H}$), 3.05-3.17 (2H, m, NC$\underline{H_2}$CH$_2$OH), 3.57 (1H, dd, J 17 Hz and 3 Hz, 6$\alpha$-C$\underline{H}$), 3.70-3.84 (4H, m, NCH$_2$C$\underline{H_2}$OH, 9-C$\underline{H_2}$), 4.80 (1H, t, J 8 Hz, 8C$\underline{H}$), 4.99 (1H, s, 3-C$\underline{H}$), 5.76 (1H, d, J 3 Hz, 5$\alpha$-CH). [CH$_3$CN was used as an internal standard, $\delta$CH$_3$CN=2.00]; $\nu$(KBr) 3000-3600, 1785, 1620 cm$^{-1}$.

EXAMPLE 2

9-N-Benzylaminodeoxyclavulanic acid

Benzyl 9-(N,N-dibenzylamino)deoxyclavulanate (0.43 g) in ethanol and tetrahydrofuran, 1:1 (75 cm$^3$) with 1 cm$^3$ water was hydrogenated with 5% palladium on carbon (0.43 g) as catalyst. The hydrogenation was carried out at 55 psi for 5 hours. The mixture was filtered through celite and the clear filtrate evaporated in vacuo to yield a coloured oil. This oil was dissolved in ethyl acetate (80 cm$^3$) and washed with water (3×30 cm$^3$). The combined aqueous extracts were evaporated in vacuo to yield a pale yellow oil. This oil was chromatographed on a cellulose column, eluting with butanol/propan-2-ol/water; 4:4:1. Fractions were collected containing 9-N-benzylaminodeoxyclavulanic acid, detection by aqueous potassium permanganate spray; Rf (SiO$_2$; butanol/propan-2-ol/water, 7:7:6)=0.45. The combined fractions were evaporated in vacuo to yield a solid. This solid was washed with ethanol and then dried to yield 9-N-benzylaminodeoxyclavulanic acid (36 mg). $\nu$(KBr) (3680-3150), (3100-2900), (2900-2300), 1800, 1694, 1610, 1460, 1400, 1305, 1190, 1020, 895, 755, 700 cm$^{-1}$; $\delta$(D$_2$O+5% DMSO D-6), 3.13 (1H, d, J 17 Hz, 6$\beta$-C$\underline{H}$), 3.62 (1H, bd, J 17 Hz, 6$\alpha$-C$\underline{H}$), 3.77 (2H, d, J 8 Hz, 9-C$\underline{H_2}$), 4.22 (2H, s, C$\underline{H_2}$C$_6$H$_5$), 4.84 (1H, t, J 8 Hz, 8-C$\underline{H}$), 5.01 (1H, s, 3-C$\underline{H}$), 5.77 (1H, bs, 5$\alpha$-C$\underline{H}$), 7.48 (5H, s, C$_6\underline{H}_5$).

The compound of this invention was produced as fine needles, (ie. in crystalline form). Crystalline 9-N-benzylaminodeoxyclavulanic acid is normally colourless. Chemical Analysis of the product indicated that the crystals contained water.

EXAMPLE 3

9-N-Ethylaminodeoxyclavulanic Acid

Benzyl 9-(N-benzyl-N-ethyl)aminodeoxyclavulanate [3.44 g; obtained by the reaction of benzyl trichloroacetylclavulanate (3 g) with 2 equivalents of N-benzylethylamine] in ethanol and tetrahydrofuran, 1:1 (100 cm$^3$) with 1 cm$^3$ water was hydrogenated with 10% palladium on carbon (1 g) as catalyst. The hydrogenation was carried out for 16 hours at atmospheric pressure. The mixture was filtered through celite and the clear filtrate evaporated in vacuo to yield an oil. This oil was dissolved in ethyl acetate (100 cm$^3$) and extracted with water (3×40 cm$^3$). The combined aqueous extracts were evaporated in vacuo to yield a pale yellow oil. This oil was chromatographed on a cellulose column, eluting with butanol/propan-2-ol/water; 4:4:1. Fractions were collected containing 9-ethylaminodeoxyclavulanic acid; Rf (SiO$_2$; butanol/propan-2-ol/water; 7:7:6)=0.17, detection by aqueous potassium permanganate spray. The combined fractions were evaporated in vacuo to yield 9-N-ethylaminodeoxyclavulanic acid as a colourless crystalline solid (13% overall yield from benzyl trichloroacetylclavulanate); $\nu$(KBr) (3700-3250), (3200-2900), (2900-2600), (2600-2400), 1790, 1695, 1625, 1460, 1400, 1305, 1190, 1120, 1045, 1020, 900, 800, 745 cm$^{-1}$; $\delta$(D$_2$O) 1.22 (3H, t, J 7 Hz, —CH$_2$C$\underline{H_3}$), 2.89-3.20 (3H, m, —C$\underline{H_2}$CH$_3$ and 6$\beta$-C$\underline{H}$), 3.57 (1H, broad d, J 17 Hz, 6$\alpha$-C$\underline{H}$), 3.68 (2H, d, J 8 Hz, 9-C$\underline{H_2}$), 4.78 (1H, t, J 8 Hz, 8-C$\underline{H}$), 5.00 (1H, s, 3-C$\underline{H}$), 5.73 (1H, broad s, 5$\alpha$-C$\underline{H}$).

EXAMPLE 4

9-N-(dl-2-Hydroxypropyl)aminodeoxyclavulanic acid

Benzyl 9-[N-benzyl-N(dl-2-hydroxypropyl)-]aminodeoxyclavulanate (3.5 mM) in ethanol and tetrahydrofuran, 1:1 (75 cm$^3$) with 1 cm$^3$ water was hydrogenated with 10% Palladium on carbon (0.9 g) as catalyst. The hydrogenation was carried out at atmospheric pressure for 21 hours. Thin layer chromatography showed one major spot at Rf (SiO$_2$/butanol:propan-2-ol:water, 7:7:6)=0.24. Detection by potassium permanganate spray. The mixture was filtered through celite and the clear filtrate evaporated in vacuo to yield an oil. This oil was dissolved in ethyl acetate (100 cm$^3$) and extracted with water (3×50 cm$^3$). The combined aqueous extracts were evaporated in vacuo to yield a pale yellow oil. This oil was chromatographed on a cellulose column, eluting with butanol/propan-2-ol/water, 4:4:1. Fractions were collected containing 9-[N-(dl-2-hydroxypropyl)]aminodeoxyclavulanic acid, Rf (SiO$_2$/butanol:propan-2-ol:water, 7:7:6)=0.24. The combined fractions were evaporated in vacuo to yield 9-N-(dl-2-hydroxypropyl)aminodeoxyclavulanic acid as a colourless oil in a 12% yield; $\delta$(D$_2$O) 1.21 (3H, d, J 6 Hz, —CH$_2$CH(OH)C$\underline{H_3}$), 2.7-3.2 (3H, m, 6$\beta$-C$\underline{H}$, C$\underline{H_2}$CH(OH)CH$_3$), 3.57 (1H, broad d, J 17 Hz, 6$\alpha$-C$\underline{H}$), 3.76 (2H, d,J 8 Hz, 9-CH$_2$), 3.83-4.21 (1H, m, —CH$_2$C$\underline{H}$(OH)CH$_3$), 4.80 (1H, t, J 8 Hz, 8-C$\underline{H}$), 5.01 (1H, s, 3-C$\underline{H}$), 5.75 (1H, broad s, 5$\alpha$-C$\underline{H}$).

EXAMPLE 5

9-(4-Fluorobenzyl)aminodeoxyclavulanic acid

Benzyl 9-N-benzyl-N-(4-fluorobenzyl)aminodeoxyclavulanate (7 g of approximately 50% pure material) in 100 cm$^3$ tetrahydrofuran-ethanol (50%) plus 4 cm$^3$ water, was hydrogenated at 55 p.s.i. for 21 hours in the presence of 4 g palladium on carbon (10%). The mixture was filtered through celite and the clear filtrate evaporated to a coloured oil. This oil was dissolved in ethyl acetate (80 cm$^3$) and extracted with water (3×30 cm$^3$). The combined aqueous extracts were evaporated in vacuo to yield a coloured oil. This oil was chromatographed on a cellulose column, eluting with butanol/propan-2-ol/water; 4:4:1. Fractions containing the title compound were collected, (detection by aqueous potassium permanganate spray; Rf (SiO$_2$/butanol/propan-2-ol/water, 7:7:6)=0.63). The combined fractions were evaporated in vacuo to yield a colourless material which crystallised on the addition of ethanol and cooling. The crystals were washed with cold (0° C.) ethanol and dried to yield 9-(4-fluorobenzyl)aminodeoxyclavulanic acid (367 mg). ν(KBr) (3700-3120), (3120-2900), (2900-2650), (2650-2500), (2500-2300), 1805, 1695, 1580, 1515, 1470, 1410, 1340, 1303, 1283, 1230, 1185, 1165, 1045, 1008, 992, 895, 858, 835, 773 cm$^{-1}$.

EXAMPLE 6

9-N-(Methylbenzyl)aminodeoxyclavulanic acid

Benzyl 9-N-benzyl-N-(4-methylbenzyl)aminodeoxyclavulanate (10.6 g of approximately 50% pure material) in 100 cm$^3$ tetrahydrofuran-ethanol (50%) plus 4 cm$^3$ water was hydrogenated at 55 p.s.i. for 21 hours in the presence of 5 g palladium on carbon (10%). The mixture was filtered through celite and the clear filtrate evaporated in vacuo to a coloured oil. This oil was chromatographed on cellulose, eluting with butanol/propan-2-ol/water: 4:4:1. Fractions containing the title compound were collected, detection by aqueous potassium permanganate spray; Rf (SiO$_2$; butanol/propan-2-ol/water, 7:7:6)=0.60. The combined fractions were evaporated in vacuo to yield an oil to which was added ethanol. On cooling a colourless crystalline solid formed. This was filtered off, washed with cold ethanol and dried to yield 85 mg of zwitterionic 9-N-(4-methylbenzyl)aminodeoxyclavulanic acid as fine needles. ν(KBr) (3670-3150), (3150-2870), (2870-2500), (2500-2250), 1790, 1690, 1590, 1460, 1395, 1300, 1195, 1110, 1035, 1015, 1000, 990, 940, 892, 805, 748, 555, 485, 435 cm$^{-1}$.

EXAMPLE 7

9-N-(4-Methoxybenzyl)aminodeoxyclavulanic acid

Benzyl 9-N-benzyl-N-(4-methoxybenzyl)aminodeoxyclavulanate (1.4 g) in 100 cm$^3$ tetrahydrofuranethanol (50%) plus 2 cm$^3$ water was hydrogenated at 55 p.s.i. for 21 hours in the presence of 1 g palladium on carbon (10%). The reaction mixture was filtered through celite and the filtrate evaporated in vacuo to yield a coloured foam. This foam was chromatographed on cellulose eluting with butanol-isopropanol-water; 4:4:1. Fractions containing the title compound only were collected. Rf (SiO$_2$/butanol-isopropanol-water; 7:7:6)=0.60, detection by aqueous potassium permanganate spray. These fractions were evaporated in vacuo to yield a colourless residue. Trituration of the residue under cooled ethanol yielded solid zwitterionic 9-N-(4-methoxybenzyl)aminodeoxyclavulanic acid as fine needles, (33 mg). ν(KBr) (3600), (3500-3150), (3150-2880), (2880-2780), (2780-2680), (2680-2520), (2520-2250), 1790, 1695, 1600, 1517, 1470, 1400, 1305, 1255, 1200, 1184, 1125, 1030, 995, 950, 900, 840, 820, 767, 760, 575, 545, 445 cm$^{-1}$.

EXAMPLE 8

9-N-(4-Hydroxy-3-methoxybenzyl)aminodeoxyclavulanic acid

Benzyl 9-N-(4-benzoxy-3-methoxybenzyl)benzylaminodeoxyclavulanate (0.7 g of approximately 50% pure material) in tetrahydrofuran-ethanol (50%) 50 cm$^3$ plus 2 cm$^3$ water was hydrogenated at 55 p.s.i. for 15 hours in the presence of 0.5 g palladium on carbon (10%). The reaction mixture was filtered through celite and the filtrate evaporated in vacuo to yield a coloured oil. This oil was dissolved in ethyl acetate (50 cm$^3$) and extracted with water (2×25 cm$^3$). The combined aqueous extracts were evaporated in vacuo to yield a coloured foam. This foam was chromatographed on a cellulose column, eluting with butanol/propan-2-ol/water 4:4:1. Fractions containing the title compound were collected and evaporated in vacuo to yield 9-N-(4-hydroxy-3-methoxybenzyl)aminodeoxyclavulanic acid as a white solid (30 mg). Rf (SiO$_2$/butanol-propan-2-ol-water; 7:7:6)=0.56. The p.m.r. spectrum was consistent with the desired product.

EXAMPLE 9

9-N-(4-Hydroxy-3-methoxybenzyl)aminodeoxyclavulanic acid

Benzyl 9-N-(4-hydroxy-3-methoxybenzyl)benzyl aminodeoxyclavulanate (2.27 g) in 80 cm'tetrahydrofuran-ethanol (50%) plus 2 cm$^3$ water, was hydrogenated at 55 psi for 6 hours in the presence of 2 g palladium on charcoal (10%). The mixture was filtered through celite and the clear filtrate evaporated in vacuo to yield a pale yellow foam. To this foam was added methanol (5 cm$^3$), then to this solution was added dry acetone (70 cm$^3$) and the resultant precipitated white solid filtered off and dried, yield 0.88 g. 0.83 g of this crude material was chromatographed on cellulose with butanol/propan-2-ol/water; 4:4:1. Fractions were collected containing the title compound and were evaporated in vacuo to yield a white solid. Propan-2-ol was added (20 cm$^3$) followed by methanol (10 cm$^3$) and the solution cooled (0° C.). The crystalline product was filtered off and washed with cold (0°) methanol and dried to yield 9-N-(4-hydroxy-3-methoxybenzyl)aminodeoxyclavulanic acid as fine needles (102 mg). Rf (SiO$_2$/butanol-propan-2-ol-water; 7:7:6)=0.60.

EXAMPLE 10

9-N-Benzylaminodeoxyclavulanic acid

Benzyl 9-N,N-di-benzylaminodeoxyclavulanate (13 g) was dissolved in 60 cm$^3$ tetrahydrofuran plus 50 cm$^3$ of aqueous propan-2-ol (H$_2$O: IPA=2:5). To this was added 6 g of palladium on charcoal (10%) which had been previously washed with water (to neutral filtrate). The reaction mixture was hydrogenated at 55 psi for 6½ hours, filtered through celite (pH of the filtrate was 5.37) and washed with aqueous tetrahydrofuran (50%, 150 cm$^3$) followed by aqueous ethanol (50%, 200 cm$^3$). The filtrate from the final washing was collected separately and evaporated to yield a white solid. Ethanol was added (20 cm$^3$) and cooled (0°), then filtered and washed with ice-cold ethanol, and dried in vacuo to yield 9-N-benzylaminodeoxyclavulanic acid as a finely crystalline solid (0.32 g). The main filtrate was evaporated and ethanol added (50 cm$^3$) resulting in rapid crystallisation. The solid was filtered off and washed with ice-cold ethanol and dried in vacuo to yield 9-N-benzylaminodeoxyclavulanic acid as a very slightly off-white crystalline solid (1.57 g). The filtrate was again evaporated but this time ethanol was added (50 cm$^3$). Cooling yielded fine crystals, which were filtered off and washed with ice-cold methanol, and dried in vacuo to yield the 9-N-benzylaminodeoxyclavulanic acid as a finely crystalline solid (0.25 g). The total yield was 2.14 g. (assuming the dibenzylamino compound was 90% pure this represents a yield of 30%). The coloured residue was evaporated and redissolved in ethanol. This solution was applied to a cellulose column 180 cm×4½ cm and partially eluted with ethanol (50 to 70 cm³) and then with butanol/isopropanol/water; 4:4:1. Fractions were collected containing virtually only 9-N-benzylaminodeoxyclavulanic acid were evaporated and methanol added; the resulting fine crystals of the desired compound were filtered off and washed with cold methanol to yield further 67 mg.

νmax (nujol) 3620, 3540, 3400 broad, 3200 broad, 2800–2500, 2500–2300, 1810, 1690, 1610, 1575, 1395, 1185, 1145, 1115, 1080, 1060, 1040, 1030, 1015, 1005, 990, 945, 895, 865, 850, 815, 790, 755, 700 cm⁻¹.

Cu Kα radiation, 36 kV, 26 mA, scan speed ⅛° 2θ/min, scanned 33°→20° 2θ: Reflections at the following approx. angles 2θ: 11.5, 13.5, 15.2, 15.8, 16.4, 17.25, 18.2, (broad), 19.5, 21.0, 21.8, 22.5, 23.1, 24.1, 24.3, 25.2, 25.5, 26.0, 27.5, 28.4, 28.9, 29.6, 32.6, (major reflections underlined).

EXAMPLE 11

9-N-(4-Hydroxybenzyl)-aminodeoxyclavulanic acid

Benzyl 9-N(4-benzoxybenzyl) benzylamino deoxyclavulanate (4 g of approximately 50% pure material) in tetrahydrofuran (60 cm³) and aqueous propan-2-ol (50%; 50 cm³) was hydrogenated at 55 psi for 6¼ hours in the presence of 2 g palladium on carbon (10%). The mixture was filtered through celite and the catalyst washed with aqueous ethanol (200 cm³). The filtrate was evaporated in vacuo to yield a coloured foam. The foam was dissolved in ethanol (10 cm³) and dry ether added (100 cm³), the resultant precipitate was filtered off and dried, dissolved in a small volume of ethanol and chromatographed on cellulose, eluting with ethanol (60 cm³) then butanol/propan-2-ol/water; (4:4:1). Fractions were collected containing the title compound (detection by aqueous potassium permanganate spray), Rf (SiO₂/butanol/propan-2-ol/water; 7:7:6)=0.67. Combined fractions were evaporated in vacuo to yield an oil, trituration with cold methanol yielded 9-N(4-hydroxybenzyl) aminodeoxyclavulanic acid as fine crystals; (4.7 mg).

ν(nujol mull) 3575, 3350, 3175, 1780, 1695, 1620, 1580, 1520, 1310, 1200, 1125, 1105, 1075, 1050, 1020, 1005, 985, 895, 840, 750, 720 cm⁻¹.

EXAMPLE 12

9-N-(3,4-Dimethoxybenzyl)aminodeoxyclavulanate

Using the procedures of the foregoing Examples, hydrogenation of benzyl 9-N-(3,4-dimethoxybenzyl)aminodeoxyclavulanate yields zwitterionic 9-N-(3,4-dimethoxybenzyl)aminodeoxyclavulanate.

EXAMPLE 13

9-N-(4-Acetamidobenzyl)aminodeoxyclavulanic acid

Benzyl 9-N-(4-acetamidobenzyl)benzylaminodeoxyclavulanate (0.9 g) in tetrahydrofuran (50 cm³) and water (10 cm³) was hydrogenated at atmospheric pressure in the presence of 0.3 g palladium on carbon (10%) for 40 minutes. The mixture was filtered through celite and the catalyst washed with aqueous tetrahydrofuran (1:1, 100 cm³) and aqueous ethanol (1:1, 150 cm³). The clear filtrate was evaporated in vacuo, ethanol was added (20 cm³) and after cooling, colourless crystals were filtered off and dried to give 9-N-(4-acetamidobenzyl)aminodeoxyclavulanic acid (309 mg).

The filtrate was evaporated in vacuo after which the addition of cold methanol yielded a further amount of the title compound (37 mg). Rf (SiO₂/butanol-propan-2-ol-water; 7:7:6)=0.45; detection by aqueous potassium permanganate spray. ν(Nujol Mull) (3600–3440), 3380, (3350–3200), 3180, 3120, 2720, (2670–2520), 2450, (1805–1785), 1690, 1670, 1600, 1530, 1310, 1200, 1110, 1070, 1050, 1035, 1020, 1000, 990, 940, 895, 840, 750 cm⁻¹.

δ(D₂O/DMSO) 2.01 (3H, s, C$\underline{H}_3$CONH), 2.88 (1H, d, J 17 Hz, 6βC$\underline{H}$), 3.38–3.53 (3H, m, 6αC$\underline{H}$, 9C$\underline{H}_2$), 3.95 (2H, s, NC$\underline{H}_2$), 4.61–4.75 (2H, m, 3C$\underline{H}$, 8C$\underline{H}$), 5.62 (1H, broad s, 5αC$\underline{H}$), 7.30–7.56 (4H, ABq, J 9 Hz, C$\underline{H}_2$C₆H₄-p-NHCOCH₃).

EXAMPLE 14

9-N-(2-Methoxybenzyl)aminodeoxyclavulanic acid

Benzyl 9-N-(2-methoxybenzyl)benzylaminodeoxyclavulanate (8 g of crude product) in tetrahydrofuran (100 cm³) and water (10 cm³) was hydrogenated in the presence of 10% palladium on carbon (1 g) at atmospheric pressure for 1½ hours. The mixture was filtered and the catalyst washed with aqueous tetrahydrofuran (100 cm³), the filtrate was evaporated in vacuo, to the residue was added ethyl acetate (150 cm³) and then washed with water (2×75 cm³). The combined aqueous extracts were evaporated in vacuo to a foam (3 g). This foam was chromatographed on cellulose eluting with butanol/propan-2-ol/water: 8:8:1. Fractions were collected containing the title compound, Rf (SiO₂/butanol-propan-2-ol-water; 7:7:6) 0.60 (detection by aqueous potassium permanganate spray). Combined fractions were evaporated in vacuo. On addition of cold ethanol colourless crystals formed; the crystals were filtered off and washed with cold ethanol and dried to yield 9-N-(2-methoxybenzyl)aminodeoxyclavulanic acid (140 mg). ν(Nujol mull) (3320–3220), (2750–2100), 1800, 1685, 1610, 1300, 1260, 1185, 1120, 1085, 1070, 1055, 1030, 1020, 1005, 935, 900, 775, 755, 745 cm⁻¹.

EXAMPLE 15

9-N-(2-Fluorobenzyl)aminodeoxyclavulanic acid

Benzyl 9-N-(2-fluorobenzyl)benzylaminodeoxyclavulanate (0.35 g) in tetrahydrofuran (30 cm³) and water (3 cm³) was hydrogenated in the presence of 30% palladium on carbon (40 mg) at atmospheric pressure for 4 hours. A further quantity (40 mg) of the same catalyst was added and hydrogenolysis continued for 15 hours. The mixture was filtered and the catalyst washed with aqueous ethanol (50 cm³) and evaporated in vacuo. Addition of cold ethanol yielded 9-N-(2-fluorobenzyl)aminodeoxyclavulanic acid as a colourless crystalline solid (47 mg) Rf (SiO₂/butanol-propan-2-ol-water; 7:7:6)=0.51 (detection by aqueous potassium permanganate spray. ν(KBr), (3680–3140), (3140–2880), (2880–2500), (2500–2200), 1785, 1694, 1615, 1496, 1457, 1380, 1308, 1240, 1193, 1110, 1043, 1020, 900, 865 cm⁻¹.

δ(D₂O) 3.05 (1H, d, J 17 Hz, 6βC$\underline{H}$), 3.54 (1H, dd, J 17 and 3 Hz 6αC$\underline{H}$), 3.72 (2H, d, J 7 Hz, 9C$\underline{H}_2$), 4.23 (2H, s, NC$\underline{H}_2$C₆H₄F), 4.77 (1H, t, J 7 Hz, 8C$\underline{H}$), 4.95 (1H, s, 3C$\underline{H}$), 5.70 (1H, d, J 3 Hz, 5αC$\underline{H}$), 7.05–7.48 (4H, m, CH₂C₆$\underline{H}_4$F).

EXAMPLE 16

Carboxymethyl 9-N-benzylaminodeoxyclavulanate

Benzyloxycarbonylmethyl 9-N-benzyloxycarbonyl-N-benzylaminodeoxyclavulanate (279 mg) was dissolved in tetrahydrofuran (20 ml) and water (2 ml) and hydrogenated at normal temperature and pressure over 10% palladium on carbon. After the reaction was complete (as judged by tlc) the catalyst was filtered off, washed well with aqueous tetrahydrofuran and the combined filtrated evaporated in vacuo to yield carboxymethyl 9-N-benzylaminodeoxyclavulanate. The residue was triturated with acetone/ether to give carboxymethyl 9-N-benzylaminodeoxyclavulanate as a white solid which was filtered off and dried in a desiccator. max (Nujol) 1975, 1745, 1690, 1610 cm$^{-1}$.

EXAMPLE 17

Methyl 9-N-(4-acetamidobenzyl)aminodeoxyclavulanate hydrogen (L)-malate

Methyl 9-N-(4-acetamidobenzyl)benzylaminodeoxyclavulanate (0.5 g) in tetrahydrofuran (15 cm$^3$) and water (5 cm$^3$) was hydrogenated at atmospheric pressure for 2½ hours in the presence of 0.1 g palladium on carbon catalyst (30%) and malic acid (0.155 g; 1 equivalent). The mixture was filtered and the catalyst washed with aqueous tetrahydrofuran (10 cm$^3$). The filtrate was evaporated in vacuo to an oil. This oil was dissolved in ethanol (10 cm$^3$) and triturated with ether to yield a solid. This solid was washed with ether and dried in vacuo to yield methyl 9-N-(4-acetamidobenzyl)aminodeoxyclavulanate hydrogen L-malate as a solid (343 mg). $\nu$(Nujol) 1800, 1745, 1690, 1670, 1600 cm$^{-1}$.

EXAMPLE 18

Methoxymethyl 9-N-benzylaminodeoxyclavulanate

9-N-Benzylaminodeoxyclavulanic acid (162 mg) in dimethylformamide (10 mls) at 20° was treated with chlorodimethyl ether (42 mls, 1 equivalent) and stirred for 4–5 minutes (when tlc showed no further change). At this point the solution contains the hydrochloride salt of methoxymethyl 9-N-benzylaminodeoxyclavulanic acid; ($R_f$ HCl salt 0.8 on SiO$_2$ using butanol:propanol:water 7:7:6). The mixture was poured into ethyl acetate (100 mls) and water (50 mls) and stirred vigourously while adding sodium bicarbonate (solid) until the pH was 9.5. The organic phase was washed with water (6×50 mls) and saturated brine (3×50 mls), dried (anhydrous magnesium sulphate) and evaporated to yield methoxymethyl 9-N-benzylaminodeoxyclavulanate as an oil (154 mg). (Rf, SiO$_2$/ethyl acetate 0.17).

$\nu$max (film)=3325 (broad), 1800, 1750, 1700, 745, 705 cm$^{-1}$.

EXAMPLE 19

Methoxymethyl 9-benzylaminodeoxyclavulanate hydrochloride

9-Benzylaminodeoxyclavulanic acid (0.4 g) in dimethylformamide (15 ml) was treated at room temperature with chlorodimethyl ether (1 equivalent) and stirred for 5 minutes, the evaporated in vacuo to yield an oil. This oil was dissolved in ethanol (5 ml) and added dropwise to diethyl ether (250 ml) with vigorous stirring. The resultant precipitate was filtered off, washed with dry diethyl ether, and dried in vacuo to yield methoxymethyl 9-benzylaminodeoxyclavulanate hydrochloride as a white solid (320 mg).

$\nu$(Nujol) 2800–2460, 2460–2300, 1800, 1750, 1695, 750, 700 cm$^{-1}$. $\delta$(CD$_3$OD) values include: 3.10 (1H, d, J 17 Hz, 6$\beta$-CH), 3.43 (3H, s, OC$\underline{H}_3$), 3.74 (2H, d, J 7 Hz, 9-C$\underline{H}_2$), 4.15 (2H, s, C$\underline{H}_2$C$_6$H$_5$), 5.27 (2H, s, C$\underline{H}_2$OCH$_3$), 5.77 (1H, d, J 3 Hz, 5-C$\underline{H}$), 7.40 (5H, s, CH$_2$C$_6\underline{H}_5$).

EXAMPLE 20

Ethyl 9-N-benzylaminodeoxyclavulanate

A suspension of 9-N-benzylaminodeoxyclavulanic acid (576 mg) in methylene chloride (20 ml) was treated with a solution of triethyloxonium tetrafluoroborate (380 mg) in methylene chloride (20 mls) and stirred at room temperature for 3 hours until no further change was seen by tlc. The solvent was removed by evaporation to yield ethyl 9-N-benzylaminodeoxyclavulanate tetrafluoroborate. This residue was dissolved in aqueous sodium bicarbonate (roughly one equivalent) and extracted with methylene chloride (2×20 mls). The organic phase was washed with brine (20 mls), dried (anhydrous magnesium sulphate) and evaporated to yield ethyl 9-N-benzylaminodeoxyclavulanate as an oil (250 mgs). Rf=0.2 on SiO$_2$ using ethyl acetate.

$\nu$max (film)=3300 (broad), 1800, 1745, 1695 cm$^{-1}$.

EXAMPLE 21

Benzyloxymethyl 9-N-benzylaminodeoxyclavulanate hydrochloride

9-N-Benzylaminodeoxyclavulanate (288 mg) was dissolved in dry dimethylformamide (15 ml) at room temperature and to this solution was added benzyloxymethyl chloride (157 mg) in dimethylformamide (1 ml). The reaction mixture was stirred at room temperature for a further four hours (tlc showed reaction as complete) and the solvent was removed in vacuo. The residue was dissolved in acetone, filtered through Celite and dry ether added. On cooling and scratching, benzyloxymethyl 9-N-benzylaminodeoxyclavulanate hydrochloride crystallised out and was collected by filtration (220 mg). [$\alpha$]$_D^{20}$= +15.6° (1.0; MeOH); $\nu$max (Nujol) 2725 (b), 1795, 1766, 1700 cm$^{-1}$; $\nu_{max}$ (KBr) 2940 (b), 2700–2840 (b), 1795, 1767, 1698 cm$^{-1}$; $\delta$(CD$_3$OD) 3.08 (1H, d, J 17 Hz, 6$\beta$-C$\underline{H}$), 3.57 (1H, dd, J 3.5 and 17 Hz, 6$\alpha$-C$\underline{H}$), 3.68 (2H, broad d, 9CH$_2$), 4.11 (2H, s, NH$_2$+C$\underline{H}_2$C$_6$H$_5$), 4.69 (2H, s, obscured by water peak, CH$_2$OC$\underline{H}_2$C$_6$H$_5$), 4.85 (1H, t, J 7 Hz, 8C$\underline{H}$), 5.23 (1H, s, 3-C$\underline{H}$), 5.38 (2H, s, CO$_2$C$\underline{H}_2$O), 5.71 (1H, d, J 3 Hz, 5-C$\underline{H}$), 7.23 (5H, s, aromatic -$\underline{H}$), 7.37 (5H, s, aromatic -$\underline{H}$).

EXAMPLE 22

4-Nitrobenzyloxymethyl 9-N-benzylaminodeoxyclavulanate hydrochloride

9-N-Benzylaminodeoxyclavulanate (0.4 g) in dry dimethylformamide (15 cm$^3$) at room temperature was treated with 4-nitrobenzyloxymethylchloride (1 equivalent) and stirred for seven minutes. The solvent was evaporated in vacuo and acetone added (20 cm$^3$) followed by petroleum spirit (80°–100°) and diethyl ether (1:1, 200 cm$^3$), the mixture was cooled overnight and the resultant solid filtered off and washed with ether. Drying in vacuo afforded 4-nitrobenzyloxymethyl 9-N-benzylaminodeoxyclavulanate hydrochloride as an off-white solid (0.41 g). Rf (SiO$_2$/ethanol: chloroform, 1:4)=0.58. $\nu_{max}$ (film) 1805, 1755, 1700 cm$^{-1}$. δ(DMSO) 3.15 (1H, d, J 17 Hz, 6β-C$\underline{H}$) 3.62 (1H, dd, J 17 and 3 Hz, 6-α-C$\underline{H}$) 3.5 (2H, broad m, 9-C$\underline{H}_2$), 4.03 (2H, broad s, sharp s on shaking with D$_2$O, NC$\underline{H}_2$C$_6$H$_5$), 4.86 (2H, s, CH$_2$OC$\underline{H}_2$C$_6$H$_5$NO$_2$), 4.96 (1H, t, J 7 Hz, 8C$\underline{H}$), 5.37 (1H, s, 3C$\underline{H}$), 5.45 (2H, s, C$\underline{H}_2$OCH$_2$C$_6$H$_4$NO$_2$), 5.70 (1H, d, J 3 Hz, 5α-C$\underline{H}$), 7.27–7.60 (7H, m, CH$_2$C$_6$$\underline{H}_5$ and protons meta to nitro group of nitrobenzyl), 8.12 (2H, d, J 9 Hz, protons ortho to nitro group of nitrobenzyl), 9.72 (2H, broad s, exchanges with D$_2$O, N$\underline{H}_2^\oplus$).

EXAMPLE 23

9-N-Benzylaminodeoxyclavulanic acid p-toluene sulphonate

9-N-Benzylaminodeoxyclavulanic acid (288 mg) was suspended in benzyl alcohol (15 ml) and p-toluene sulphonic acid (190 mg) added to form the title compound.

EXAMPLE 24

Benzyl 9-N-benzylaminodeoxyclavulanate p-toluene sulphonate

Dicyclohexylcarbodiimide (206 mg) was added to the solution obtained in Example 23 and the mixture stirred at room temperature overnight. The solution was loaded onto a column of silica gel and the product obtained by gradient elution with chloroform/ethanol, finally eluting with 10:1. The title compound was obtained as a white solid on trituration with acetone/ether. $\nu_{max}$ (Nujol) 1810, 1750, 1700 cm$^{-1}$.

EXAMPLE 25

Ethyl 9-N-benzylaminodeoxyclavulanate p-toluene sulphonate

9-N-Benzylaminodeoxyclavulanic acid (288 mg) was suspended in ethanol (15 ml) and p-toluene sulphonic acid (190 mg) added to form the acid addition salt. Dicyclohexylcarbodiimide (206 mg) was added to the solution and the reaction mixture stirred for several hours at room temperature. The solvent was removed and the product purified by column chromatography on silica gel, eluting with butanol/propan-2-ol/water 4:4:1. Fractions containing the title compound were combined and evaporated; addition of ethanol and ether to the residue gave the product as a white solid which was filtered off and dried. ν(Nujol mull) 1810, 1750, 1700 cm$^{-1}$.

EXAMPLE 26

Phenacyl 9-N-benzylaminodeoxyclavulanate hydrobromide

9-N-Benzylaminodeoxyclavulanic acid (288 mg) in dimethylformamide (15 ml) was treated with phenacyl bromide (199 mg) and the resulting solution stirred at room temperature for 1½ hours. The dimethylformamide was evaporated in vacuo, the residue chromatographed on silica gel, and the title compound was eluted with chloroform/ethanol, 10:1. Evaporation of the fractions followed by trituration with acetone/ether gave the required salt as a pale yellow solid. $\nu_{max}$(KBr) 1798, 1755, 1698 cm$^{-1}$

EXAMPLE 27

Phenacyl 9-N-benzylaminodeoxyclavulanate hydroiodide

Phenacyl bromide (199 mg) was dissolved in acetone (2 ml) and a solution of sodium iodide (1.1 equivalent) in acetone (2 ml) added. An immediate precipitate of sodium bromide was obtained. After stirring the mixture for 10 minutes, the precipitate was filtered off and the filtrate added to a suspension of 9-N-benzylaminodeoxyclavulanic acid (288 mg) in dimethylformamide (15 ml). The solution was stirred at room temperature for 2 hours and the solvent removed. Fractionation of the crude product on silica gel, eluting with chloroform:ethanol, 10:1, gave the title compound. Work-up and trituration with acetone/ether gave the product as a pale yellow solid. $\nu_{max}$ (Nujol) 1800, 1750, 1695 cm$^{-1}$.

EXAMPLE 28

Lithium 9-N-carbobenzoxy-N-benzylaminodeoxyclavulanate

9-N-Benzylaminodeoxyclavulanic acid (1.15 g) in dimethylformamide (20 ml) containing one equivalent of lithium bicarbonate (544 mg; 10.8 ml 5% solution) was treated dropwise with a solution of benzylchloroformate (684 mg) in acetone (10 ml) at 0°. The reaction mixture was stirred at this temperature for 1 hour. The solvent was removed and the residue triturated with acetone/ether, the resulting white solid lithium 9-N-carbobenzoxy-N-benzylaminodeoxyclavulanate was filtered off and dried in a desiccator in vacuo (1.6 g). Rf (SiO$_2$: n-butanol: isopropanol: water; 7:7:6)=0.66; $[\alpha]_D^{20}$=+28.3° (C=1.6; water); $\nu_{max}$ (nujol) 1778, 1682, 1620 cm$^{-1}$, δ((CD$_3$)$_2$SO) 2.68 (1H, d, J 17.5 Hz, 6β-C$\underline{H}$), 3.42 (1H, dd, obscured by water peak, 6α-C$\underline{H}$), 3.8 (2H, d, J 7.5 Hz, 9-C$\underline{H}_2$), 4.32 (2H, s, NC$\underline{H}_2$C$_6$H$_5$), 4.52 (2H, m, 3-C$\underline{H}$ and 8-CH), 5.07 (2H, s, N.CO.O.C$\underline{H}_2$), 5.52 (1H, d, J 3 Hz, 5-C$\underline{H}$), 7.21 (5H, s, aromatic-$\underline{H}$), 7.28 (5H, s, aromatic-$\underline{H}$).

EXAMPLE 29

Methyl 9-N-carbobenzoxy-N-benzylaminodeoxyclavulanate

Lithium 9-N-Carbobenzoxy-N-benzylaminodeoxyclavulanate (428 mg) was dissolved in dimethylformamide (10 ml) and methyl iodide (710 mg) added. The reaction mixture was stirred at room temperature for 4 hours. The solvent was removed and the residue chromatographed on silica gel eluting with ethyl acetate: cyclohexane (1:1). The title compound was obtained after evaporation of the solvent as a colourless oil (244 mg). Rf (Ethylacetate-cyclohexane; 1:1)=0.75; $[\alpha]_D^{20}$=+13.21° (C=1.12; MeOH); $\nu_{max}$ (film) 1805, 1750, 1690 cm$^{-1}$; δ(CDCl$_3$) 2.86 (1H, d, J 17.5 Hz, 6β-CH), 3.42 (1H, dd, J 17.5 and 3 Hz, 6α-C$\underline{H}$), 3.72 (3H (3H, s, CO$_2$C$\underline{H}_3$), 3.96 (2H, d, J 7.5 Hz, CH.C$\underline{H}_2$N), 4.44 (2H, s, NC$\underline{H}_2$Ph), 4.67 (1H, bt, J 7.5 Hz, C$\underline{H}$CH$_2$), 4.94 (1H, d, J 1.5 Hz, 3-C$\underline{H}$), 5.16 (2H, s, CO$_2$C$\underline{H}_2$Ph), 5.53 (1H, d, J 3 Hz, 5-C$\underline{H}$), 7.22, 7.3 (10H, 2×s, Ar-$\underline{H}$).

EXAMPLE 30

Ethyl 9-N-carbobenzoxy-N-benzylaminodeoxyclavulanate

Ethyl iodide (780 mg) was added to a solution of lithium 9-N-carbobenzoxy-N-benzylaminodeoxyclavulanate (428 mg) in dimethylformamide (10 ml) containing about 2 drops water. The solution was allowed to stir at room temperature for seven hours. The solvent was removed by evaporation and the residue chromatographed on silica gel. The product was isolated by elution with ethyl acetate: cyclohexane; 1:1 and was obtained after evaporation of the solvent as a colourless oil (307 mg). Rf (ethyl acetate: cyclohexane; 1:1)=0.78; $[\alpha]_D^{20} = +9.6°$ (C=1.38; MeOH); $\nu_{max}$ (film) 1802, 1745, 1695 cm$^{-1}$; $\delta$(CDCl$_3$) 1.25 (3H, t, J 8 Hz, CH$_2$CH$_3$), 2.86 (1H, d, J 17.5 Hz, 6$\beta$-CH), 3.41 (1H, dd, J 17.5 Hz and 3 Hz, 6$\alpha$-CH), 3.96 (2H, d, J 8 Hz, CHCH$_2$N), 4.17 (2H, q, J 8 Hz, CH$_2$CH$_3$), 4.43 (2H, s, NCH$_2$C$_6$H$_5$), 4.92 (1H, d, J 1.5 Hz, 3-CH), 4.67 (1H, bt, J 8 Hz, 8-CH), 5.17 (2H, s, CO.O.CH$_2$C$_6$H$_5$), 5.53 (1H, d, J 3 Hz, 5-CH), 7.23, 7.30 (10H, 2×s, Ar-H).

EXAMPLE 31

Methyl 9-N-benzylaminodeoxyclavulanate hydrogen L-malate

Methyl 9-N-benzyloxycarbonyl-N-benzylaminodeoxyclavulanate (218 mg) in tetrahydrofuran (15 ml) and water (1 ml) was hydrogenated at N.T.P. in the presence of L-malic acid (67 mg) and 10% palladium on carbon (73 mg) for two hours. The catalyst was removed by filtration and the filtrate evaporated to dryness. Trituration with propan-2-ol/ether gave the title salt as an off-white solid. $\nu_{max}$ (Nujol) 1800, 1745, 1695, 1625 cm$^{-1}$.

EXAMPLE 32

Ethyl 9-N-benzylaminodeoxyclavulanate hydrogen L-malate

A solution containing ethyl 9-N-benzyloxycarbonyl-N-benzylaminodeoxyclavulanate (140 mg) and L-malic acid (42 mg) in tetrahydrofuran (15 ml) and water (1 ml) was hydrogenated over 10% palladium on carbon (45 mg) at N.T.P. for two hours. The catalyst was filtered off, washed with water and the filtrate evaporated. Trituration of the residue with propan-2-ol/ether gave the product as an off-white solid. $\nu_{max}$ (Nujol) 1800, 1745, 1695, 1630 cm$^{-1}$.

EXAMPLE 33

Benzyloxycarbonylmethyl 9-N-benzyloxycarbonyl-N-benzylaminodeoxyclavulanate

9-N-Benzyloxycarbonyl-N-benzylaminodeoxyclavulanic acid lithium salt (428 mg) was suspended in dimethylformamide (15 ml) and three drops of water added; benzyl bromoacetate (343 mg) was added to the resulting solution and the reaction mixture stirred at room temperature for five hours. Thin layer chromatography showed the reaction to be complete, the solvent was removed and the residue chromatographed on silica gel, eluting with ethyl acetate/cyclohexane (1:1). The combined fractions were evaporated in vacuo to yield a colourless oil (384 mg). Rf (SiO$_2$:ethyl acetate:cyclohexane, 1:1)=0.71; $[\alpha]_D^{20} = +12.2°$ (C=1.16; MeOH); $\nu_{max}$ (film) 1805, 1750 (b), 1705 (sh), 1690 cm$^{-1}$; $\delta$(CDCl$_3$) 2.86 (1H, d, J 17.5 Hz, 6$\beta$-CH), 3.38 (1H, dd, J 17.5 and 3 Hz, 6$\alpha$-CH), 3.94 (2H, d, J 8 Hz, 9-CH$_2$). 4.44 (2H, s, NCH$_2$Ph), 4.65 (2H, s, CO$_2$CH$_2$CO$_2$), 4.74 (1H,bt, partially obscured by signal at 4.65), 5.04 (1H, d, J, 1.5 Hz, 3-CH), 5.15 (4H, s, NCO$_2$CH$_2$Ph and CH$_2$CO$_2$CH$_2$Ph), 5.52 (1H, d, J 3 Hz, 5-CH), 7.22, 7.29 (15H, 2×s, aromatic -H).

EXAMPLE 34

2-Hydroxyethyl 9-N-benzyloxycarbonyl-N-benzylaminodeoxyclavulanate

2-Iodoethanol (860 mg) was added to a solution of lithium 9-N-benzyloxycarbonyl-N-benzylaminodeoxyclavulanate (428 mg) in dimethylformamide (15 ml) and water (3 drops). The solution was stirred for 14 hours at room temperature and the solvent removed; the residue was purified by column chromatography on silica gel, eluting with ethyl acetate/cyclohexane, 1:1. The product was obtained as a colourless oil. Rf (SiO$_2$:ethyl acetate:cyclohexane, 1:1)=0.29; $\nu_{max}$ (film) 1800, 1745, 1700 cm$^{-1}$.

EXAMPLE 35

Methyl 9-N-benzylaminodeoxyclavulanate hydrogen succinate

Methyl 9-N-benzyloxycarbonyl-N-benzylaminodeoxyclavulanate (109 mg) was dissolved in tetrahydrofuran/methanol (10 ml) and hydrogenated at N.T.P. over 10% palladium on carbon (38 mg). The catalyst was filtered off and the solvent evaporated to yield the product as a gum. $\nu_{max}$ (film) 1800, 1740, 1695, 1615 cm$^{-1}$.

EXAMPLE 36

Methyl 9-N-benzylaminodeoxyclavulanate hydrogen L-tartrate

Methyl 9-N-benzyloxycarbonyl-N-benzylaminodeoxyclavulanate (87 mg) in tetrahydrofuran (10 ml) and water (1 ml) was hydrogenated at atmospheric pressure in the presence of (+)-tartaric acid (30 mg) and 10% palladium on carbon (30 mg) for ½ hour. The mixture was filtered through celite, the catalyst washed with water, and the filtrate was evaporated to dryness. Trituration of the residue with acetone/ether gave the product as a white solid. $\nu_{max}$ (Nujol) 1797, 1743, 1700, 1620 cm$^{-1}$.

EXAMPLE 37

Benzyl 9-N-(2'-methylallyl)benzylaminodeoxyclavulanate

Benzyl dichloroacetylclavulanate (5 g; 12.5 mM) in dimethylformamide (70 cm$^3$) at 0° was treated with N-(2-methylallyl)benzylamine (1.9 equivalents) dropwise with stirring. The mixture was stirred for 3 hours at 0° then poured into ethylacetate (250 cm$^3$) and washed with water (5×150 cm$^3$) and saturated brine (5×100 cm$^3$) dried (anhydrous magnesium sulphate) and evaporated in vacuo to yield an oil. This crude product was chromatographed on silica eluting with cyclohexane/ethylacetate; 1:1. Fractions (detected by aqueous potassium permanganate spray) were collected containing the title compound Rf (SiO$_2$/ethylacetate:cyclohexane; 1:1)=0.84. Combined fractions were evaporated to yield an oil 2.8 g (36%). $\nu$(film) 1805, 1750, 1695, 1495, 1455, 1308, 1230, 1175, 1120, 1015, 895, 745, 700 cm$^{-1}$. $\delta$(CDCl$_3$) 1.70 (3H, s), 2.85 (2H, s), 2.76-3.10 (1H, d), 3.08 (2H, J 7 Hz), 3.40 (1H, dd, J 17 and 3 Hz) 3.41 (2H, s), 4.71 (1H, t, J 7 Hz), 4.75-4.95 (2H, broad m), 5.03 (1H, broad s) 5.15 (2H, s) 5.57 (1H, d, J 3 Hz), 7.25 and 7.30 (10 H, 2×s).

The intermediate N-(2-methylallyl)benzylamine was prepared as follows:

Benzaldehyde (7.42 g; 70 mM) in 150 cm$^3$ of a solvent mixture of ethylacetate/chloroform/ethanol was treated with 1 equivalent of 2-methylallyl amine and stirred for ½ hour. The mixture was treated with a slight excess of sodium borohydride and stirred for ½ hour. The solvent was removed by evaporation in vacuo and the residue was redissolved in ethylacetate (200 cm$^3$)

then washed with water (3×100 cm³). The free amine was extracted into aqueous hydrochloric acid, the aqueous phase was washed with ethyl acetate (2×100 cm³). Fresh ethylacetate was added (150 cm³) and stirred vigorously with sodium carbonate until alkaline. The ethylacetate phase containing the free amine was washed with water (5×100 cm³) and saturated brine (3×100 cm³), dried (anhydrous magnesium sulphate) and evaporated to a mobile colourless liquid, yield=8.1 g (72%) ν(film) 3330, 1650, 1495, 1450, 1115, 1030, 895, 735, 700 cm⁻¹. δ(CDCl₃) 1.40 (1H, s, exchanges with D₂O), 1.74 (3H, s) 3.15 (2H, s) 3.70 (2H, s) 4.76–4.95 (2H, m), 7.25 (5H, m). C₁₁H₁₅N requires 161.1180; 161.1192 found.

EXAMPLE 38

9-N-Benzylaminodeoxyclavulanic acid

Benzyl 9-N-(2-methylallyl)benzylaminodeoxyclavulanate (0.5 g) was hydrogenolysed in neat ethanol (30 cm³) in the presence of palladium on carbon (10%; 0.2 g; prehydrogenated for 20 minutes) for 25 minutes at atmospheric pressure. The catalyst was filtered off and washed with ethanol (10 cm³), the catalyst was then washed with aqueous ethanol (50%; 150 cm³), this aqueous ethanolic wash was collected separately and evaporated to yield a white crystalline solid. This solid was washed with cold (0°) ethanol and dried to yield 164 mg (49%) of the title compound. Rf (SiO₂/butanol-propan-2-ol-water; 7:7:6)=0.45 (detection by aqueous potassium permanganate spray). ν(Nujol) 1815, 1690, 1612, 1575, 1305, 1187, 1125, 1082, 1065, 1045, 1035, 1018, 1005, 990, 950, 892, 750, 685 cm⁻¹.

EXAMPLE 39

Benzyl 9-N-(4'-acetamidobenzyl)-N-(2'-methylallyl) aminodeoxyclavulanate

Benzyl dichloroacetyl clavulanate (3.2 g; 8 mm), in dry dimethylformamide (30 cm³) at 0° C. was treated with 1.9 equivalents of N-(4-acetamidobenzyl)-N-(2'-methylallyl)amine and stirred for 2¼ hours at 0° C. The mixture was poured into ethyl acetate (250 cm³) and washed with water (4×100 cm³) and saturated brine (4×100 cm³), dried (anhydrous magnesium sulphate) and evaporated to an oil. This oil was chromatographed on silica gel eluting with ethyl acetate. Fractions were collected containing the title compound, Rf (SiO₂/ethylacetate/cyclohexane 1:1)=0.33 (detection by aqueous potassium permanganate spray). Combined fractions were evaporated to give a foam, yield=1.92 g (49%), ν(film) 3320 (broad), 1805, 1750, 1695, 1670, 1605, 1535, 1515, 1455, 1415, 1370, 1310, 1265, 1230, 1175, 1120, 1040, 1020, 895, 830, 750, 700 cm⁻¹, δ(CDCl₃) 1.69 (3H, s), 2.12 (3H, s), 2.84 (2H, s), 2.75–3.07 (1H, m), 3.06 (2H, d, J 7 Hz), 3.36 (2H, s), 3.40 (1H, dd, J 17 and 3 Hz), 4.69 (1H, t, J 7 Hz), 4.74–4.98 (2H, broad m), 5.02 (1H, s), 5.15 (2H, s), 5.58 (1H, d, J 3 Hz), 7.13–7.45 (10H, m).

EXAMPLE 40

9-N-(4'-Acetamidobenzyl)aminodeoxyclavulanic acid

Benzyl 9-N-(4'-acetamidobenzyl)-N-(2'-methylallyl) aminodeoxyclavulanate (1.14 g; 2.33 mm) in tetrahydrofuran-ethanol (1:1; 40 cm³) was hydrogenolysed for 4 hours at atmospheric pressure in the presence of 10% palladium on carbon (0.3 g). The catalyst was filtered and washed with aqueous ethanol (30 cm³) and the filtrate evaporated to an oil. This oil was dissolved in tetrahydrofuran-ethanol (50%; 10 cm³) and cooled (0°) slowly; crystals formed which were filtered off and washed with cold (0°) tetrahydrofuran-ethanol mixture (1:1) and dried to yield the title compound as white crystals, yield=172 mg (21%) Rf (SiO₂/butanol-propan-2-ol-water; 7:7:6)=0.45.

ν(NUJOL) (1810–1790), 1692, 1675, 1600 cm⁻¹. δ(D₂O) 2.12 (3H, s), 3.04 (1H, d, J 17 Hz), 3.53 (1H, dd, J 17 Hz and 3 Hz), 3.69 (2H, d, J 7 Hz), 4.12 (2H, s), 4.76 (1H, t, J 7 Hz), 4.94 (1H, s), 5.69 (1H, d, J 3 Hz), 7.40 (4H, s).

EXAMPLE 41

Benzyl 9-N-(2'-methyl-3'-phenylallyl)ethylaminodeoxyclavulanate

Benzyl dichloroacetylclavulanate (5 g; 12.5 mM) in dry dimethylformamide (70 cm³) at −10° was treated with 1.9 equivalents of N-ethyl-N-(2-methyl-3-phenylallyl)amine and stirred for 30 minutes allowing the temperature to rise slowly to −2°. The mixture was poured into iced ethylacetate (250 cm³) and washed with water (5×100 cm³) and saturated brine (5×100 cm³), dried (anhydrous magnesium sulphate) and evaporated to an oil. This oil was dissolved in toluene (15 cm³) and chromatographed on silica eluting with ethyl acetate-cyclohexane; 1:2. Fractions were collected containing the title compound, Rf (SiO₂/ethyl acetate-cyclohexane; 1:1)=0.5 (detection by aqueous potassium permanganate spray). Combined fractions were evaporated to yield an oil; 1.4 g (25%), ν(film) 1805, 1750, 1700, 1308, 1175, 1015, 745, 700 cm⁻¹. δ(CDCl₃) 1.00 (3H, t, J 7 Hz), 1.84 (3H, d, J 1 Hz), 2.42 (2H, q, J 7 Hz), 2.93 (1H, d, J 17 Hz), 2.96 (2H, s), 3.17 (2H, d, J 7 Hz), 3.39 (1H, dd, J 17 and 3 Hz), 4.73 (1H, t, J 7 Hz), 5.16 (1H, s), 7.25 and 7.32 (10H, 2×broad s).

EXAMPLE 42

9-N-Ethylaminodeoxyclavulanic acid

Benzyl 9-N-(2'-methyl-3'-phenylallyl)ethylaminodeoxyclavulanate (0.71 g; 1.59 mM) in ethanol (40 cm³) was hydrogenolysed at atmospheric pressure in the presence of palladium on carbon (10%), 250 mg (which had been prehydrogenated for 15 minutes) for 1 hour. The catalyst was filtered off and washed with aqueous ethanol (50 cm³), the filtrate was evaporated and ethanol was added, the resulting crystalline solid was filtered off cold (0°) and washed with a little cold ethanol. Drying afforded the title compound as a white crystalline solid, yield=78 mg. The filtrate was again evaporated, cold methanol was added and the resulting crystalline solid filtered off, washed with cold methanol and dried to yield a further 10 mg of the title compound; total yield=88 mg (24%). Rf (SiO₂/butanol-isopropanol-water; 7:7:6)=0.38 (detection by aqueous potassium permanganate spray). ν(Nujol) (3700–2000) very broad, 1808, 1695, 1620, 1585, 1302, 1190, 1120, 1045, 1020, 1008, 925, 895, 870, 802, 750 cm⁻¹. ν(KBr) (3700–3140), (3140–2890), (2890–2600), (2540–2100), 1790, 1690 (1675–1510), 1470, 1390, 1375, 1300, 1185, 1118, 1042, 1018, 920, 895, 803, 752 cm⁻¹. δ(D₂O) 1.21 (3H, t, J 7 Hz), 3.02 (2H, q, J 7 Hz), 3.07 (1H, d, J 17 Hz), 3.56 (1H, dd, J 17 and 3 Hz), 3.68 (2H, d, J 7.5 Hz), 4.77 (1H, broad, t, J 7.5 Hz), 4.96 (1H, s), 5.74 (1H, d, J 3 Hz).

EXAMPLE 43

Benzyl 9-N-(2''-methylallyl)-N-(1',2',3',6'-tetrahydrobenzyl-)aminodeoxyclavulante Benzyl dichloroacetylclavulanate (6 g; 15 mM) in dry dimethylformamide (40 cm³) at 0° was treated with N-(2''-methylallyl)-N-(1',2',3',6'-tetrahydrobenzyl) amine (1.9 equivalents) and stirred at 0° for 1½ hours. The mixture was poured into ethyl acetate (200 cm³) and washed with water (5×100 cm³) and saturated brine (5×100 cm³), dried (anhydrous magnesium sulphate) and evaporated to yield an oil. This oil was chromatographed on silica gel eluting with ethyl acetate-cyclohexane; 1:1. Fractions were collected containing the title compound, Rf (SiO₂/ethylacetate-cyclohexane; 1:1)=0.9 (detection by aqueous potassium permanganate spray). Combined fractions were evaporated to an oil, yield=3.2 g (48%). ν(film) 1805, 1750, 1695, 1450, 1305, 1175, 1120, 1042, 1010, 895, 745, 700, 655 cm⁻¹. δ(CDCl₃) 1.00–2.30 (7H, broad m), 1.67 (3H, s), 2.14 (2H, d, J 6 Hz), 2.80 (2H, s), 2.96 (1H, d, J 17 Hz), 3.10 (2H, d, J 7 Hz), 3.42 (1H, dd, J 17 and 3 Hz), 4.68 (1H, t, J 7 Hz), 4.7–4.9 (2H, broad m), 5.04 (1H, s), 5.16 (2H, s), 5.58–5.70 (3H, broad m), 7.32 (5H, s).

EXAMPLE 44

9-N-Hexahydrobenzylaminodeoxyclavulanic acid

Benzyl 9-N-(2''-methylallyl)-N-(1',2',3',6'-tetrahydrobenzyl)aminodeoxyclavulanate (1.26 g; 2.9 mM) in ethanol (50 cm³) was hydrogenolysed at atmospheric pressure for 40 minutes in the presence of palladium on carbon (10%) (400 mg) which had been prehydrogenated for 1½ hour. The catalyst was filtered off and washed with ethanol (20 cm³) then with 50% aqueous ethanol (100 cm³). This aqueous washing was evaporated to yield a white crystalline solid. This solid was slurried in cold ethanol and filtered off, washed with a few cm³ of cold (0°) ethanol and dried to yield 0.41 g (48%) of the title compound. Rf (SiO₂/butanol-propan-2-ol-water; 7:7:6)=0.6 (detection by aqueous potassium permanganate spray). ν(Nujol) 1805, 1692, 1610 (broad), 1590 (broad), cm⁻¹. ¹H nuclear magnetic resonance showed that the cyclohexenyl C=C was only partially reduced. The mixed zwitterionic products were dissolved in 50% aqueous ethanol (40 cm³) and hydrogenated in the presence of 110 mg palladium on carbon (10%) for 3 hours at atmospheric pressure, filtered and the catalyst washed with aqueous ethanol (20 cm³), the filtrate was evaporated to yield a white crystalline solid, ethanol was added (20 cm³) and cooled (0°). The solid was filtered off and washed with cold ethanol, dried to yield 0.3 g (30%) of the title compound. ν(Nujol) 1805, 1695, 1610 (broad), 1305, 1190, 1120, 1080, 1070, 1050, 1020, 1008, 950, 900, 850, 810, 760 cm⁻¹. δ(D₂O) 0.6–2.0 (11H, broad m), 2.83 (2H, d, J 6 Hz), 3.07 (1H, d, J 17 Hz), 3.55 (1H, dd, J 17 and 3 Hz), 3.67 (2H, d, J 7 Hz), 4.75 (1H, t, J 7 Hz), 4.95 (1H, s), 5.73 (1H, d, J 3 Hz).

EXAMPLE 45

Benzyl 9-N-(2'-methylallyl)-N-(n-propyl)aminodeoxyclavulanate

To a solution of benzyl dichloroacetylclavulanate (8.0 g, 20 mmol) in dimethylformamide (100 ml) at −10° C. was added N-(2'methylallyl)-N-(n-propyl)amine (4.3 g, 38 mmol) in dimethylformamide (15 ml). After 30 mins at −10° C. the reaction mixture was poured into ethyl acetate and extracted with water (4×). The organic phase was washed with brine, dried (MgSO₄) and evaporated to a yellow oil which was chromatographed on silica gel. The title ester was obtained on elution with petrol/ethyl acetate: 1/1 grading to ½. Yield, as an oil, 4.2 g (55%).

I.R. (CDCl₃) 2950, 1800, 1745, 1695 and 900 cm⁻¹
N.M.R. (CDCl₃) 0.81 (3H, t, J 7 Hz), 1.41 (2H, sextet, J 7 Hz), 1.68 (3H, s), 2.23 (2H, t, J 7 Hz), 2.81 (2H, s), 2.96 (1H, d, J 17 Hz), 3.10 (2H, d, J 7 Hz), 3.44 (1H, dd, J 17 and 3 Hz), 4.69 (1H, bt, J 7 Hz), 4.80 (2H, bs), 5.05 (1H, s), 5.16 (2H, s) 5.63 (1H, d, J 3 Hz), and 7.34 (5H, s).

EXAMPLE 46

9-N-(n-Propyl)aminodeoxyclavulanic acid

A mixture of tetrahydrofuran (150 ml) and water (15 ml) containing 10% Pd on carbon (1.6 g) was hydrogenated at atmospheric pressure for 20 mins. Benzyl 9-N-(2'-methylallyl)-N-(n-propyl)aminodeoxydeoxyclavulanate (3.9 g, 10.2 mmol) in tetrahydrofuran (15 ml) was added and the hydrogenation was continued for 40 mins. The catalyst was filtered off (celite) and the filter cake was washed which crystallised on trituration with iso-propanol. Yield=0.190 g.

The filter-pad from above was now washed with 50% aqueous ethanol. Evaporation and trituration with iso-propanol afforded the title compound as a white solid (0.91 g). Total yield of title compound=1.1 g (45%).

I.R. (KBr) 3540–3370, 2960, 1795, 1780, 1700 and 1615 cm⁻¹.

N.M.R. (D₂O) 0.90 (3H, t, J 7 Hz), 1.64 (2H, sextet, J 7 Hz), 2.94 (2H, t, J 7 Hz), 3.09 (1H, d, J Hz), 3.56 (1H, dd, J 17 and 3 Hz), 3.69 (2H, d, J 7 Hz), 4.78 (1H, bt, J 7 Hz), 4.97 (1H, s), and 5.75 (1H, d, J 3 Hz).

EXAMPLE 47

Benzyl 9-N-(n-butyl)-N-(2'-methyl-3'-phenylallyl)aminodeoxyclavulanate

Benzyl 9-O-dichloroacetylclavulanate (9.33 g; 23.3 mmol) in dry dimethylformamide (90 ml) was stirred and cooled to −10° C. N-(n-Butyl)-N-(2'-methyl-3'-phenylallyl)amine (9 g; 44.3 mmol) in dry dimethylformamide (90 ml) was then added dropwise. The solution was then stirred at −10° C. for 30 minutes.

The solution was then poured into an ethyl acetate/water mixture and shaken. The two layers were then separated and the aqueous phase was extracted with more ethyl acetate. The combined organic phases were then washed with water, brine, dried (MgSO₄), filtered and evaporated under a reduced pressure to give a dark yellow oil. Column chromatography through silica-gel eluting with ethylacetate petroleum ether 1:2 gave the title compound as a light yellow oil in a 35% yield.

νmax (CHCl₃): 1800, 1750, 1720 and 1640 cm⁻¹
δ(CDCl₃): 0.70→1.05 (3H, m) 1.06→1.68 (4H, m), 1.85 (3H, s), 2.19→2.51 (2H, m), 2.90 (1H, d, J 17 Hz), 2.97 (2H, s), 3.19 (2H, d, J 7 Hz), 3.39 (1H, dd, J 17 and 3 Hz), 4.75 (1H, t, J 7 Hz), 5.09 (1H, s), 5.17 (2H, s), 5.62 (1H, d, J 3 Hz), 6.83 (1H, br, s), and 7.02→7.54 (10H, m).

EXAMPLE 48

9-N-(n-Butyl)-aminodeoxyclavulanic acid

Benzyl 9-N-(n-butyl)-N-(2-methyl-3-phenylallyl)aminodeoxyclavulanate (3.80 g, 8 mmole) in tetrahydrofuran (T.H.F.) (40 ml) was added to a prehydrogenated mixture of 10% palladium on charcoal (2 g) in 10% aqueous T.H.F. The mixture was then hydrogenated at atmospheric pressure for 1 hour.

The catalyst was then filtered through a celite pad and th 'cake' washed with 10% aqueous T.H.F. and then with 50% aqueous ethanol. The filtrate was then evaporated to dryness under a reduced pressure and T.H.F. added. The white crystalline solid was then filtered off and from the spectral data obtained found to be the title compound in 30% yield.

$\nu$max (KBr): 1800, 1784, 1695, and 1610 cm$^{-1}$ $\delta(D_2O)$: 1.01 (3H, m), 1.57 (4H, m), 3.12 (2H, t, J Hz), 3.25 (1H, d, J 17 Hz), 3.75 (1H, dd, J 17 and 3 Hz), 3.83 (2H, d, J 7 Hz), 4.93 (1H, broad, t, J 7 Hz), 5.14 (1H, s), and 5.88 (1H, d, J 3 Hz).

EXAMPLE 49

Benzyl 9-N-(2'-methylallyl)-N-(3''-methylallyl)aminodeoxyclavulanate

Benzyl dichloroacetylclavulanate (7.4 g; 18.5 mM) in dry dimethylformamide (50 cm$^3$) at 0° was treated with N-(2'-methylallyl)-N-(3''-methylallyl) amine (1.9 equivalents) and stirred at 0° for 45 minutes. The mixture was poured into ethyl acetate (200 cm$^3$) and washed with water (6×100 cm$^3$) and saturated brine (6×100 cm$^3$), dried (anhydrous magnesium sulphate) and evaporated to an oil. This oil was chromatographed on silica eluting with ethyl acetate-cyclohexane (1:2), fractions were collected Rf (SiO$_2$/ethyl acetate-cyclohexane; 1:2)=0.5 (detection by aqueous potassium permanganate spray). Combined fractions were evaporated to yield the title compound an oil, yield=2.7 g (37%), $\nu$(film) 1805, 1750, 1700, 1450, 1380, 1305, 1230, 1175, 1120, 1080, 1042, 1015, 970, 895, 740, 700 cm$^{-1}$. $\delta(CDCl_3)$ 1.58–1.80 (6H, m), 2.81 (4H, broads), 2.95 (1H, d, J 17 Hz), 3.08 (2H, d, J 7 Hz), 3.42 (1H, dd, J 17 and 3 Hz), 4.68 (1H, t, J 7 Hz), 4.79 (2H, broad s), 5.03 (1H, s), 5.15 (2H, s), 5.36–5.56 (2H, broad m), 5.60 (1H, d, J 3 Hz), 7.32 (5H, s).

EXAMPLE 50

9-N-n-Butylaminodeoxyclavulanic Acid

Benzyl 9-N-(2'-methylallyl)-N-(3''-methylallyl) aminodeoxyclavulanate (1.37 g); in ethanol (30 cm$^3$) was hydrogenolysed at atmospheric pressure in the presence of palladium on carbon, 10% (0.5 g, prehydrogenated for 20 minutes) for 25 minutes. The catalyst was filtered off and washed with aqueous ethanol (50 cm$^3$). The filtrate was evaporated, ethanol added and cooled (0°). A white crystalline solid was filtered off and dried (354 mg). Thin layer chromatography on silica showed that this solid was a mixture of 9-N-n-butylaminodeoxyclavulanic acid and 9-N-isobutylaminodeoxyclavulanic acid and 9-N-isobutylaminodeoxyclavulanic acid, the former being present as the major constituent, and less polar Rf (SiO$_2$-butanol-propan-2-ol-water: 7:7:6)=0.53 than the iso derivative Rf=0.50. The mixture was chromatographed on cellulose eluting with butanol-propan-2-ol-water; 8:8:1. Fractions were collected containing the title compound Rf=0.53. Combined fractions were evaporated to a white crystalline solid, 25 mg. $\nu$(Nujol) (2800-2100), 1805, 1690, 1600 (broad), 1300, 1182, 1110, 1080, 1067, 1045, 1015, 1005, 940, 910, 892, 865, 805, 755 cm$^{-1}$.

$\epsilon(D_2O)$ 0.65–1.05 (3H, m) 1.05–1.82 (4H, m), 2.96 (2H, t, J 7 Hz), 3.07 (1H, d, J 17 Hz), 3.57 (1H, dd, J 17 and 3 Hz), 3.68 (2H, d, J 7 Hz), 4.76 (1H, t, J 7 Hz), 4.95 (1H, s), 5.73 (1H, d, J 3 Hz).

EXAMPLE 51

Benzyl 9-N-(3',4',5'-trimethoxybenzyl)-N-(2''-methylallyl)aminodeoxyclavulanate Benzyldichloroacetylclavulanate (5.49 g; 13.7 mM) in dry dimethylformamide (50 cm$^3$) at 0° C. was treated with N-(3,4,5-trimethoxybenzyl) 2'-methylallylamine (1.9 equivalents) dropwise with stirring. The mixture was stirred at 0° for 2 hours then poured into ethylacetate (250 cm$^3$) and washed with water (5×150 cm$^3$) and saturated brine (5×150 cm$^3$), dried (anhydrous magnesium sulphate) and evaporated to an oil. This oil was chromatographed on silica eluting with ethylacetate-cyclohexane; 1:2. Fractions were collected containing material Rf 0.78 (SiO$_2$/ethylacetate-cyclohexane; 1:1). Combined fractions were evaporated to yield the title compound as an oil; yield=2.4 g (34%). $\nu$(film) 1805, 1750, 1695, 1590, 1502, 1455, 1420, 1330, 1308, 1185, 1175, 1125, 1010, 895, 745, 700 cm$^{-1}$. $\delta(CDCl_3)$ 1.73 (3H, s), 2.85 (2H, s), 2.96 (1H, d, J 17 Hz), 3.13 (2H, d, J 7 Hz), 3.37 (2H, s), 3.45 (1H, dd, J 17 and 3 Hz), 3.82 (9H, s), 4.73 (1H, t, J 7 Hz), 4.86 (2H, broad s), 5.07 (1H, s), 5.18 (2H, s), 5.61 (1H, d, J 3 Hz), 6.54 (2H, s), 7.31 (5H, s).

EXAMPLE 52

9-N-(3',4',5'-Trimethoxybenzyl)aminodeoxyclavulanic acid

Benzyl 9-N-(3',4',5'-trimethoxybenzyl)-N-(2''-methylallyl)aminodeoxyclavulanate (2.0 g; 3.83 mM) in ethanol (50 cm$^3$) was hydrogenolysed at atmospheric pressure in the presence of palladium on carbon (10%), 0.6 g (prehydrogenated for 15 minutes) for 20 minutes, water (10 cm$^3$) was added and hydrogenolysis continued for 10 minutes. The catalyst was filtered off and washed with aqueous ethanol (30 cm$^3$) and the clear filtrate evaporated. Ethanol (30 cm$^3$) was added to yield a white crystalline solid. The solid was filtered off cold (0°) and washed with a little cold ethanol. Drying gave the title compound as a finely crystalline solid, yield=0.61 g (42%), Rf (SiO$_2$/butanol-propan-2-ol-water; 7:7:6)=0.55.

$\nu$(Nujol) 1805, 1695, 1615, 1595, 1300, 1250, 1192, 1165, 1130, 1045, 1008, 920, 895, 830, 782, 750 cm$^{-1}$, $\nu$(KBr) 1790, 1695, (1620-1590), 1510, 1464, 1427, 1385, 1334, 1300, 1247, 1190, 1160, 1123, 1040, 1020, 1005, 957, 920, 895, 850, 830, 783, 745 cm$^{-1}$. $\delta(D_2O)$ 2.99 (1H, d, J 17 Hz), 3.50 (1H, dd, J 17 and 3 Hz), 3.64 (2H, d, J 7 Hz), 3.72 (3H, s), 3.80 (6H, s), 4.05 (2H, s), 4.74 (1H, t, J 7 Hz), 4.92 (1H, s), 5.64 (1H, d, J 3 Hz), 6.72 (2H, s).

EXAMPLE 53

Benzyl 9,N,N-bis(2'-methylallyl)aminodeoxyclavulanate

Benzyl dichloroacetylclavulanate (5 g; 12.5 mm) in dry dimethylformamide (75 cm$^3$) at 0° was treated with bis(2-methylallyl)amine (1.9 equivalents) and stirred at 0° for 2 hours. The mixture was poured into ethylacetate (250 cm³) and washed with water (5×100 cm³) and saturated brine (5×100 cm³), dried (anhydrous magnesium sulphate) and evaporated to an oil. This oil was chromatographed on silica eluting with ethylacetatecyclohexane (1:1). Fractions were collected containing the title compound Rf (SiO₂/ethylacetate-cyclohexane; 1:1)=0.82 (detection by aqueous potassium permanganate spray). Combined fractions were evaporated to yield an oil, 1.46 g (29%).

ν(film) 1805, 1750, 1695, 895, 755, 700 cm⁻¹. δ(CDCl₃) 1.67 (6H, s), 2.78 (4H, s), 2.95 (1H, d, J 17 Hz), 3.03 (2H, d, J 7 Hz), 3.42 (1H, dd, J 17 and 3 Hz), 4.67 (1H, t, J 7 Hz), 4.80 (4H, broads), 5.03 (1H, s), 5.17 (2H, s), 5.61 (1H, d, J 3 Hz), 7.33 (5H, s).

EXAMPLE 54

9-N-Isobutylaminodeoxyclavulanic acid

Benzyl 9-N,N-bis(2'-methylallyl)aminodeoxyclavulanate (0.8 g; 2.02 mm) in ethanol (30 cm³) was hydrogenated in the presence of palladium on charcoal 10% (0.3 g) for 10 min at atmospheric pressure; the catalyst had been pre-hydrogenated for 20 minutes. The catalyst was filtered off and washed with aqueous ethanol (50 cm³), the filtrate was evaporated in vacuo and ethanol added, after cooling at 0° a crystalline solid was filtered off and washed with cold ethanol, drying in vacuo afforded the title compound as a white crystalline solid; yield=190 mg (37%) Rf (SiO₂/butanol-propan-2-ol-water; 7:7:6)=0.45 ν(Nujol) 1805, 1690, 1610, 1570, 1185, 1110, 1080, 1070, 1045, 1020, 1005, 930, 895, 885, 857, 810, 758 cm⁻¹. ν(KBr) 3570 (broad), 3350 (broad), 3220 (broad), 2840-2740, 2450 (broad), 1780, 1695, 1600 (very broad), 1470, 1392, 1320, 1295, 1110, 1045, 1020, 1003, 987, 932, 893, 885, 812, 750 cm⁻¹. δ(D₂O) 0.94 (6H, d, J, 6 Hz), 1.90 (1H, m), 2.82 (2H, d, J 6 Hz), 3.07 (1H, d, J 17 Hz), 3.57 (1H, dd, J 17 and 3 Hz), 3.70 (2H, d, J 17 and 3 Hz), 3.70 (2H, d, J 7 Hz), 4.77 (1H, t, J 7 Hz), 4.96 (1H, d), 5.73 (1H, d, J 3 Hz).

EXAMPLE 55

Benzyl 9-N-isobutyl-N-(2'-methyl-3'-phenylallyl)aminodeoxyclavulanate

Benzyl dichloroacetylclavulanate (7.16 g; 17.9 mM) in dry dimethylformamide (85 cm³) at −12° was treated with 1.9 equivalents of N-isobutyl-N-(2-methyl-3-phenylallyl) amine and stirred at −15° for 15 minutes then for 45 minutes between −10° and 0°. The mixture was poured into iced ethylacetate (250 cm³) and washed with water (5×100 cm³), saturated brine (5×100 cm³), dried (anhydrous magnesium sulphate) and evaporated in the presence of toluene to a small volume. This crude product was chromatographed on silica eluting with ethylacetate-cyclohexane; 1:2. Fractions were collected containing the title compound Rf (SiO₂/ethylacetate-cyclohexane; 1:2)=0.89. Combined fractions were evaporated to afford the title compound as as oil, yield=1.60 g (19%), ν(film) 1808, 1750, 1690, 745, 700 cm⁻¹. δ(CDCl₃) 1.85 (6H, d, J 6 Hz), 1.50–2.20 (6H, broad m), 2.92 (1H, d, J 17 Hz), 2.94 (2H, s), 3.39 (1H, dd, J 17 and 3 Hz), 4.73 (1H, broad, t, J 7 Hz), 5.07 (1H, broad s), 5.17 (2H, s), 5.60 (1H, d, J 3 Hz), 6.35 (1H, broad s), 7.25 and 7.32 (10H, 2×s).

EXAMPLE 56

9-N-Isobutylaminodeoxyclavulanic acid

Benzyl 9-N-(2'-methyl-3'-phenylallyl)-N-isobutylaminodeoxyclavulanate (1.44 g; 3.04 mM) in ethanol (25 cm³) was hydrogenolysed in the presence of palladium on carbon (10% Pd), 0.5 g (which had been prehydrogenated for 15 minutes), for 45 minutes at atmospheric pressure. The catalyst was filtered off and washed with ethanol (50 cm³), then with aqueous ethanol (100 cm³), the aqueous washing was collected separately and was evaporated to yield the title compound as a white crystalline solid. The solid was washed with a little cold ethanol, drying afforded 248 mg of the title compound. The ethanolic catalyst washing and the solvent from the hydrogenolysis were evaporated, ethanol added (10 cm³) and cooled, crystals were filtered off and dried to yield a further 17 mg of the title compound, total yield=265 mg (34%). The infrared and proton magnetic resonance spectra were identical to the product obtained by hydrogenolysis of benzyl 9-N-N-bis(2'-methylallyl)aminodeoxyclavulanate.

EXAMPLE 57

Benzyl 9-N-(2'-methylallyl)-N-(3''-methylallyl)aminodeoxyclavulanate

Benzyl dichloroacetylclavulanate (7.4 g; 18.5 mM) in dry dimethylformamide (50 cm³) at 0° was treated with N-(2'-methylallyl)-N-(3''-methylallyl) amine (1.9 equivalents) and stirred at 0° for 45 minutes. The mixture was poured into ethyl acetate (200 cm³) and washed with water (6×100 cm³) and saturated brine (6×100 cm³), dried (anhydrous magnesium sulphate) and evaporated to an oil. This oil was chromatographed on silica eluting with ethyl acetate-cyclohexane (1:2), fractions were collected Rf (SiO₂/ethyl acetate-cyclohexane; 1:2)=0.5 (detection by aqueous potassium permanganate spray). Combined fractions were evaporated to yield the title compound as an oil, yield=2.7 g (37%). ν(film) 1805, 1750, 1700, 1450, 1380 1305, 1230, 1175, 1120, 1080, 1042, 1015, 970, 895, 740, 700 cm⁻¹. δ(CDCl₃) 1.58–1.80 (6H, m), 2.81 (4H, broads), 2.95 (1H, d, J 17 Hz), 3.08 (2H, d, J 7 Hz), 3.42 (1H, dd, J 17 and 3 Hz), 4.68 (1H, t, J 7 Hz), 4.79 (2H, broad s), 5.03 (1H, s), 5.15 (2H, s), 5.36–5.56 (2H, broad m), 5.60 (1H, d, J 3 Hz), 7.32 (5H, s).

EXAMPLE 58

9-N-Isobutylaminodeoxyclavulanic acid

Benzyl 9-N-(2'-methylallyl)-N-(3'-methylallyl)aminodeoxyclavulanate (137 mg) in ethanol (30 cm³) was hydrogenolysed at atmospheric pressure in the presence of 10% palladium on charcoal (0.5 g which had been prehydrogenated for 20 minutes) for 25 minutes. The catalyst was filtered off and washed with aqueous ethanol, the filtrate was evaporated and ethanol added. The resulting crystals were filtered off cold and dried. This product was chromatographed on cellulose eluting with butanol-isopropanol-water; 4:4:1. Fractions were collected containing the title compound in low yield Rf(SiO₂/butanol-isopropanol water; 7:7:6)=0.46 (detection by aqueous potassium permanganate spray).

EXAMPLE 59

Benzyl 9-N-(2'-methylallyl)-N-(3"-transphenylallyl)aminodeoxyclavulanate

Benzyl dichloroacetylclavulanate (5.9 g; 14.8 mM) in dimethylformamide (40 cm$^3$) at 0° was treated with N-(2'-methylallyl)-N-(3'-transphenylallyl) amine (1.9 equivalents) and stirred at 0° for 1¾ hours. The mixture was then poured into ethyl acetate (250 cm$^3$) and washed with water (5×100 cm$^3$) and saturated brine (5×100 cm$^3$), dried (anhydrous magnesium sulphate) and evaporated to an oil. This oil was chromatographed on silica eluting with ethylacetate-cyclohexane (1:2), fractions were collected containing the title compound; Rf(SiO$_2$/ethylactate:cyclohexane 1:1)=0.76; and combined fractions were evaporated to yield an oil, 3.49 g (51%). Detection by aqueous potassium permanganate spray. $\nu$(film) 1805, 1750, 1700, 1495, 1450, 1305, 1230, 1175, 1120, 1080, 1045, 1015, 967, 895, 745, 695 cm$^{-1}$. $\delta$(CDCl$_3$) 1.71 (3H, s), 2.89 (2H, s), 2.93 (1H, d, J 17 Hz), 3.07 (2H, d, J 6 Hz), 3.16 (2H, d, J 7 Hz), 3.39 (1H, dd, J 17 and 3 Hz), 4.72 (1H, t, J 7 Hz), 4.75–4.95 (2H, broad m), 5.06 (1H, d, J 3 Hz), 5.16 (2H, s), 6.15 (1H, dt, J 16 and 6 Hz), 6.45 (1H, d, J 16 Hz), 7.15–7.50 (10H, m).

EXAMPLE 60

9-N-Isobutylaminodeoxyclavulanic acid

Benzyl 9-N-(2'-methylallyl)-N-(3"-trans phenylallyl)aminodeoxyclavulanate (11 g) in ethanol (40 cm$^3$) was hydrogenolysed for 20 minutes at atmospheric pressure in the presence of 10% palladium on charcoal (300 mg; which had been prehydrogenated for 10 minutes). The catalyst was filtered off and washed with aqueous ethanol. The filtrate was evaporated and ethanol added, the resulting crystals were filtered off cold and dried. This product was chromatographed on cellulose eluting with butanol-isopropanol water; 4:4:1. Fractions were collected containing the title compound in low yield; Rf(SiO$_2$/butanol-isopropanol-water; 7:7:6)=0.46 (detection by aqueous potassium permanganate spray).

EXAMPLE 61

Benzyl 9-N-(2'-methylallyl)-N-(2"-methyl-3"-phenylallyl)aminodeoxyclavulanate Benzyl 9-O-dichloroacetylclavulanate (6.30 g; 15.8 mmole) in acetonitrile (60 ml) at 4° C. was treated with dropwise addition of N-(2'-methylallyl)-N-(2"-methyl-3"-phenylallyl) amine (6 g; 30 mmol) in acetonitrile (60 ml). On final addition the reaction was stirred at 4° to 10° C. for 2 hours.

The acetonitrile was then removed under a reduced pressure and the resulting oil was dissolved in ethyl acetate. The solution was then washed with water, brine, dried (MgSO$_4$) and evaporated in vacuo. Silica-gel column chromatography afforded the title compound as as an oil in a 16% yield.

$\nu_{max}$ (CHCl$_3$): 1802, 1745, 1695 and 1600 (br) cm$^{-1}$.
$\delta$(CDCl$_3$): 1.70 (3H, s), 1.82 (3H, s), 2.84 (2H, s), 2.92 (2H, s), 2.90 (1H, d, J 17 Hz), 3.12 (2H, d, J 7 Hz), 3.38 (1H, dd, J 17 and 3 Hz), 4.70 (1H, br.t, J 7 Hz), 4.82 (2H, br.s), 5.06 (1H, s), 5.16 (2H, s), 5.60 (1H, d, J 3 Hz), 6.36 (1H, s), 7.22 and 7.30 (10H, 2×s).

EXAMPLE 62

9-N-Isobutylaminodeoxyclavulanic acid

Benzyl-9-N-(2'-methylallyl)-N-(2"-methyl-3"phenylallyl)aminodeoxyclavulanate (1.0 g; 2 mmol) in ethanol (20 ml) was carefully added to a prehydrogenated mixture of 10% palladium on charcoal (300 mg) in ethanol (30 ml). The mixture was then hydrogenated at atmospheric pressure for 30 minutes. The catalyst was then filtered off and washed well with aqueous ethanol. The filtrate plus washings were then evaporated to dryness under a reduced pressure. Cellulose column chromatography afforded the title compound as a white crystalline solid in 30% yield.

EXAMPLE 63

Benzyl 9-N-(iso-butyl)-N-(2'-methylallyl)aminodeoxyclavulanate

N-Isobutyl-N-(2-methylallyl)amine (7.25 g, 57 mmol) in dimethylformamide (30 ml) was added dropwise to a solution of benzyl dichloroacetylclavulanate (12.0 g, 30 mmol) in dimethylformamide (200 ml) at −10° C. After 2 hours at this temperature the reaction mixture was poured into water and extracted with ethylacetate. The organic phase was washed several times with brine, dried (MgSO$_4$) and evaporated to a yellow oil. Chromatography in silica gel (elution:petrol/ethylacetate:3/1 grading to 2/1) afforded the title ester as an oil, 2.98 g (25%) I.R. (CHCl$_3$) 1802, 1745, 1700, and 895 cm$^{-1}$ N.M.R. (CDCl$_3$) 0.84 (6H, d, J 7 Hz), 1.52–1.88 (1H, m), 1.68 (3H, s), 2.00 (2H, d, J 7 Hz), 2.79 (2H, s), 2.94 (1H, d, J 17 Hz), 3.06 (2H, d, J 8 Hz), 3.41 (1H, dd, J 17 and 3 Hz), 4.68 (1H, bt, J 8 Hz), 4.78 (2H, bs), 5.03 (1H, bs), 5.17 (2H, s), 5.61 (1H, d, J 3 Hz), and 7.32 (5H, s).

EXAMPLE 64

9-N-Isobutylaminodeoxyclavulanic acid

10% Pd-C (0.83 g) in ethanol (80 ml) was hydrogenated for 15 minutes at 1 atmospheric of hydrogen. Benzyl 9-N-(isobutyl)-N-(2'-methylallyl)aminodeoxyclavulanate (2.5 g, 6.28 mmol) in ethanol (30 ml) was added and the hydrogenation continued for 45 minutes. The catalyst was then filtered off through celite and the pad was washed with some ethanol. These combined washings were evaporated to a yellow oil which crystallised from ethanol (0.120 g).

The filter pad, above was not washed with 50% aqueous ethanol (150 ml). Evaporation afforded the title material as a white solid (0.70 g).

Combination of all the mother liquors and evaporation afforded a dark oil which was chromatographed on silica gel (elution:ethylacetate/isopropanol/water:5/2/1 grading to 5/4/3) to provide more of the title product (0.115 g).

Total yield of required product=0.935 g (59% yield). N.M.R., I.R, and t.l.c. characteristics were identical to an authentic sample.

EXAMPLE 65

Phenacyl 9-N-Bis(2'-methylallyl)aminodeoxyclavulanate

Phenacyl 9-O-dichloroacethylclavulanate (5.0 g; 11.7 mmol) in dry dimethylformamide (50 ml). The mixture was cooled to 0° C. and bis (2'-methylallyl) amine (2.8 g; 22.2 mmol) in dry dimethylformamide (30 ml) was added dropwise. After stirring at 0° C. for 1½ hours the mixture was poured into ethyl acetate and washed several times with water and then dried (MgSO₄). After filtration the ethyl acetate was removed in vacuo to give a yellow oil, which on column chromatography afforded the required compound as a yellow gum, yield 32%. $[\alpha]_D^{20} + 11.0°$ (c. 1%, CHCl₃). Found C, 67.60; H, 6.70; N 6.38%, $C_{24}H_{28}N_2O_5$ requires: C, 67.91; H, 6.65; N, 6.60% $\nu_{max}$ (CHCl₃) 1805, 1760, and 1605 cm⁻¹; δ(CDCl₃) 1.72 (6H, s), 2.76→3.22 (7H, m), 3.45 (1H, dd, J 17 and 3 Hz), 4.82 (5H, m), 5.19 (1H, s), 5.38 (2H, s), 5.66 (1H, d, J 3 Hz), 7.30→7.60 and 7.78→8.00.

EXAMPLE 66

Allyl 9-N,N-bis(2'-methylallyl)aminodeoxyclavulanate

Allyl dichloroacetylclavulanate (5 g; 14.3 mM) in dry dimethylformamide (50 cm³) at 0° was treated with bis (2 methylallyl)amine (1.9 equivalents) and stirred 2½ hours at between 0° and 5° C. The mixture was poured into ethylacetate (250 cm³) and washed with water (5×200 cm³) and saturated brine (5×150 cm³), dried (anhydrous magnesium sulphate) and evaporated to an oil. This oil was chromatographed on silica eluting with ethylacetate-cyclohexane; 1:1. Fractions were collected containing the title compound, Rf (SiO₂/ethylacetate-cyclohexane; 1:1)=0.90 (detection by aqueous potassium permanganate spray). Combined fractions were evaporated in vacuo to yield an oil, 1.33 g (27%), (film) 1808, 1750, 1695, 1450, 1370, 1308, 1232, 1180, 1120, 1015, 940, 895 cm⁻¹. (CDCl₃) 1.71 (6H, s), 2.83 (4H, s), 2.98 (1H, d, J 17 Hz), 3.07 (2H, d, J 7 Hz), 3.45 (1H, dd, J 17 and 3 Hz), 4.55-4.94 (7H, m), 5.02 (1H, s), 5.17-5.5 (2H, m), 5.63 (1H, d, J 3 Hz), 5.6-6.16 (1H, m).

EXAMPLE 67

(2-Methylallyl) 9'-N-(Isobutyl)-N-(2"-Methylallyl) aminodeoxyclavulanate (2-Methylallyl)-9'-O-dichloroacetylclavulanate (9.05 g; 24.8 mmol) in anhydrous dimethylformamide (90 ml) was cooled with stirring to −20° C. N-(Isobutyl)-N-(2-methylallyl) amine (6.0 g; 47 mmol) in anhydrous dimethylformamide (60 ml) was added dropwise over a period of 20 minutes. The reaction mixture was allows to warm to −10° C. and stirring continued for 2 hours.

The solution was poured into a cold mixture of ethyl acetate and water and shaken. The aqueous layer was extracted with more ethyl acetate. The combined organic layers were washed with water, dried (MgSO₄) and evaporated to an oil. Column chromatography afforded the title compound as a colourless oil in 23% yield.

$\nu_{max}$ (CHCl₃): 1805, 1750 and 1700 cm⁻¹. δ(CDCl₃): 0.85 (6H, d, J 7 Hz), 1.70 (3H, s), 1.77 (3H, s), 1.57 to 1.88 (1H, m), 2.05 (2H, d, J 7 Hz), 2.84 (2H, s), 2.94 (1H, d, J 17 Hz), 3.11 (2H, d, J 7 Hz), 3.46 (1H, dd, J 17 and 3 Hz), 4.58 (2H, s), 4.74 (1H, broad t, J 7 Hz), 4.81 (2H, broad s), 4.99 (2H, broad s), 5.06 (1H, s), and 5.66 (1H, d, J 3Hz).

EXAMPLE 68

9-N-Isobutylaminodeoxyclavulanate (2-Methylallyl)-9'-N-(isobutyl)-N-(2"-methylallyl) aminodeoxyclavulanate (1.5 g; 4 mmol) in ethanol (20 ml) was carefully added to a pre-hydrogenated mixture of 10% palladium on charcoal (0.5 g) in ethanol (20 ml). The mixture was hydrogenated at 1 atmosphere until the uptake of hydrogen ceased.

The mixture was filtered through a celite pad and the "cake" washed with aqueous ethanol. The filtrate plus washings were evaporated to dryness resulting in a yellow solid which an addition of a small amount of ethanol gave a white solid. Filtration afforded the title compound in 20% yield. Spectral data was consistent with an authentic example.

EXAMPLE 69

Composition (a) A solution for injection may be prepared by dissolving 100 mg of sterile 9-N-isobutylaminodeoxyclavulanic acid in 1 ml of sterile water.

(b) A solution for injection may be prepared by dissolving 50 mg of sterile 9-N-isobutylaminodeoxyclavulanic acid and 250 mg of sterile sodium amoxycillin in 1 ml of sterile water.

(c) A solution for injection may be prepared by dissolving 125 mg of sterile 9-N-isobutylaminodeoxyclavulanic acid and 125 mg of sterile cephaloridine in 1.5 ml of sterile water.

EXAMPLE 70

Compositions a. 100 mg of a sterile 9-N-benzylaminodeoxyclavulanic acid may be dissolved in 5 ml of sterile water for injection to yield an injectable solution.

b. 100 mg of sterile 9-N-benzylaminodeoxyclavulanic acid and sterile sodium amoxycillin equivalent to 250 mg pure free acid may be dissolved in 8 ml of sterile water for injection to yield an injectable solution.

c. 50 mg of sterile 9-N-benzylaminodeoxyclavulanic acid and sterile sodium amoxycillin equivalent to 250 mg pure free acid may be dissolved in 5 ml of sterile water for injection to yield an injectable solution.

Similar compositions may be prepared which contain 9-N-(4-acetamidobenzyl)aminodeoxyclavulanic acid, 9-N-(4-hydroxybenzylamino)deoxyclavulanic acid or 9-N-(4-methoxybenzyl)aminodeoxyclavulanic acid in place of the 9-N-benzylaminodeoxyclavulanic acid.

Demonstration 1

In-vitro Activity

The MIC values for ampicillin alone and in 1 μg/ml or 5 μg/ml of the compounds of the Examples were determined by the microtitre method. The results were as follows:

| | MIC (μg/ml) of Ampicillin in the presence of 0 μg/ml, 1 μg/ml of 5 μg/ml of synergist. | | | | | | | | | | | |
|---|---|---|---|---|---|---|---|---|---|---|---|---|
| | Staphylococcus aureus Russell | | | Klebsiella aerogenes E70 | | | Proteus sp. C889 | | | E. coli JT 39 | | |
| Compound of Example No. | +0 | +1 | +5 | +0 | +1 | +5 | +0 | +1 | +5 | +0 | +1 | +5 |
| 1 | 62.5 | 0.3 | 0.01 | >500 | 3.1 | 1.5 | >500 | 125 | 4 | >500 | 8 | 8 |
| 2 | 500 | 0.08 | 0.01 | 1000 | 1.6 | 0.4 | 2000 | 2 | 0.5 | 2000 | 2 | 0.5 |

-continued

| Compound of Example No. | Staphylococcus aureus Russell | | | Klebsiella aerogenes E70 | | | Proteus sp. C889 | | | E. coli JT 39 | | |
|---|---|---|---|---|---|---|---|---|---|---|---|---|
| | +0 | +1 | +5 | +0 | +1 | +5 | +0 | +1 | +5 | +0 | +1 | +5 |
| 3 | 62 | 0.2 | — | >500 | 6.2 | 6.2 | >500 | 62 | 16 | >500 | 8 | 4 |
| 4 | 500 | 0.6 | 0.04 | 1000 | 3.1 | 1.6 | 2000 | 31 | 2 | 2000 | 16 | 4 |
| Sodium Clavulanate | 500 | 0.6 | 0.02 | 100 | 3.1 | 0.8 | 2000 | 62 | 4 | 2000 | 31 | 4 |
| 5 | >62.5 | 0.3 | <0.01 | >500 | 6.25 | 3.12 | >500 | 125 | 8 | >500 | 4 | 4 |
| 7 | >62.5 | 0.01 | <0.01 | >500 | 12.5 | 3.12 | >500 | 62.5 | 2 | >500 | 8 | 4 |
| 13 | >62.5 | 0.08 | — | >500 | 3.1 | 1.5 | >500 | 4 | 2 | >500 | 8 | 2 |

MIC (µg/ml) of Ampicillin in the presence of 0 µg/ml, 1 µg/ml of 5 µg/ml of synergist.

In-vivo Activity

The synergistic effect of the compounds of this invention in animals is demonstrated by the co-administration of the compound of Example 2 and amoxycillin (as the sodium salt) to test animals infected by *E. coli* JT 39. This microorganism produces considerable quantities of a β-lactamase which degrades amoxycillin so reducing its antibaceterial effectiveness in-vivo. However when the compound of Example 2 is administered to the test animal at the same time as amoxycillin the inhibition of the β-lactamase allows the amoxycillin to exhibit its antibacterial activity. The following results were obtained when amoxycillin alone or together with the compound of Example 2 or sodium clavulanate was administered sub-cutaneously to mice infected by *E. coli* JT 39:

| Test Compounds | CD$_{50}$ (mg/kg × 2) |
|---|---|
| Sodium amoxycillin alone | 200 |
| Sodium amoxycillin + 2 mg/kg of compound of Example 2 | 3.3 |
| Sodium amoxycillin + 1 mg/kg of compound of Example 2 | 8.7 |
| Sodium amoxycillin + 2 mg/kg of sodium clavulanate | 14.5 |
| Sodium amoxycillin + 1 mg/kg of sodium clavulanate | 58 |

(Sodium amoxycillin was prepared by dissolving amoxycillin trihydrate in a sodium carbonate/sodium bicarbonate buffer).

The compound of Example 2 was also effective in protecting amoxycillin from the β-lactamase of *E. coli* JT 39 in-vivo when administered orally but was less effective per given weight than when administered sub-cutaneously.

The compound of Example 2 was not observed to produce toxic effects during these tests.

Demonstration 2

Demonstration of Effectiveness as Synergist

The following approximate CD$_{50}$ values were obtained for amoxycillin in the presence of the compounds of certain Examples when administered sub-cutaneously 1 and 5 hours post infection against a peritoneal infection due to *E. coli* JT 39.

| | CD$_{50}$ |
|---|---|
| Test 1 | |
| Amoxycillin alone | 1000 mg/kg × 2 |
| Amoxycillin + Comp Ex 2 at 2 mg/kg | 4.5 mg/kg × 2 |
| Amoxycillin + Comp Ex 2 at 1 mg/kg | 6.3 mg/kg × 2 |
| Amoxycillin + Comp Ex 7 at 2 mg/kg | 6.4 mg/kg × 2 |
| Amoxycillin + Comp Ex 7 at 1 mg/kg | 7.5 mg/kg × 2 |
| Amoxycillin + Comp Ex 9 at 2 mg/kg | 4.5–8 mg/kg × 2 |
| Amoxycillin + Comp Ex 9 at 1 mg/kg | 12 mg/kg × 2 |
| Cefazolin alone | 10.5 mg/kg × 2 |
| Test 2 | |
| Amoxycillin alone | 1000 mg/kg × 2 |
| Amoxycillin + Comp Ex 6 at 2 mg/kg | 3.1 mg/kg × 2 |
| Amoxycillin + Comp Ex 6 at 1 mg/kg | 8 mg/kg × 2 |
| Amoxycillin + Comp Ex 2 at 2 mg/kg | 4.5 mg/kg × 2 |
| Amoxycillin + Comp Ex 2 at 1 mg/kg | 8.5 mg/kg × 2 |
| Test 3 | |
| Amoxycillin alone | 1000 mg/kg × 2 |
| Amoxycillin + Comp Ex 13 at 2 mg/kg | 4.4 mg/kg × 2 |
| Amoxycillin + Comp Ex 2 at 2 mg/kg | 5.8 mg/kg × 2 |

Demonstration 3

Demonstration of Effectiveness as Anti-Bacterial

Mice were infected with staphylococcus aureus Russell (thigh lesion with 0.2 ml im) and thereafter were dosed subcutaneously at 1, 3 and 5 hours post infection with a solution of the test compound. The following results were obtained:

| Compound | Dosage (mg/kg) | Protection (%) |
|---|---|---|
| 9-N—Benzylaminodeoxy-clavulanic acid | 5 | 69.8 |
| | 10 | 89.7 |
| | 20 | 99.3 |
| 9-N—p-Methoxybenzyl-aminodeoxyclavulanic acid | 5 | 28.0 |
| | 10 | 80.8 |
| | 20 | 87.6 |
| Cloxacillin | 20 | 61.6 |
| | 50 | 91.7 |
| Cefazolin | 20 | 39.0 |
| | 50 | 71.2 |

The LD$_{50}$ of 9-N-benzylaminodeoxyclavulanic acid in mice is greater than 1000 mg/kg on intra peritoneal injection and greater than 500 mg/kg on sub-cutaneous administration.

Demonstration 4

9-N-Isobutylaminodeoxyclavulanic acid and 9-N-n-butylaminodeoxyclavulanic acid have been compared as synergists in vivo by the subcutaneous route against 2 strains of R$_{TEM}$ *E. Coli* in intraperitoneal mouse infections. On each occasion the isobutylamine was more active then the n-butylamine, producing a lower CD$_{50}$ for amoxycillin. These results are tabulated below.

Comparative subcutaneous synergistic activity of 9-N-Isobutylaminodeoxyclavulanic acid and 9-N-n-butylaminodeoxyclavulanic acid with amoxycillin against mouse E. Coli infections

|  | \multicolumn{4}{c}{CD$_{50}$ mg/kg × 2} |
| --- | --- | --- | --- | --- |
|  | \multicolumn{2}{c}{E. Coli E96} | \multicolumn{2}{c}{E. Coli E124} |
|  | P392 | P409 | P397 | P412 |
| Amoxycillin alone | >1000 | >1000 | >1000 | >1000 |
| Amoxycillin + 2 mg/kg 9-N—n-butylaminodeoxy-clavulanic acid | 17.5 | 7.2 | 17.5 | 11.5 |
| 9-N—isobutylaminodeoxy-clavulanic acid | 13.5 | 4.4 | 10.5 | 8 |

It has been also found that other 9-aralkylaminodeoxyclavulanic acid derivatives may be prepared that have antibacterial and β-lactamase inhibitory properties.

Accordingly the present invention also provides the compounds of the formula (XVII):

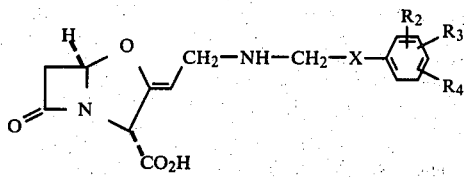
(XVII)

or an ester thereof wherein $R_2$, $R_3$ and $R_4$ are as defined in relation to formula (II) and X is an alkylene group of 1 to 4 carbon atoms.

The compounds of the formula (XVII) per se exist in the form of zwitterions, that is they may be represented as shown in formula (XVIIa):

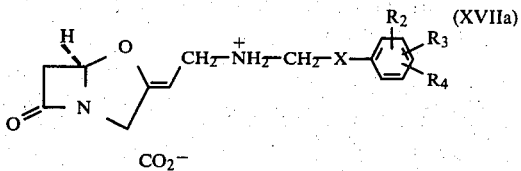
(XVIIa)

if desired wherein $R_1$ is as defined in relation to formula (II). These zwitterionic compounds form a favoured aspect of this invention in view of their generally crystalline form.

Suitably X is a straight chained alkylene group of 1 to 4 carbon atoms. Suitably X is an alkylene group of 1 to 3 carbon atoms branched to carry a methyl group.

More suitably X is a CH$_2$ or CH$_2$.CH$_2$ group.

As has been previously indicated we prefer to prepare and use the crystalline zwitterionic compounds within the formula (II). However, esters of the compounds of the formula (II) also form part of this invention, for example as the free base or as the acid addition salt, since such compounds may also be used to enhance the effectiveness of penicillins or cephalosporins.

Certain suitable esters of the compounds of the formula (II) include those of the formula (XVIII) and (XIX):

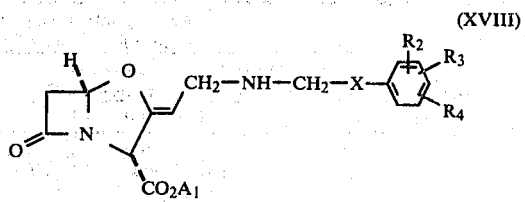
(XVIII)

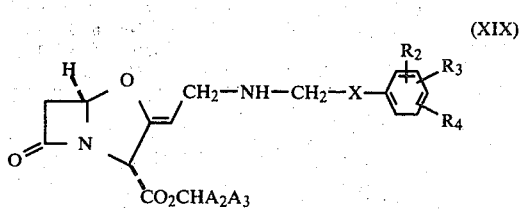
(XIX)

wherein X, $R_2$, $R_3$ and $R_4$ are as defined in relation to formula (XVII) and $A_1$, $A_2$ and $A_3$ are as defined in relation to formulae (VIII) and (IX).

The compounds of the formula (XVIII) and (XIX) may be used, formulated and prepared as hereinbefore described in relation to the compounds of the formula (II), (VIII) and (IX).

EXAMPLE 71

Benzyl 9-N-(2-methylallyl)-N-(3-trans phenylallyl) aminodeoxyclavulanate

Benzyl dichloroacetyl clavulanate (5.9 g; 14.8 mm) in dimethylformamide (40 cm$^3$) at 0° was treated with N-(2-methylallyl)-N-(3-trans phenylallyl) amine (1.9 equivalents) and stirred at 0° for 1¾ hours. The mixture was then poured into ethyl acetate (250 cm$^3$) and washed with water (5×100 cm$^3$) and saturated brine (5×100 cm$^3$), dried (anhydrous magnesium sulphate) and evaporated to an oil. This oil was chromatographed on silica gel eluting with ethylacetate-cyclohexane (1:2), fractions were collected containing the title compound; Rf (SiO$_2$/ethylacetate:cyclohexane; 1:1)=0.76, detection by aqueous potassium permanganate spray. Combined fractions were evaporated to yield an oil, 3.49 g (51%). ν (film) 1805, 1750, 1700, 1495, 1450, 1305, 1230, 1175, 1120, 1080. 1045, 1015, 967, 895, 745, 695 cm$^{-1}$. δ (CDCl$_3$) 1.71 (3H, s, CH$_2$C(CH$_3$)=CH$_2$), 2.89 (2H, s, NCH$_2$C(CH$_3$)=CH$_2$, 2.93 (1H, d, J 7 Hz, 6βC$\underline{H}$), 3.07 (2H, d, J 6 Hz, NCH$_2$CH=CH), 3.16 (2H, d, J 7 Hz, 9CH$_2$), 3.39 (1H, dd, J 17 and 3 Hz, 6αC$\underline{H}$), 4.72 (1H, t, J 7 Hz, 8 CH), 4.75–4.95 (2H, broad m, CH$_2$C(CH$_3$)=CH$_2$), 5.06 (1H, s, 3C$\underline{H}$), 5.16 (2H, s, CO$_2$CH$_2$C$_6$H$_5$), 5.58 (1H, d, J 3 Hz, 5αCH), 6.15 (1H, dt, J 16 and 6 Hz, NCH$_2$C$\underline{H}$=CH—), 6.45 (1H, d, J 16 Hz, NCH$_2$—CH=C$\underline{H}$—), 7.15–7.50 (10H, m, 2×C$_6$H$_5$).

EXAMPLE 72

9-N-(3-Phenylpropyl)aminodeoxyclavulanic acid

Benzyl 9-N-(2-methylallyl)-N-(3-trans phenylallyl) aminodeoxyclavulanate (1:1 g; 2.4 mm) in ethanol (40cm$^3$) was hydrogenolysed for 20 minutes at atmospheric pressure in the presence of palladium on carbon (10% Pd; 0.3 g; prehydrogenated for 20 minutes). The catalyst was filtered off and washed with ethanol (20 cm$^3$), then washed separately with aqueous ethanol (100 cm$^3$), this aqueous washing was evaporated to a crystalline solid. This solid was chromatographed on cellulose eluting with butanol-propan-2-ol-water; 4:4:1. Fractions were collected containing the title compound, Rf (SiO$_2$/butanol-propan-2-ol-water; 7:7:6)=0.64 (detection by aqueous potassium permanganate spray) Combined fractions were evaporated to yield a crystalline solid, this solid was washed with cold ethanol and dried to yield 100 mg (13%) of the title compound. ν(NUJOL(3350(broad), 1803, 1695, 1615, 1565, 1305, 1290, 1185, 1125, 1090, 1050, 1020, 1005, 925, 895, 760, 750, 725, 695 cm$^{-1}$. δ(D$_2$O/DMSO(20%)) 1.72–2.10 (2H, m, NH$_2$+CH$_2$CH$_2$CH$_2$-), 2.57–3.02 (4H, m, NH$_2$+CH$_2$CH$_2$CH$_2$C$_6$H$_5$), 3.00 (1H, d, J 17 Hz, 6βC$\underline{H}$), 3.52 (1H, dd, J 17 and 3 Hz, 6αC$\underline{H}$), 3.62 (2H, s, J 7 Hz, 9CH$_2$), 8CH obscured by HOD, 4.90 (1H, s, 3C$\underline{H}$), 5.67 (1H, d, J 3 Hz, 5αC$\underline{H}$), 7.23 (5H, s, C$_6$H$_5$).

EXAMPLE 73

Composition (a) The compound of Example 72(50 mgs) in sterile form may be dissolved in water for injection B.P. (2.5 mls) to form an injectable solution.

(b) The compound of Example 72(50 mgs) in sterile form and sodium amoxycillin (150 mgs) in sterile form may be dissolved in water for injection B.P. (2.5 mls) to form an injectable solution.

EXAMPLE 74

Benzyl 9-N(2-methyl-3-phenylallyl-N-(4-phenylbutyl)aminodeoxyclavulanate

Benzyl 9-O dichloroacetyl clavulanate (6.0 g; 15.1 mmol) in dry dimethylformamide (60 ml) was cooled, with stirring, to −20° C. N-(2-methyl-3-phenylallyl)-N-(4-phenylbutyl)amine (8.0 g; 28.7 mmol) in dry dimethylformamide (80 ml) was then added dropwise over a period of 20 minutes. The reaction mixture was then allowed to warm to −10° C. and stirring continued for 1 hour. The solution was then poured into an ethyl acetate/water mixture and shaken. The two layers were separated and the aqueous layer extracted with more ethyl acetate. The combined organic layers were washed with a saturated solution of sodium chloride, dried (MgSO$_4$) and evaporated to an oil. Column chromatography afforded the title compound as a colourless oil Rf (SiO$_2$/ethyl acetate: petroleum ether; 1:1)=0.6 ν$_{max}$ (CHCl$_3$): 1800, 1745 and 1695 cm$^{-1}$. δ (CDCl$_3$): 1.30 to 1.70 (4H, m, C$\underline{H}_2$C$\underline{H}_2$CH$_2$Ph); 1.82 (3H, s, C$\underline{H}_3$); 2.35 (2H, broad t, J 7 Hz, N-CH$_2$CH$_2$CH$_2$C$\underline{H}_2$Ph); 2.57 (2H, broad t, J 7 Hz, N-CH$_2$CH$_2$CH$_2$C$\underline{H}_2$Ph); 2.89 (1H, d, J 17 Hz, 6β-CH); 2.93 (2H, s, N-C$\underline{H}_2$-C=); 3.16 (2H, d, J 7 Hz, 9-C$\underline{H}_2$); 3.36 (1H, dd, J 17 and 3 Hz, 6α-C$\underline{H}$); 4.70 (1H, broad t, J 7 Hz, 8-C$\underline{H}$); 5.05 (1H, s, 3-C$\underline{H}$); 5.13 (2H, s, CO$_2$C$\underline{H}_2$); 5.55 (1H, d, J 3 Hz, 5-C$\underline{H}$); 6.34 (1H, s, C$\underline{H}$C$_6$H$_5$); 7.00 to 7.48 (15H, m, aromatic $\underline{H}$'s).

EXAMPLE 75

9-N-(4-Phenylbutyl)aminodeoxyclavulanic acid

Benzyl 9-N-(2-methyl-3-phenylallyl)-N-(4-phenylbutyl)aminodeoxyclavulanate (1.5 g; 2.7 mmol) in 5% tetrahydrofuran/ethanol (20 ml) was carefully added to a prehydrogenated mixture of 10% palladium on charcoal (750 mg) in ethanol (50 ml). The mixture was then hydrogenated at 1 atmosphere until the uptake of hydrogen ceased (1.5 hours). The catalyst was then filtered off through a celite pad and the 'cake' washed well with 75% aqueous ethanol. The ethanol plus washings were then evaporated to dryness to give a yellow solid which on trituration with ethanol gave the title compound as a white crystalline solid (56%).

ν$_{max}$ (KBr): 1800, 1685 and 1620 (broad) cm$^{-1}$. δ (D$_2$O/D$_6$ acetone): 1.65–2.15 (4H, m, N-CH$_2$C$\underline{H}_2$C$\underline{H}_2$CH$_2$Ph), 2.82 and 3.20 (4H, 2×m, N-C$\underline{H}_2$CH$_2$CH$_2$C$\underline{H}_2$Ph), 3.18 (1H, d, 6β-C$\underline{H}$, partially obscured by 9-CH$_2$), 3.85 (2H, d, J 7 Hz, 9-C$\underline{H}_2$), 4.85 (1H, br.t, 8-C$\underline{H}$, partially obscured by HOD), 5.05 (1H, m, 3-C$\underline{H}$), 5.95 (1H, d, J 3 Hz, 5-C$\underline{H}$) and 7.40 (5H, s, C$_6$H$_5$).

EXAMPLE 76

Benzyl 9-N-[2'-(3,4-dimethoxyphenyl)ethyl]-N-(2-methyl-3-phenylallyl)aminodeoxyclavulanate Benzyl dichloroacetylclavulanate (4.74 g; 11.8 mmol) in dry dimethylformamide (50cm$^3$) at −10° was treated with 1.9 equivalents of N-[β-(3,4-dimethoxyphenyl)ethyl]-N-(2-methyl-3-phenyl allyl) amine, slowly in dimethylformamide (20cm$^3$), and stirred for 1 hour between −10° and +6°. The mixture was poured into ethylacetate (300cm$^3$) and was washed with water (4×200cm$^3$) and saturated brine (5×200cm$^3$), dried (anhydrous magnesium sulphate) and evaporated in the presence of toluene to low volume, this crude product was chromatographed on silica eluting with ethyl acetate-cyclohexane (1:2). Fraction were collected containing the title compound, Rf (SiO$_2$/ethylacetate-cyclohexane; 1:1)=0.63 (detection by aqueous potassium permanganate spray). Combined fractions were evaporated to afford the title compound as an oil; 2.0 g (29%) ν (film) 1805, 1750, 1695, 1515, 1450, 1305, 1265, 1238, 1160, 1030, 745, 700 cm$^{-1}$. δ (CDCl$_3$) 1.83 (3H, s, C(CH$_3$)=CH), 2.65 (4H, bs, NCH$_2$CH$_2$), 2.93 (1H, d, J 17 Hz, 6βC$\underline{H}$ partially obscured), 3.05 (2H, s, NCH$_2$C(CH$_3$)l), 3.28 (2H, d, J 7 Hz, 9C$\underline{H}_2$partially obscured), 3.40 (1H, dd, J 17 and 3 Hz, 6αC$\underline{H}$, partially obscured), 3.78 and 4.22 (6H, 2×s, 2×OC$\underline{H}_3$), 4.75 (1H, bt, J 7 Hz, 8 C$\underline{H}$), 5.08 (1H, bs, 3 C$\underline{H}$), 5.16 (2H, s, CO$_2$CH$_2$C$_6$H$_5$), 5.62 (1H, d, J 3 Hz, 5αC$\underline{H}$), 6.38 (1H, bs, C(CH$_3$)=C$\underline{H}$), 6.60–6.85 (3H, m, CH$_2$C$_6$H$_3$(OCH$_3$)$_2$), 7.10–7.50 (10H, m, 2×C$_6$H$_5$).

EXAMPLE 77

9-N-[2-(3,4-Dimethoxyphenyl)ethyl]-aminodeoxyclavulanic acid

Benzyl 9-N-[2-(3,4-dimethoxyphenyl)ethyl]-N-(2-methyl-3-phenyallyl)aminodeoxyclavulanate (1.88 g; 3.23 mmol) in ethanol 35 cm$^3$) tetrhydrofuran (12 cm$^3$) and water (5 cm$^3$) was hydrogenolysed at atmospheric pressure in the presence of 10% palladium on carbon (0.62 g; which had been prehydrogenated for 10 minutes) for 35 minutes. The catalyst was filtered off and washed with ethanol (20 cm$^3$) then with aqueous ethanol (200 cm$^3$), this aqueous washing was collected separately and was evaporated to afford a white crystalline solid, this solid was was hed with cold ethanol and dried to give the title compound (41%). Rf (SiO$_2$/ethylacetate-ethanol-water; 5:2:2)=0.54 (detection by aqueous potassium permanganate spray).

ν (Nujol) 1798, 1700, 1635, 1610, 1570, 1510 cm$^{-1}$, ν (KBr) 1792, 1697, 1620, 1515 cm$^{-1}$.

EXAMPLE 78

Benzyl 9-N-(2-phenylethyl)-N-(2-methyl-3-phenylallyl-)aminodeoxyclavulanate

Benzyl dichloracetylclavulanate (8 g; 20 mM) in dry dimethylformamide (50cm$^3$) at $-10°$ was treated with 1.9 equivaelents of N-(2-phenylethyl)-N-(2-methyl-3-phenylallyl) amine in 20 cm$^3$ dimethylformamide and stirred for $\frac{3}{4}$ hour between $-10°$ and $0°$ C. The mixture was poured into ethyl acetate (250 cm$^3$) and washed with water (5×100 cm$^3$) and saturated brine (6×150 cm$^3$), dried (anhydrous magnesium sulphate) and evaporated in the presence of toluene to small volume. This crude product was chromatographed on silica eluting with ethyl acetate-cyclohexane; 1:2. Fractions were collected containing the title compound Rf (SiO$_2$/ethylacetate-cyclohexane; 1:2)=0.70 (detection by aqueous potassium permanganate spray). Combined fractions were evaporated to afford the title compound (33%). $\nu$ (film) 1805, 1750, 1695, 1495, 1453, 1305, 1178, 1015, 750, 702 cm$^{-1}$. $\delta$ (CDCl$_3$) 1.79 (3H, s, C(CH$_3$)=CH), 2.55–2.90 (4H, m, NCH$_2$CH$_2$C$_6$H$_5$), 2.92 (1H, d, J 17 Hz, 6$\beta$CH, partially obscured by NCH$_2$ C (CH$_3$)), 3.27 (2H, d, J 7 Hz, 9CH$_2$, partially obscured by 6$\alpha$-CH), 3.40 (1H, dd, J 17 and 3 Hz, 6$\alpha$CH, partially obscured by 9CH$_2$), 4.73 (1H, bt, J 7 Hz, 8CH), 5.08 (1H, s, 3CH), 5.15 (2H, s, OCH$_2$ C$_6$H$_5$), 5.62 (1H, d, J 3 Hz; 5$\alpha$CH), 6.37 (1H, bs, C(CH$_3$)=CH), 7.0–7.5 (15H, m, 2×CH$_2$C$_6$H$_5$, =CH-C$_6$H$_5$).

EXAMPLE 79

9-N-(2-Phenylethyl)aminodeoxyclavulanic acid

Benzyl 9-N-(2-phenylethyl)-N-(2-methyl-3-phenylallyl) aminodeoxyclavulanate (1.72 g; 3.3 mM) in ethanol (35cm$^3$), tetrahydrofuran (12cm$^3$) and water (5cm$^3$) was hydrogenolysed at atmospheric pressure in the presence of 10% palladium on charcoal (560 mg) for 30 minutes. The catalyst was filtered off and washed with ethanol (30cm$^3$) then with aqueous ethanol (150cm$^3$), this aqueous washing was collected separately and was evaporated to afford the title compound as a white solid. This solid was washed with cold ethanol and dried, yield =0.50 g. The initial catalyst filtrate and ethanolic washings were evaporated to give an oil, ethanol was added and on cooling crystals formed, these were filtered off, washed with cold ethanol and dried to yield 60 mg of the title compound. Rf (SiO$_2$/ethylacetate-ethanol-water (5:2:2)=0.50. Total yield =0.56 g (56%) $\nu$ (Nujol) 1805, 1695, 1615cm$^{-1}$. $\delta$(D$_2$O/(CD$_3$)$_2$CO) 2.80–3.60 (5H, broad m, NH$_2$CH$_2$CH$_2$C$_6$H$_5$ and 6$\beta$-CH), 3.66 (1H, dd, J 17 and 3 Hz, 6$\alpha$-CH, partially obscured by 9-CH$_2$), 3.84 (2H, d, J 8 Hz, 9-CH$_2$), 4.72–5.05 (2H, m, 3-CH and 8-CH), 5.83 (1H, d, J 3 Hz, 5-CH), 7.38 (5H, s, CH$_2$C$_6$H$_5$).

EXAMPLE 80

Benzyl 9-N-(2-methylallyl)-N-(α-methylcinnamyl)aminodeoxyclavulanate

Benzyl 9-O-dichloroacetyl clavulanate (6.30 g; 15.8 mmol) in acetonitrile (60 mls) at 4° C. was treated with dropwise addition of N-(2-methylallyl)-N-(α-methylcinnamyl)amine (6 g; 30 mmol) in acetonitrile (60 mls). On final addition the reaction was stirred at 4 to 10° C. for 2 hours. The acetonitrile was then removed under a reduced pressure and the resulting oil was dissolved in ethyl acetate. The solution was then washed with water, brine, dried (MgSO$_4$) and evaporated in vacuo. Silica-gel column chromatography afforded the title compound as an oil. $\nu_{max}$ (CHCl$_3$): 1802, 1745, 1695 and 1600 (br) cm$^{-1}$. $\delta$ (CDCl$_3$): 1.70 (3H, s, C(CH$_3$)=CH$_2$), 1.82 (3H, s, C(CH$_3$)=CH), 2.84 (2H, s, N-CH$_2$), 2.92 (2H, s, N-CH$_2$), 2.90 (1H, d, J 17 Hz, 6$\beta$-CH), 3.12 (2H, d, J 7 Hz, 9-CH$_2$), 3.38 (1H, dd, J 17 and 3 Hz, 6$\alpha$-CH), 4.70 (1H, br.t, J 7 Hz, 8-CH), 4.82 (2H, br.s, C=CH$_2$), 5.06 (1H, s, C-3H), 5.16 (2H, s, CO$_2$CH$_2$), 5.60 (1H, d, J 3 Hz, 5-CH), 6.36 (1H, s, C=CHC$_6$H$_5$), 7.22 and 7.30 (10H, 2×s, 2×C$_6$H$_5$).

EXAMPLE 81

9-N-(3-Phenyl-2-methylpropyl)aminodeoxyclavulanic acid

Benzyl-9-N-(2-methylallyl)-N-(α-methylcinnamyl) aminodeoxyclavulanate (1.0 g; 2 mmol) in ethanol (20 mls) was carefully added to a pre-hydrogenated mixture of 10% palladium on charcoal (300 mg's) in ethanol (30 mls). The mixture was then hydrogenated at atmospheric pressure for 30 minutes. The catalyst was then filtered off and washed well with aqueous ethanol. The filtrate plus washings were then evaporated to dryness under a reduced pressure. Cellulose column chromatography afforded the title compound as a white crystalline solid. $\nu_{max}$ (KBr): 1790, 1692 and 1610 (br) cm$^{-1}$. $\delta$(D$_2$O): 0.93 (3H, d, J 7 Hz, CH(CH$_3$)CH$_2$C$_6$H$_5$), 2.30 (1H, m, CH$_2$CH), 2.58 (2H, d, J 7 Hz, CH$_2$C$_6$H$_5$), 2.85 (2H, m, NH$_2^+$-CH$_2$), 2.97 (1H, d, J 17 Hz, 6$\beta$-CH), 3.54 (1H, dd, J 17 and 3 Hz, 6$\alpha$-CH), 3.62 (2H, d, J 7 Hz, 9-CH$_2$), 4.92 (1H, s, 3-CH), 5.67 (1H, d, J 3 Hz, 5-CH) and 7.25 (5H, m, CH$_2$C$_6$H$_5$). (8-CH obscured by HOD peak).

What we claim is:

1. A compound of the formula (XVII):

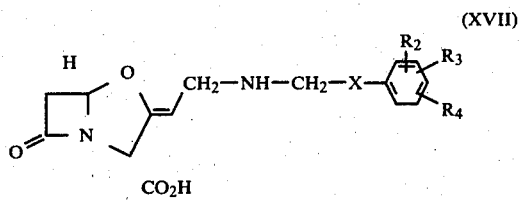

(XVII)

or an ester thereof of the formula (XVIII) or (XIX):

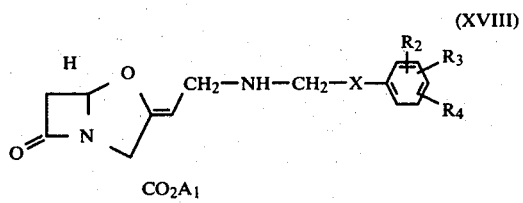

(XVIII)

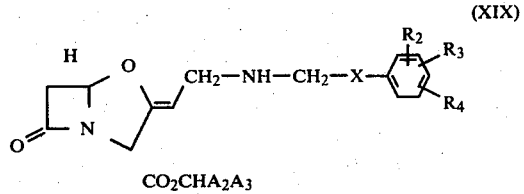

(XIX)

wherein A$_1$ is alkyl of 1 to 6 carbon atoms unsubstituted or mono-substituted by alkoxyl or alkanoyloxy of 1 to 7 carbon atoms, phthalidyl, ethoxycarbonyloxymethyl or α-ethoxycarbonyloxyethyl, $A_2$ is alkenyl or alkynyl of up to 5 carbon atoms or phenyl unsubstituted or mono-substituted by fluoro, chloro, bromo, nitro or alkyl or alkoxyl of up to 4 carbon atoms, $A_3$ is hydrogen, alkyl of up to 4 carbon atoms or phenyl unsubstituted or mono-substituted by fluoro, chloro, bromo, nitro, or alkyl or alkoxyl of up to 4 carbon atoms, $R_2$ is hydrogen, fluorine, chlorine, bromine, alkyl of 1 to 3 carbon atoms, alkoxy of 1 to 3 carbon atoms, alkanoyloxy of 1 to 3 carbon atoms, hydroxyl, alkoxycarbonyl of 1 to 3 carbon atoms in the alkoxy part, or a group $-N(R_5)CO.R_6$, $-N(R_5)SO_2R_6$ or $-CO-NR_5R_6$ wherein $R_5$ is hydrogen, alkyl of 1 to 3 carbon atoms, phenyl or benzyl and $R_6$ is alkyl of 1 to 3 carbon atoms, phenyl or benzyl; $R_3$ is hydrogen, fluorine, chlorine, alkyl group of 1 to 3 carbon atoms, alkoxy of 1 to 3 carbon atoms or alkanoyloxy of 1 to 3 carbon atoms; $R_4$ is hydrogen, fluorine, chlorine, alkyl group of 1 to 3 carbon atoms or alkoxyl of 1 to 3 carbon atoms; and X is alkylene of 1 to 4 carbon atoms.

2. A compound according to claim 1 in zwitterionic form.

3. A compound according to claim 2 wherein $R_2$ is hydrogen, fluorine, chlorine, methoxyl, ethoxyl, hydroxyl, acetoxyl, propionyloxy, methyl, ethyl, methoxycarbonyl, ethoxy-carbonyl or acetamido; $R_3$ is hydrogen, fluorine, chlorine, methoxyl, ethoxyl, acetoxyl, propionoxyl, methyl or ethyl; and $R_4$ is hydrogen, fluorine, chlorine, methoxyl, ethoxyl, acetoxyl, propionoxyl, methyl or ethyl.

4. A compound according to claim 3 wherein $R_4$ is hydrogen.

5. A compound according to claim 3 or 4 wherein $R_3$ is hydrogen or methoxyl.

6. A compound according to claim 4 wherein $R_2$ is hydrogen, fluorine, chlorine, methyl, methoxyl or acetamido and $R_3$ is hydrogen or methoxyl.

7. A compound according to claim 3 wherein X is $CH_2$ or $CH_2CH_2$.

8. A compound selected from
(i) 9-N-(3-Phenylpropyl)aminodeoxyclavulanic acid
(ii) 9-N-(4-Phenylbutyl)aminodeoxyclavulanic acid
(iii) 9-N-[2-(3,4-Dimethoxyphenyl)ethyl]aminodeoxyclavulanic acid
(iv) 9-N-(2-Phenylethyl)aminodeoxyclavulanic acid
(v) 9-N-(3-Phenyl-2-methylpropyl)aminodeoxyclavulanic acid.

9. A method of treating bacterial infections in mammals including humans which comprises administering to such a mammal in need thereof an antibacterially effective amount of a compound of the formula (XVIII):

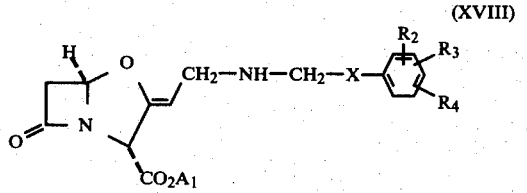

wherein $A_1$ is tetrahydropyranyl, tetrahydrofuranyl or a moiety of the formula $$-CHA_5-OA_6 \quad (c)$$

$$-CHA_5-COA_6 \quad (d)$$

$$-CHA_5-CO_2A_6 \quad (e)$$

wherein
$A_5$ is hydrogen or methyl;
$A_6$ is alkyl of up to 4 carbon atoms, phenyl, benzyl or phenyl or benzyl substituted by one or two alkyl or alkoxy moieties up to 3 carbon atoms or by fluoro, chloro, bromo or nitro, or $A_5$ is joined to $A_6$ to form an ortho-phenylene moiety unsubstituted or substituted by one or two alkyl or alkoxyl moieties of up to 3 carbon atoms or by fluoro, chloro, bromo or nitro,
$R_2$ is hydrogen, fluorine, chlorine, bromine, alkyl of 1 to 3 carbon atoms, alkoxy of 1 to 3 carbon atoms, alkanoyloxy of 1 to 3 carbon atoms, hydroxyl, alkoxycarbonyl of 1 to 3 carbon atoms in the alkoxy part, or a group $-N(R_5)CO.R_6$, $-N(R_5).SO_2R_6$ or $-CO-NR_5R_6$ wherein
$R_5$ is hydrogen, alkyl of 1 to 3 carbon atoms, phenyl or benzyl and
$R_6$ is alkyl of 1 to 3 carbon atoms, phenyl or benzyl;
$R_3$ is hydrogen, fluorine, chlorine, alkyl group of 1 to 3 carbon atoms, alkoxy of 1 to 3 carbon atoms or alkanoyl of 1 to 3 carbon atoms;
$R_4$ is hydrogen, fluorine, chlorine, alkyl group of 1 to 3 carbon atoms or alkoxyl of 1 to 3 carbon atoms; and
X is alkylene of 1 to 4 carbon atoms, in combination with a pharmaceutically acceptable carrier.

10. A method according to claim 9 wherein $A_6$ is methyl, ethyl, propyl, butyl, phenyl or benzyl.

11. A method according to claim 9 wherein $A_1$ is tetrahydropyranyl or tetrahydrofuranyl.

12. A method according to claim 9 wherein $A_1$ is $-CH_2-OA_6$ wherein $A_6$ is alkyl of up to 4 carbon atoms, phenyl, benzyl or phenyl or benzyl substituted by 1 or 2 alkyl or alkoxyl moieties of up to 3 carbon atoms, or by fluoro, chloro, bromo or nitro.

13. A pharmaceutical composition useful for treating bacterial infections in mammals including humans which comprises an antibacterially effective amount of a compound of the formula (XVII):

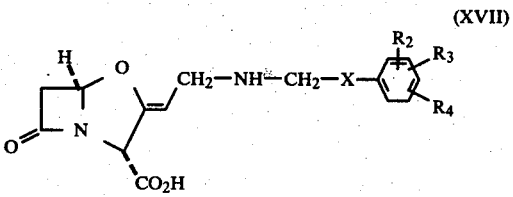

or an ester thereof of the formula (XVIII) or (XIX):

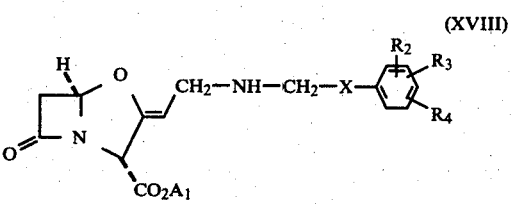

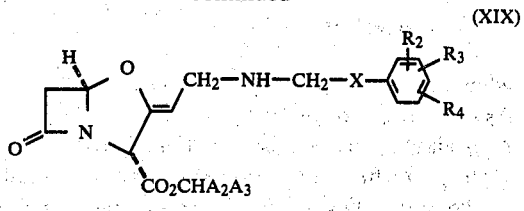

(XIX)

wherein $A_1$ is alkyl of 1 to 6 carbon atoms unsubstituted or mono-substituted by alkoxyl or alkanoyloxy of 1 to 7 carbon atoms, phthalidyl, ethoxycarbonyloxymethyl or α-ethoxycarbonyloxyethyl, $A_2$ is alkenyl or alkynyl of up to 5 carbon atoms or phenyl unsubstituted or mono-substituted by fluoro, chloro, bromo, nitro or alkyl or alkoxyl of up to 4 carbon aoms, $A_3$ is hydrogen, alkyl of up to 4 carbon atoms or phenyl unsubstituted or mono-substituted by fluoro, chloro, bromo, nitro, or alkyl or alkoxyl of up to 4 carbon atoms, $R_2$ is hydrogen, fluorine, chlorine, bromine, alkyl of 1 to 3 carbon atoms, alkoxy of 1 to 3 carbon atoms, alkanoyloxy of 1 to 3 carbon atoms, hydroxyl, alkoxycarbonyl of 1 to 3 carbon atoms in the alkoxy part, or a group —N($R_5$)CO.$R_6$ —N($R_5$)SO$_2$R$_6$ or —CO—NR$_5$R$_6$ wherein $R_5$ is hydrogen, alkyl of 1 to 3 carbon atoms, phenyl or benzyl and $R_6$ is alkyl of 1 to 3 carbon atoms, phenyl or benzyl; $R_3$ is hydrogen, fluorine, chlorine, alkyl group of 1 to 3 carbon atoms, alkoxy of 1 to 3 carbon atoms or alkanoyloxy of 1 to 3 carbon atoms; $R_4$ is hydrogen, fluorine, chlorine, alkyl group of 1 to 3 carbon atoms or alkoxyl of 1 to 3 carbon atoms; and X is alkylene of 1 to 4 carbon atoms as the sole antibacterial agent, in combination with a pharmaceutically acceptable carrier.

14. A composition according to claim 13 wherein the compound is in zwitterionic form.

15. A composition according to claim 13 wherein $R_2$ is hydrogen, fluorine, chlorine, methoxyl, ethoxyl, hydroxyl, acetoxyl, propionyloxy, methyl, ethyl, methoxycarbonyl, ethoxycarbonyl or acetamido; $R_3$ is hydrogen, fluorine, chlorine, methoxyl, ethoxyl, acetoxyl, propionoxyl, methyl or ethyl; and $R_4$ is hydrogen, fluorine, chlorine, methoxyl, ethoxyl, acetoxyl, propionoxyl, methyl or ethyl.

16. A composition according to claim 13 wherein $R_4$ is hydrogen.

17. A composition according to claim 13 or 14 wherein $R_3$ is hydrogen or methoxyl.

18. A composition according to claim 16 wherein $R_2$ is hydrogen, fluorine, chlorine, methyl, methoxyl or acetamido and $R_3$ is hydrogen or methoxyl.

19. A composition according to claim 15 wherein X is CH$_2$ or CH$_2$CH$_2$.

20. A composition according to claim 13 wherein the compound is 9-N-(3-Phenylpropyl)aminodeoxyclavulanic acid.

21. A composition according to claim 13 wherein the compound is 9-N-(4-Phenylbutyl)aminodeoxyclavulanic acid.

22. A composition according to claim 13 wherein the compound is 9-N-[2-(3,4-Dimethoxyphenyl)ethyl]aminodeoxyclavulanic acid.

23. A composition according to claim 13 wherein the compound is 9-N-(2-Phenylethyl)aminodeoxyclavulanic acid.

24. A composition according to claim 13 wherein the compound is 9-N-(3-Phenyl-2-methylpropyl)aminodeoxyclavulanic acid.

25. A composition according to claim 13 in oral administration form.

26. A composition according to claim 13 in a form suitable for administration by injection.

27. A method of treating bacterial infections in mammals which comprises administering to a mammal in need thereof an antibacterially effective amount of a compound of the formula (XVII):

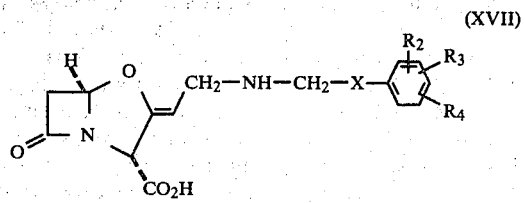

(XVII)

or an ester thereof of the formula (XVIII) or (XIX):

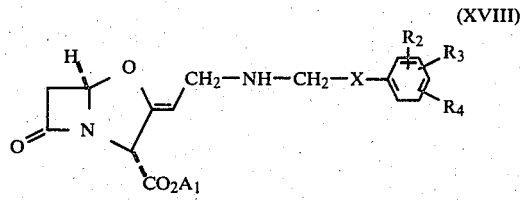

(XVIII)

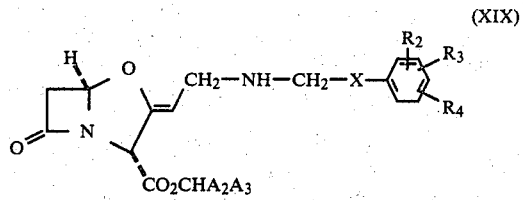

(XIX)

wherein $A_1$ is alkyl of 1 to 6 carbon atoms unsubstituted or mono-substituted by alkoxyl or alkanoyloxy of 1 to 7 carbon atoms, phthalidyl, ethoxycarbonyloxymethyl or α-ethoxycarbonyloxyethyl, $A_2$ is alkenyl or alkynyl of up to 5 carbon atoms or phenyl unsubstituted or mono-substituted by fluoro, chloro, bromo, nitro or alkyl or alkoxyl of up to 4 carbon atoms, $A_3$ is hydrogen, alkyl of up to 4 carbon atoms or phenyl unsubstituted or mono-substituted by fluoro, chloro, bromo, nitro, or alkyl or alkoxyl of up to 4 carbon atoms, $R_2$ is hydrogen, fluorine, chlorine, bromine, alkyl of 1 to 3 carbon atoms, alkoxy of 1 to 3 carbon atoms, alkanoyloxy of 1 to 3 carbon atoms, hydroxyl, alkoxycarbonyl of 1 to 3 carbon atoms in the alkoxy part, or a group —N($R_5$)CO.$R_6$ —N($R_5$)SO$_2$R$_6$ or —CO—NR$_5$R$_6$ wherein $R_5$ is hydrogen, alkyl of 1 to 3 carbon atoms, phenyl or benzyl and $R_6$ is alkyl of 1 to 3 carbon atoms, phenyl or benzyl; $R_3$ is hydrogen, fluorine, chlorine, alkyl group of 1 to 3 carbon atoms, alkoxy of 1 to 3 carbon atoms or alkanoyloxy of 1 to 3 carbon atoms; $R_4$ is hydrogen, fluorine, chlorine, alkyl group of 1 to 3 carbon atoms or alkoxyl of 1 to 3 carbon atoms; and X is alkylene of 1 to 4 carbon atoms, in combination with a pharmaceutically acceptable carrier.

28. A method according to claim 27 wherein the compound is in zwitterionic form.

29. A method according to claim 17 wherein $R_2$ is hydrogen, fluorine, chlorine, methoxyl, ethoxyl, hydroxyl, acetoxyl, propionyloxy, methyl, ethyl, methoxycarbonyl, ethoxycarbonyl or acetamido; $R_3$ is hydrogen, fluorine, chlorine, methoxy, ethoxyl, acetoxyl, propionoxyl, methyl or ethyl; and R₄ is hydrogen, fluorine, chlorine, methoxyl, ethoxyl, acetoxyl, propionoxyl, methyl or ethyl.

30. A method according to claim 27 wherein R₄ is hydrogen.

31. A method according to claim 27 or 28 wherein R₃ is hydrogen or methoxyl.

32. A method according to claim 30 wherein R₂ is hydrogen, fluorine, chlorine, methyl, methoxyl or acetamido and R₃ is hydrogen or methoxyl.

33. A method according to claim 29 wherein X is CH₂ or CH₂CH₂.

34. A method according to claim 27 wherein the compound is 9-N-(3-Phenylpropyl)aminodeoxyclavulanic acid.

35. A method according to claim 27 wherein the compound is 9-N-(4-Phenylbutyl)aminodeoxyclavulanic acid.

36. A method according to claim 27 wherein the compound is 9-N-[2-(3,4-Dimethoxyphenyl)ethyl]aminodeoxyclavulanic acid.

37. A method according to claim 27 wherein the compound is 9-N-(2-Phenylethyl)aminodeoxyclavulanic acid.

38. A method according to claim 27 wherein the compound is 9-N-(3-Phenyl-2-methylpropyl)aminodeoxyclavulanic acid.

39. A method according to claim 27 wherein the administration is oral.

40. A method according to claim 27 wherein the administration is in a form suitable by injection.

41. A method according to claim 9 wherein A₁ is —CH₂—CO—A₆ wherein A₆ is alkyl of up to 4 carbon atoms, phenyl, benzyl or phenyl or benzyl substituted by 1 or 2 alkyl or alkoxyl moieties of up to 3 carbon atoms, or by fluoro, chloro, bromo, or nitro.

42. A method according to claim 9 wherein A₁ is —CH₂—CO₂A₆ wherein A₆ is alkyl of up to 4 carbon atoms, phenyl, benzyl or phenyl or benzyl substituted by 1 or 2 alkyl or alkoxyl moieties of up to 3 carbon atoms, or by fluoro, chloro, bromo or nitro.

43. A method according to claim 9 wherein A₁ is —CH(CH₃)—CO₂A₆ wherein A₆ is alkyl of up to 4 carbon atoms, phenyl, benzyl or phenyl or benzyl substituted by 1 or 2 alkyl or alkoxyl moieties of up to 3 carbon atoms, or by fluoro, chloro, bromo or nitro.

44. A compound according to claim 1 wherein A₁ methyl, methoxymethyl, acetoxymethyl, acetoxyethyl, phthalidyl, ethoxycarbonyloxymethyl, or α-ethoxycarbonyloxyethyl.

45. A compound according to claim 1 wherein A₂ is phenyl or 4-methoxyphenyl.

46. A compound according to claim 1 wherein A₃ is hydrogen.

47. A composition according to claim 13 wherein A₁ is methyl, methoxymethyl, acetoxymethyl, acetoxyethyl, phthalidyl, ethoxycarbonyloxymethyl, or α-ethoxycarbonyloxyethyl.

48. A composition according to claim 13 wherein A₂ is phenyl or 4-methoxyphenyl.

49. A composition according to claim 13 wherein A₃ is hydrogen.

50. A method according to claim 27 wherein A₁ is methyl, methoxymethyl, acetoxymethyl, acetoxyethyl, phthalidyl, ethoxycarbonyloxymethyl, or α-ethoxycarbonyloxyethyl.

51. A method according to claim 27 wherein A₂ is phenyl or 4-methoxyphenyl.

52. A method according to claim 27 wherein A₃ is hydrogen.

53. An ester according to claim 1 which is the methyl, ethyl, n-propyl, n-butyl, allyl, CH₂—C≡CH, methoxymethyl, acetoxymethyl, propionoxymethyl, pivaloyloxymethyl, ethoxycarbonyloxymethyl, methoxycarbonyloxyethyl, ethoxycarbonyloxyethyl, dimethoxyphthalidyl, benzyl, methoxybenzyl, ethoxybenzyl, nitrobenzyl or chlorobenzyl ester.

54. A composition according to claim 47 wherein the compound is in the form of the methyl, ethyl, n-propyl, n-butyl, allyl, CH₂—C≡CH, methoxymethyl, acetoxymethyl, propionoxymethyl, pivaloyloxymethyl, ethoxycarbonyloxymethyl, methoxycarbonyloxyethyl, ethoxycarbonyloxyethyl, dimethoxyphthalidyl, benzyl, methoxybenzyl, ethoxybenzyl, nitrobenzyl or chlorbenzyl ester.

55. A method according to claim 54 wherein the compound is administered in the form of the methyl, ethyl, n-propyl, n-butyl, allyl, CH₂—C≡CH, methoxymethyl, acetoxymethyl, propionoxymethyl, pivaloyloxymethyl, ethoxycarbonyloxymethyl, methoxycarbonyloxyethyl, ethoxycarbonyloxyethyl, dimethoxyphthalidyl, benzyl, methoxybenzyl, ethoxybenzyl, nitrobenzyl or chlorobenzyl ester.

56. A compound of the formula (XVII):

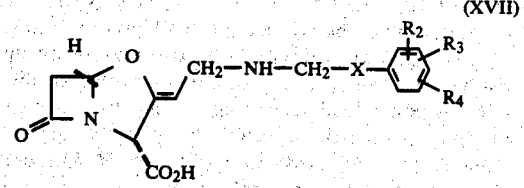

(XVII)

or an ester thereof of the formula (XVIII):

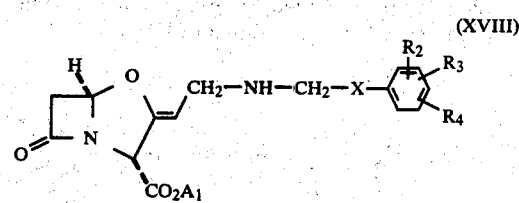

(XVIII)

wherein A₁ is tetrahydropyranyl, tetrahydrofuranyl or a moiety of the formula

—CHA₅—OA₆     (c)

—CHA₅—COA₆     (d)

—CHA₅—CO₂A₆     (e)

wherein
A₅ is hydrogen or methyl;
A₆ is alkyl of up to 4 carbon atoms, phenyl, benzyl or phenyl or benzyl substituted by one or two alkyl or alkoxy moieties of up to 3 carbon atoms or by fluoro, chloro, bromo or nitro, or A₅ is joined to A₆ to form an ortho-phenylene moiety unsubstituted or substituted by one or two alkyl or alkoxyl moieties of up to 3 carbon atoms or by fluoro, chloro, bromo or nitro,
R₂ is hydrogen, fluorine, chlorine, bromine, alkyl of 1 to 3 carbon atoms, alkoxy of 1 to 3 carbon atoms, alkanoyloxy of 1 to 3 carbon atoms, hydroxyl, alkoxycarbonyl of 1 to 3 carbon atoms in the alkoxy part, or a group —N(R$_5$)CO.R$_6$,—N(R$_5$)SO$_2$R$_6$ or —CO—NR$_5$R$_6$ wherein R$_5$ is hydrogen, alkyl of 1 to 3 carbon atoms, phenyl or benzyl and R$_6$ alkyl of 1 to 3 carbon atoms, phenyl or benzyl;

R$_3$ is hydrogen, fluorine, chlorine, alkyl group of 1 to 3 carbon atoms, alkoxy of 1 to 3 carbon atoms or alkanoyl of 1 to 3 carbon atoms;

R$_4$ is hydrogen, fluorine, chlorine, alkyl group of 1 to 3 carbon atoms or alkoxyl of 1 to 3 carbon atoms; and X is alkylene of 1 to 4 carbon atoms.

57. A compound accordng to claim 56 wherein A$_1$ is —CH$_2$—OA$_6$ wherein A$_6$ is alkyl of up to 4 carbon atoms, phenyl, benzyl or phenyl or benzyl substituted by 1 or 2 alkyl or alkoxyl moieties of up to 3 carbon atoms, or by fluoro, chloro, bromo or nitro.

58. A compound according to claim 56 wherein A$_1$ is —CH$_2$—CO—A$_6$ wherein A$_6$ is alkyl of up to 4 carbon atoms, phenyl, benzyl or phenyl or benzyl substituted by 1 or 2 alkyl or alkoxyl moieties of up to 3 carbon atoms, or by fluoro, chloro, bromo, or nitro.

59. A compound according to claim 56 wherein A$_1$ is —CH$_2$—CO$_2$A$_6$ wherein A$_6$ is alkyl of up to 4 carbon atoms, phenyl, benzyl or phenyl or benzyl substituted by 1 or 2 alkyl or alkoxyl moieties of up to 3 carbon atoms, or by fluoro, chloro, bromo or nitro.

60. A compound according to claim 56 wherein A$_1$ is —CH(CH$_3$)—CO$_2$A$_6$ wherein A$_6$ is alkyl of up to 4 carbon atoms, phenyl, benzyl or phenyl or benzyl substituted by 1 or 2 alkyl or alkoxyl moieties of up to 3 carbon atoms, or by fluoro, chloro, bromo or nitro.

61. A compound according to claim 56 wherein A$_6$ is methyl, ethyl, propyl, butyl, phenyl or benzyl.

62. A compound according to claim 56 wherein A$_1$ is tetrahydropyranyl or tetrahydrofuranyl.

63. A pharmaceutical composition useful for treating bacterial infections in mammals including humans which comprises an antibacterially effective amount of the compound of the formula (XVIII):

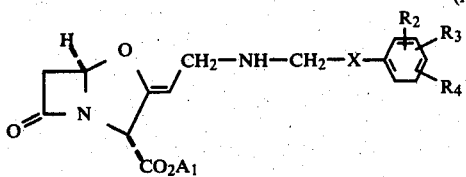

(XVIII)

wherein A$_1$ is tetrahydropyranyl, tetrahydrofuranyl or a moiety of the formula —CHA$_5$—OA$_6$    (c)

—CHA$_5$—COA$_6$    (d)

—CHA$_5$—CO$_2$A$_6$    (e)

wherein

A$_5$ is hydrogen or methyl;

A$_6$ is alkyl of up to 4 carbon atoms, phenyl, benzyl or phenyl or benzyl substituted by one or two alkyl or alkoxy moieties of up to 3 carbon atoms or by fluoro, chloro, bromo or nitro, or A$_5$ is joined to A$_6$ to form an ortho-phenylene moiety unsubstituted or substituted by one or two alkyl or alkoxyl moieties of up to 3 carbon atoms or by fluoro, chloro, bromo or nitro.

R$_2$ is hydrogen, fluorine, chlorine, bromine, alkyl of 1 to 3 carbon atoms, alkoxy of 1 to 3 carbon atoms, alkanoyloxy of 1 to 3 carbon atoms, hydroxyl, alkoxycarbonyl of 1 to 3 carbon atoms in the alkoxy part, or a group —N(R$_5$)CO.R$_6$—N(R$_5$)SO$_2$R$_6$ or —CO—NR$_5$R$_6$ wherein R$_5$ is hydrogen, alkyl of 1 to 3 carbon atoms, phenyl or benzyl and R$_6$ is alkyl of 1 to 3 carbon atoms, phenyl or benzyl;

R$_3$ is hydrogrn, fluorine, chlorine, alkyl group of 1 to 3 carbon atoms, alkoxy of 1 to 3 carbon atoms or alkanoyl of 1 to 3 carbon atoms;

R$_4$ is hydrogen, fluorine, chlorine, alkyl group to 1 to 3 carbon atoms or alkoxyl of 1 to 3 carbon atoms; and X is alkylene of 1 to 4 carbon atoms as the sole antibacterial agent, in combination with a pharmaceutically acceptable carrier.

64. A composition according to claim 63 wherein A$_1$ is —CH$_2$—OA$_6$ wherein A$_6$ is alkyl of up to 4 carbon atoms, phenyl, benzyl or phenyl or benzyl substituted by 1 or 2 alkyl or alkoxyl moieties of up to 3 carbon atoms, or by fluoro, chloro, bromo or nitro.

65. A composition according to claim 63 wherein A$_1$ is —CH$_2$—CO—A$_6$ wherein A$_6$ is alkyl of up to 4 carbon atoms, phenyl, benzyl or phenyl or benzyl substituted by 1 or 2 alkyl or alkoxyl moieties of up to 3 carbon atoms, or by fluoro, chloro, bromo, or nitro.

66. A composition according to claim 63 wherein A$_1$ is —CH$_2$—CO$_2$A$_6$ wherein A$_6$ is alkyl of up to 4 carbon atoms, phenyl, benzyl or phenyl or benzyl substituted by 1 or 2 alkyl or alkoxyl moieties of up to 3 carbon atoms, or by fluoro, chloro, bromo or nitro.

67. A composition according to claim 63 wherein A$_1$ is —CH(CH$_3$)—CO$_2$A$_6$ wherein A$_6$ is alkyl of up to 4 carbon atoms, phenyl, benzyl or phenyl or benzyl substituted by 1 or 2 alkyl or alkoxyl moieties of up to 3 carbon atoms, or by fluoro, chloro, bromo or nitro.

68. A composition according to claim 63 wherein A$_6$ is methyl, ethyl, propyl, butyl, phenyl or benzyl.

69. A composition according to claim 63 wherein A$_1$ is tetrahydropyranyl or tetrahydrofuranyl.

* * * * *